(12) United States Patent
Jo et al.

(10) Patent No.: US 9,956,554 B2
(45) Date of Patent: May 1, 2018

(54) CENTRIFUGATION METHOD WITH A REVERSED SYRINGE POSITION

(75) Inventors: Chris Hyunchul Jo, Seoul (KR); Sue Shin, Seoul (KR); Kang Sup Yoon, Seoul (KR)

(73) Assignee: SNU R&DB FOUNDATION (KR)

( * ) Notice: Subject to any disclaimer, the term of this patent is extended or adjusted under 35 U.S.C. 154(b) by 532 days.

(21) Appl. No.: 13/878,995

(22) PCT Filed: Oct. 12, 2011

(86) PCT No.: PCT/KR2011/007556
§ 371 (c)(1),
(2), (4) Date: Jun. 3, 2013

(87) PCT Pub. No.: WO2012/050351
PCT Pub. Date: Apr. 19, 2012

(65) Prior Publication Data
US 2014/0148325 A1 May 29, 2014

(30) Foreign Application Priority Data

Oct. 12, 2010 (KR) .................. 10-2010-0099123
Oct. 12, 2010 (KR) .................. 10-2010-0099124
(Continued)

(51) Int. Cl.
*B01L 3/00* (2006.01)
*A61M 1/36* (2006.01)
(Continued)

(52) U.S. Cl.
CPC ......... *B01L 3/5021* (2013.01); *A61M 1/3693* (2013.01); *B04B 5/0414* (2013.01);
(Continued)

(58) Field of Classification Search
CPC .................. A61M 1/3693; A61M 5/19; A61M 2202/0427; B04B 5/0414; G01N 33/491; B01L 3/5021
(Continued)

(56) References Cited

U.S. PATENT DOCUMENTS 3,882,021 A * 5/1975 Ayres ..................... B01D 33/01
210/136
5,016,784 A * 5/1991 Batson ............. B05C 17/00516
206/384
(Continued)

FOREIGN PATENT DOCUMENTS

DE 2108746 A1 * 11/1972 ........ A61M 5/31511
EP 446450 * 9/1991
(Continued)

OTHER PUBLICATIONS

DE 2108746 Espacenet Machine Translation.*
PCT/KR2011/007556 International Search Report dated Jul. 9, 2012.

*Primary Examiner* — Charles E Cooley
*Assistant Examiner* — Shuyi S. Liu
(74) *Attorney, Agent, or Firm* — Kunzler, PC

(57) ABSTRACT

According to one exemplary embodiment of the present invention, a method of centrifuging a mixture using a syringe which has a nozzle at one end, comprises the steps of taking the mixture in the syringe, first centrifuging the mixture in the syringe, discharging one part of the mixture which is adjacent to the nozzle after the first centrifuging, second centrifuging the mixture in the syringe after reversing the syringe, and discharging another part of the mixture which is adjacent to the nozzle after the second centrifuging.

5 Claims, 84 Drawing Sheets

(30) Foreign Application Priority Data

| | | |
|---|---|---|
| Oct. 12, 2010 | (KR) | 10-2010-0099125 |
| Oct. 12, 2010 | (KR) | 10-2010-0099126 |
| Oct. 12, 2010 | (KR) | 10-2010-0099128 |
| Mar. 7, 2011 | (KR) | 10-2011-0020074 |
| Jun. 20, 2011 | (KR) | 10-2011-0059743 |

(51) Int. Cl.
*G01N 33/49* (2006.01)
*B04B 5/04* (2006.01)
*A61M 5/19* (2006.01)

(52) U.S. Cl.
CPC .............. *G01N 33/491* (2013.01); *A61M 5/19* (2013.01); *A61M 2202/0427* (2013.01)

(58) Field of Classification Search
USPC ................................ 494/37, 56, 85; 422/521
See application file for complete search history.

(56) References Cited

U.S. PATENT DOCUMENTS

| | | | | |
|---|---|---|---|---|
| 5,968,018 A | * | 10/1999 | Freeman | B01F 5/0688 |
| | | | | 604/191 |
| 6,716,187 B1 | * | 4/2004 | Jorgensen | A61M 1/029 |
| | | | | 206/223 |
| 7,195,606 B2 | * | 3/2007 | Ballin | 604/6.01 |
| 2004/0116876 A1 | | 6/2004 | La | |
| 2007/0265558 A1 | * | 11/2007 | Kleinbloesem | A61M 1/029 |
| | | | | 604/5.01 |
| 2008/0234633 A1 | | 9/2008 | Nielsen | |
| 2011/0130263 A1 | * | 6/2011 | Del Vecchio | B04B 5/0421 |
| | | | | 494/9 |

FOREIGN PATENT DOCUMENTS

| KR | 100917795 B1 | 9/2009 |
|---|---|---|
| KR | 100953998 B1 | 4/2010 |

\* cited by examiner

[Fig. 1]
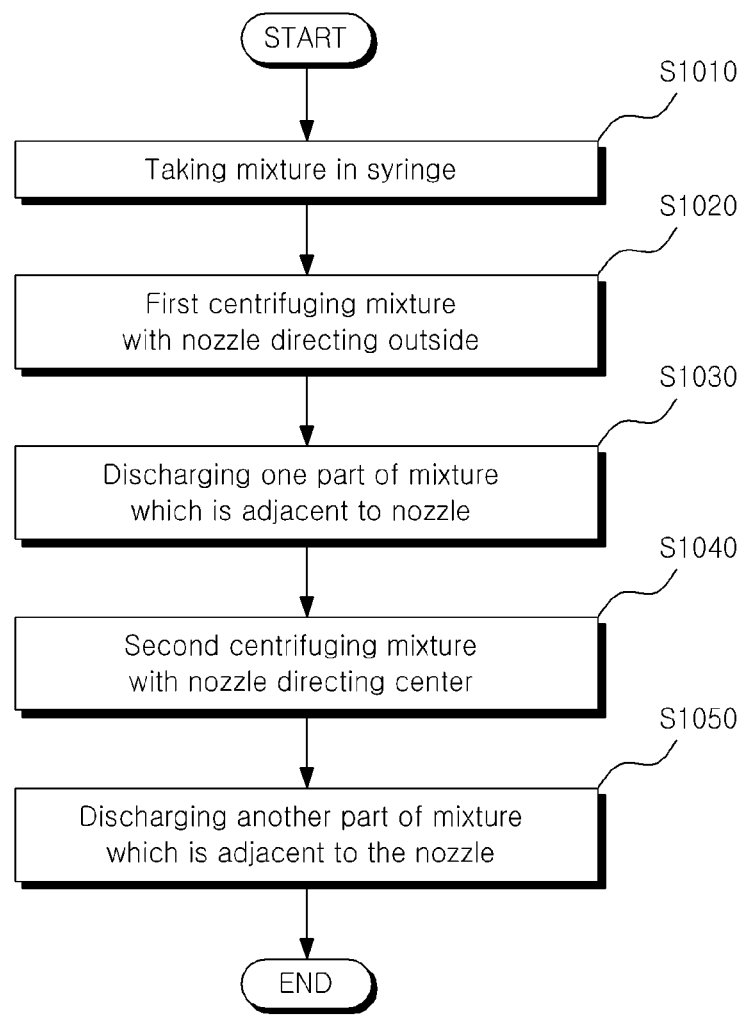

【Fig. 2】
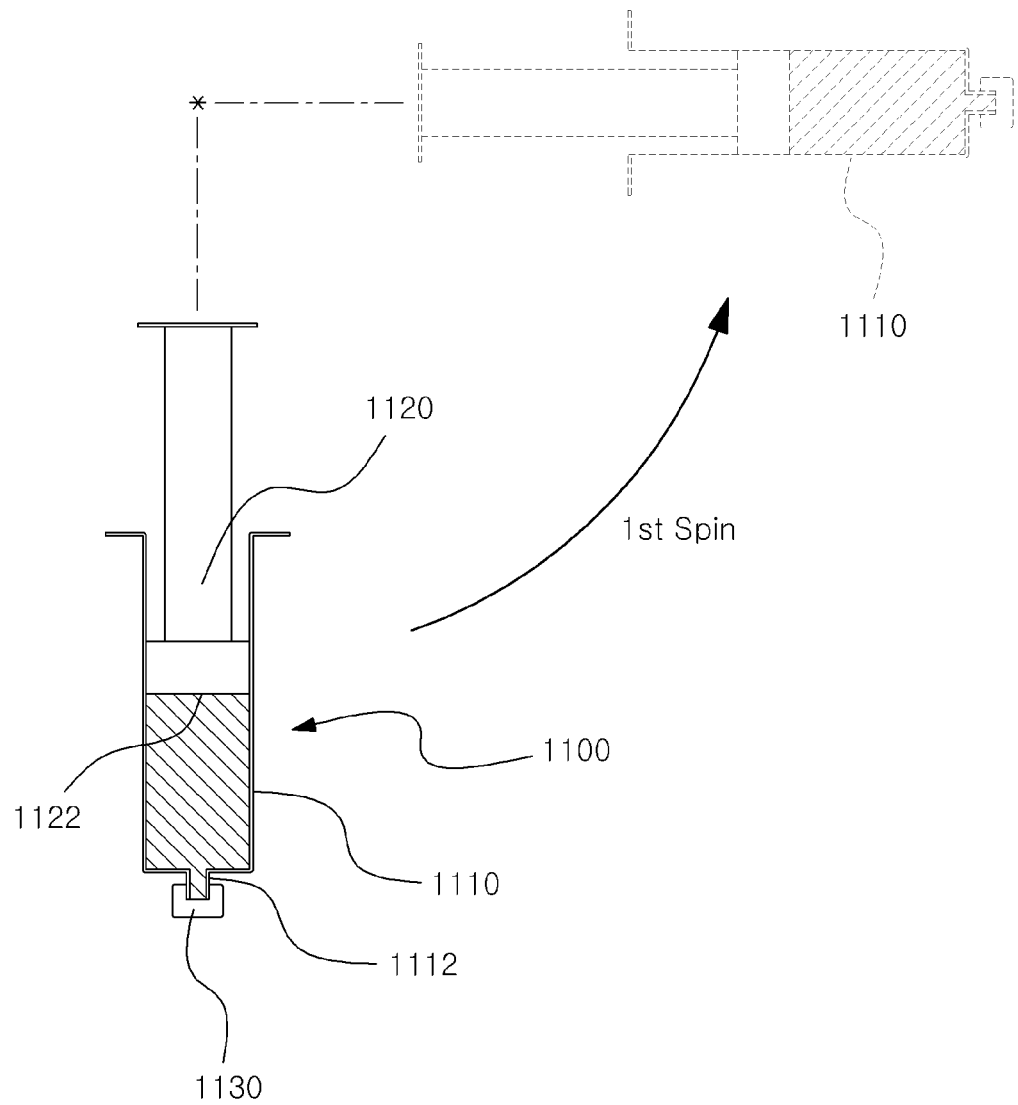

[Fig. 3]
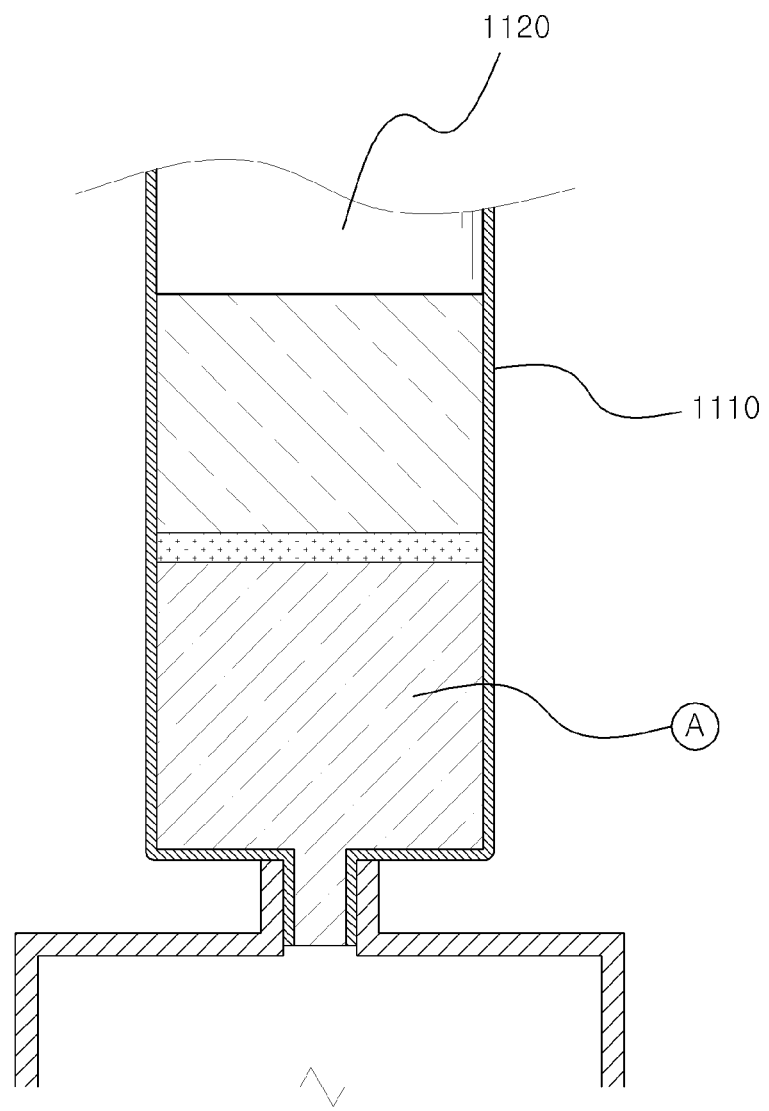

[Fig. 4]
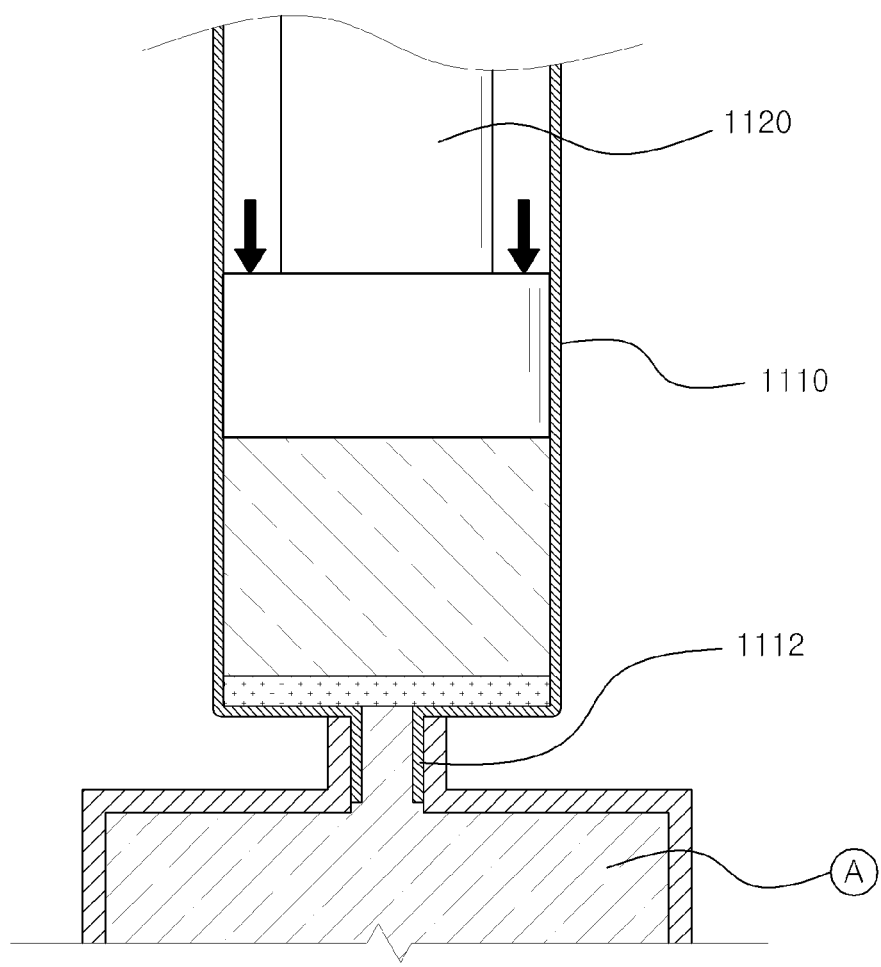

[Fig. 5]
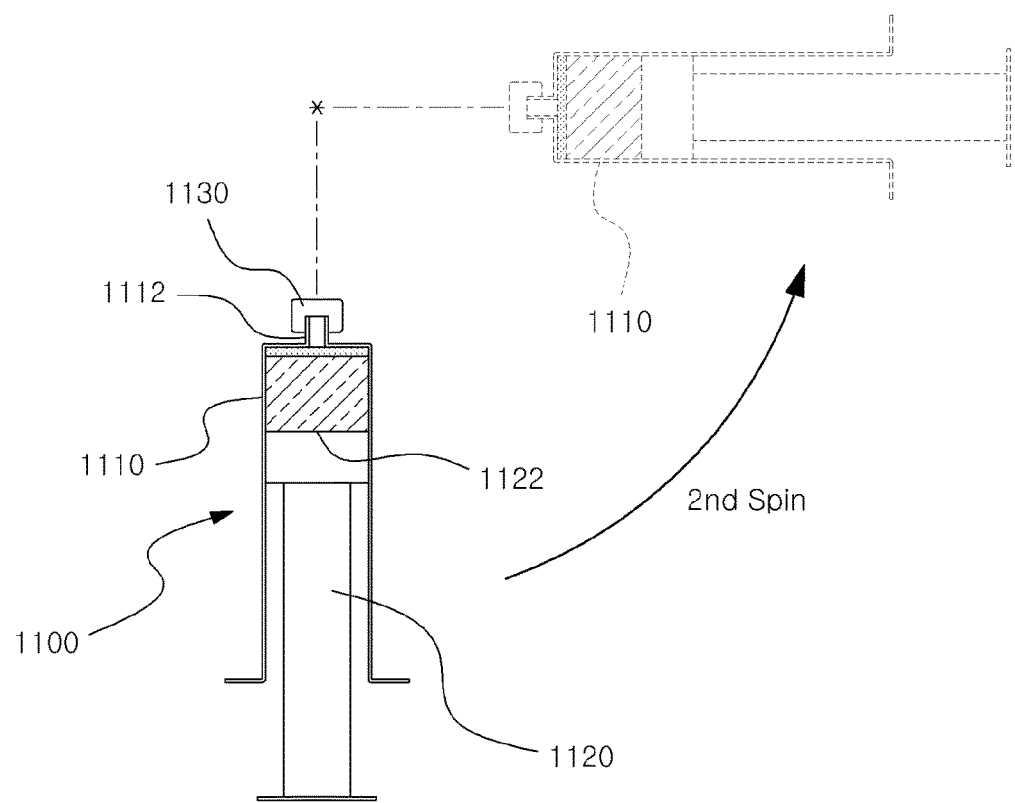

【Fig. 6】
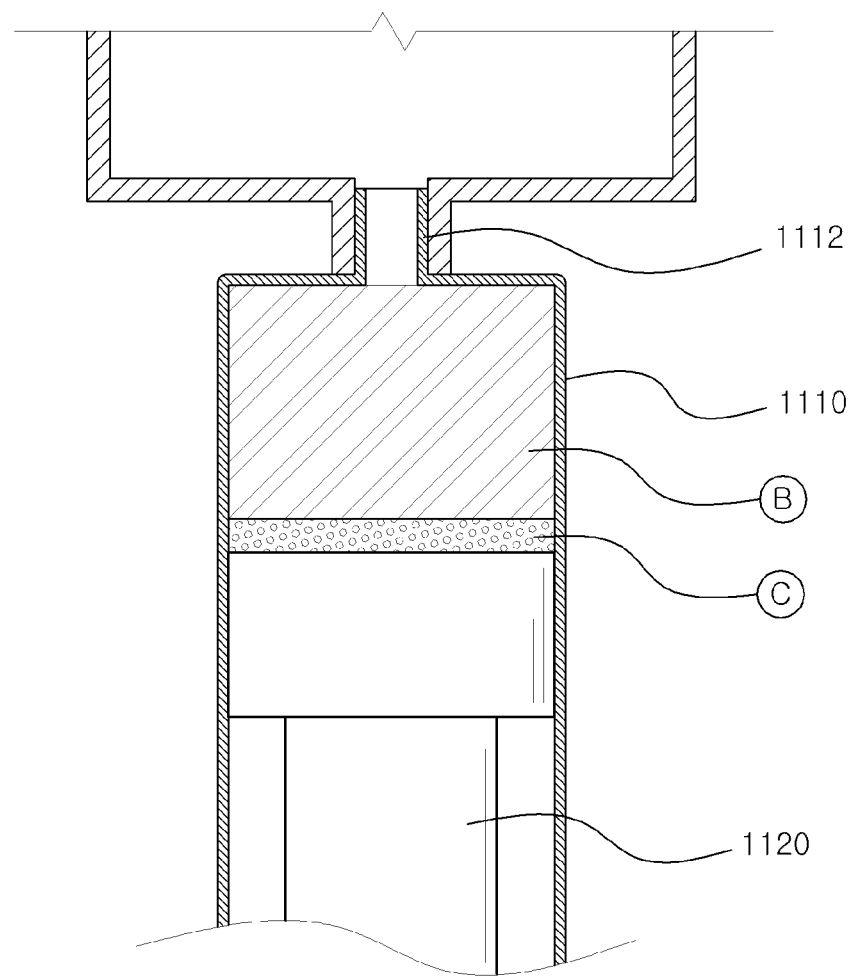

[Fig. 7]
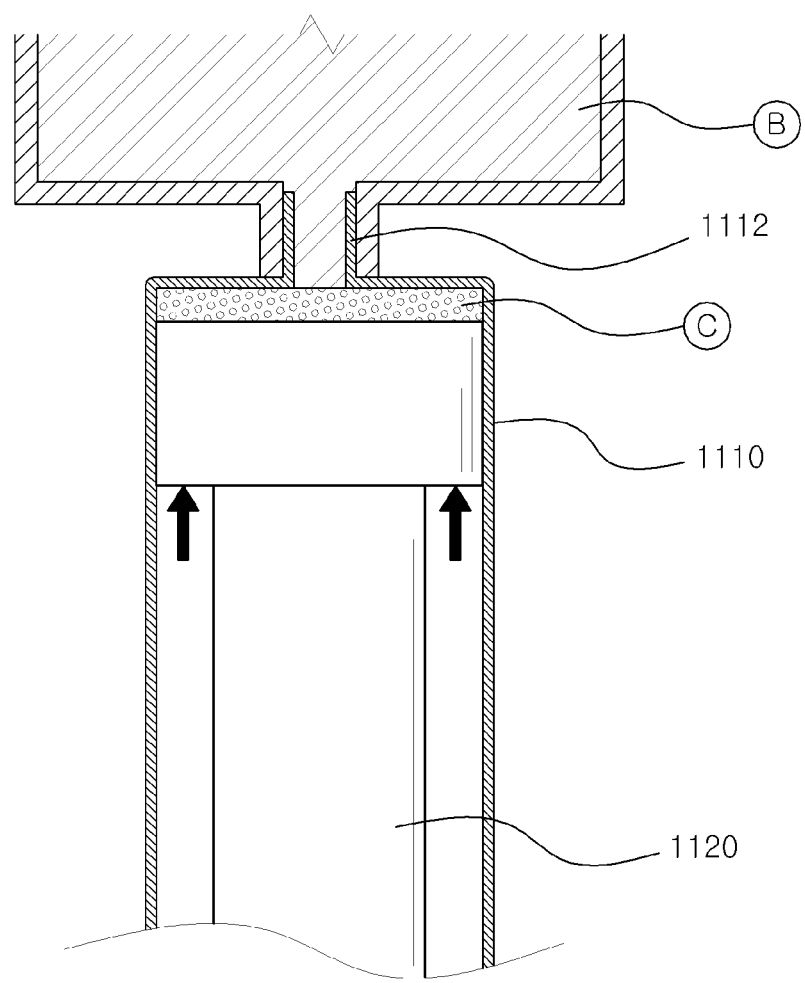

[Fig. 8]
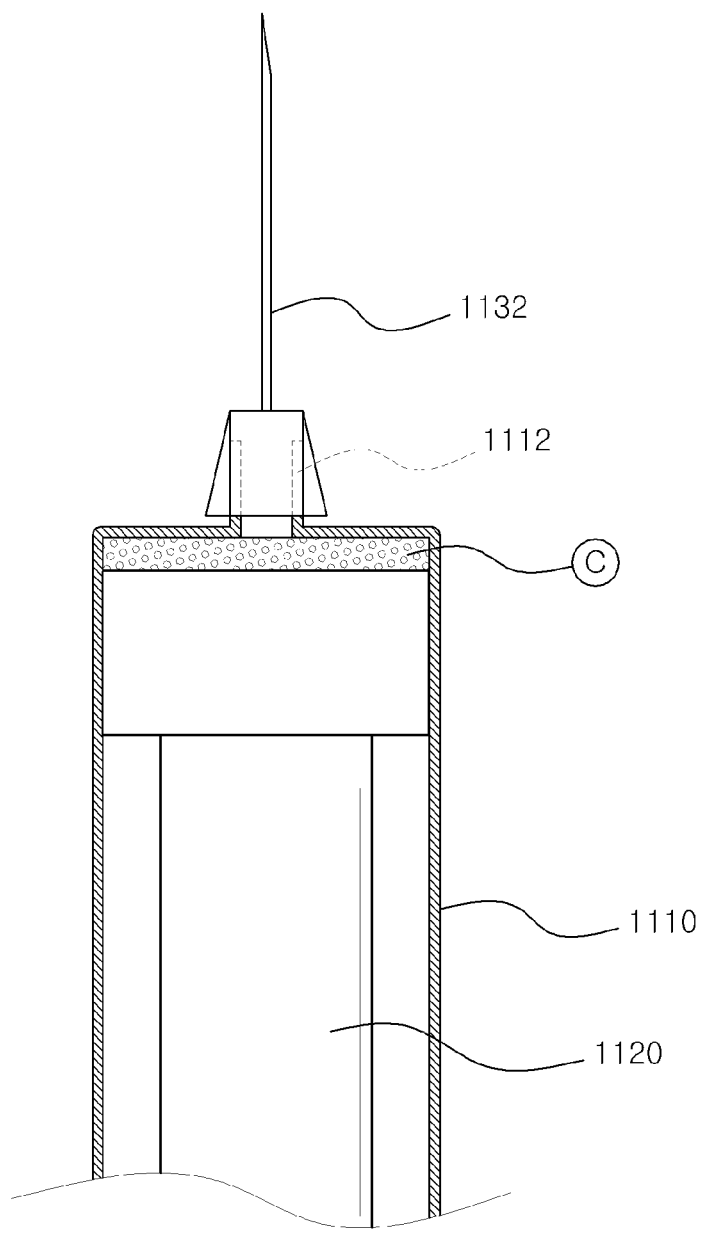

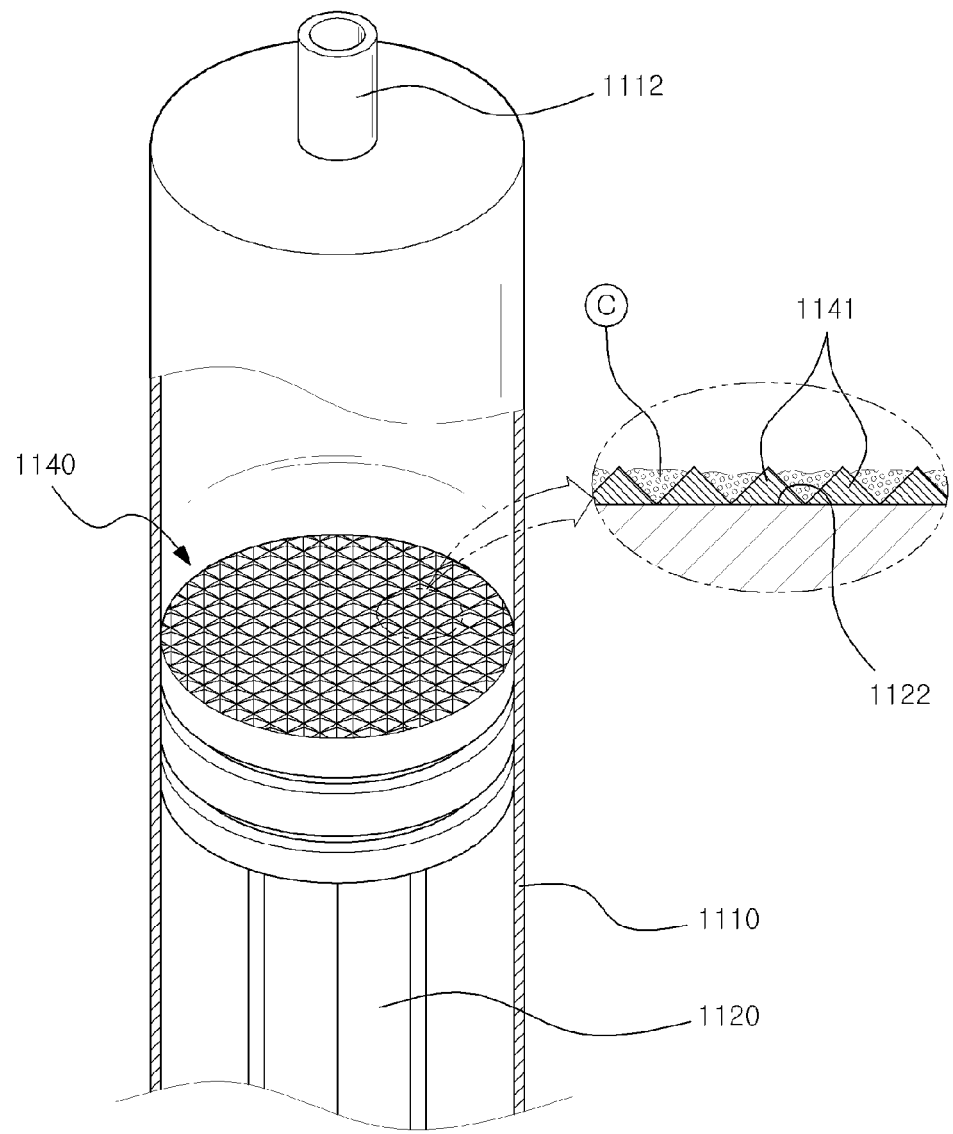
[Fig. 9]

[Fig. 10]
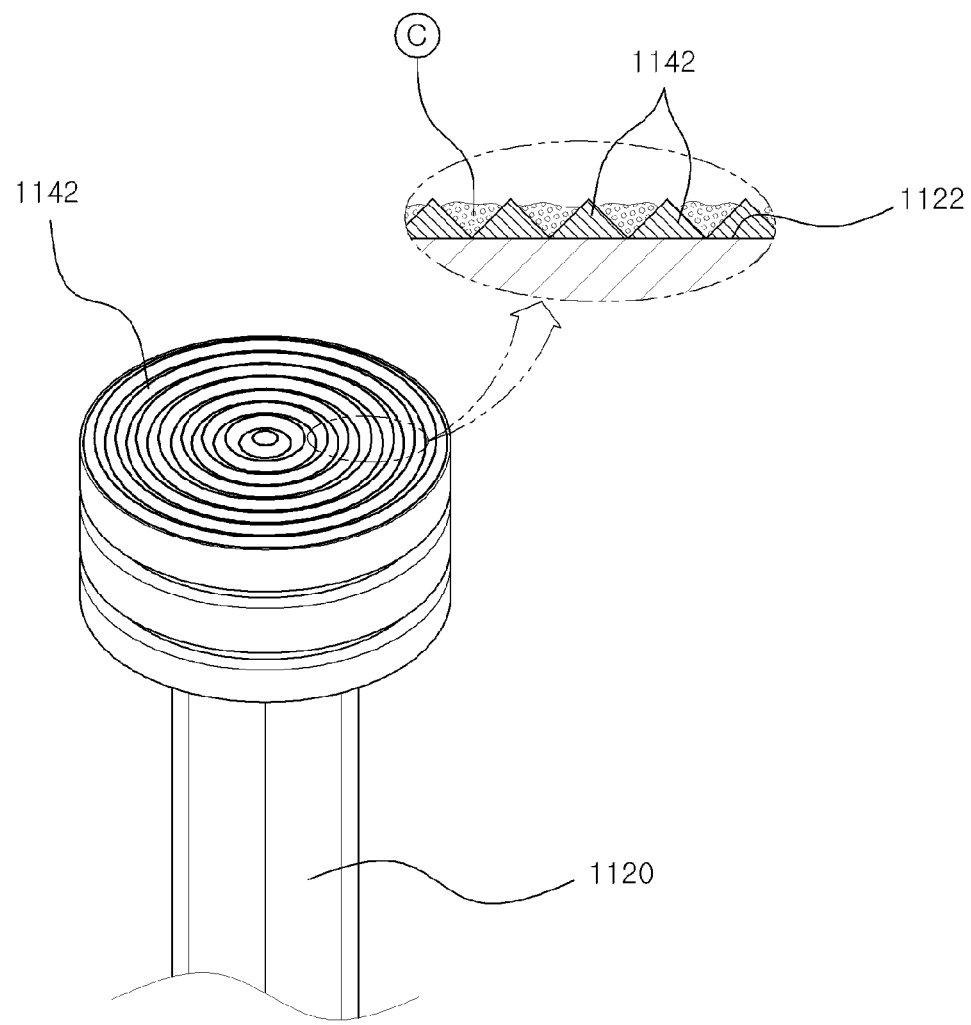

[Fig. 11]
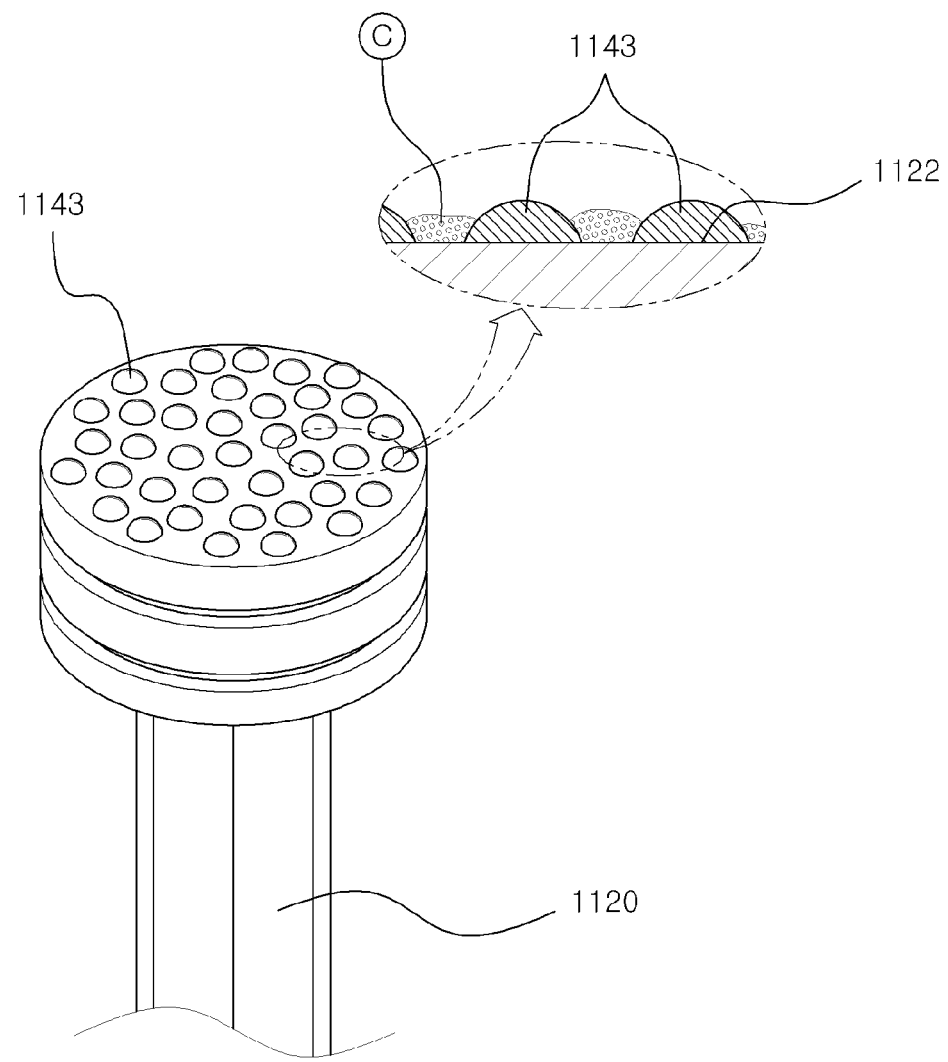

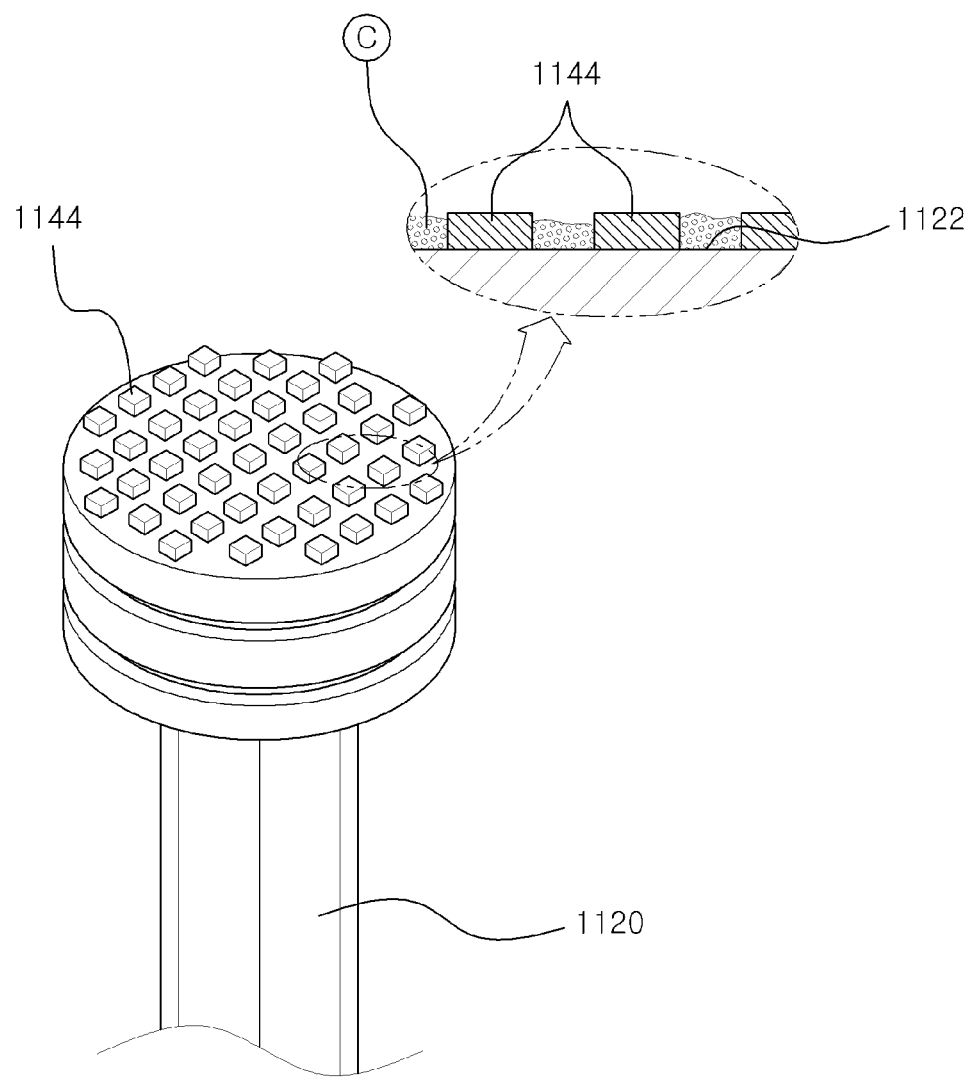
[Fig. 12]

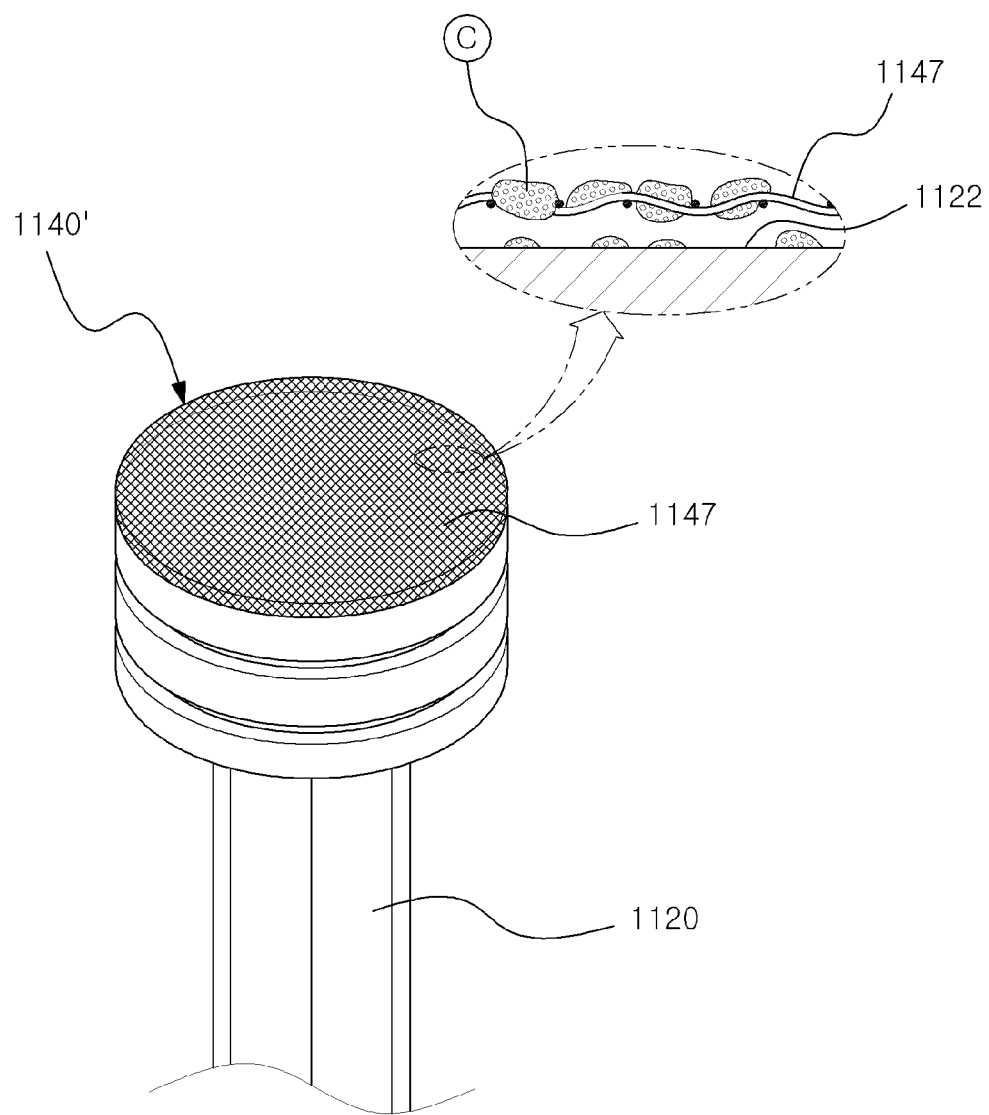
[Fig. 13]

[Fig. 14]
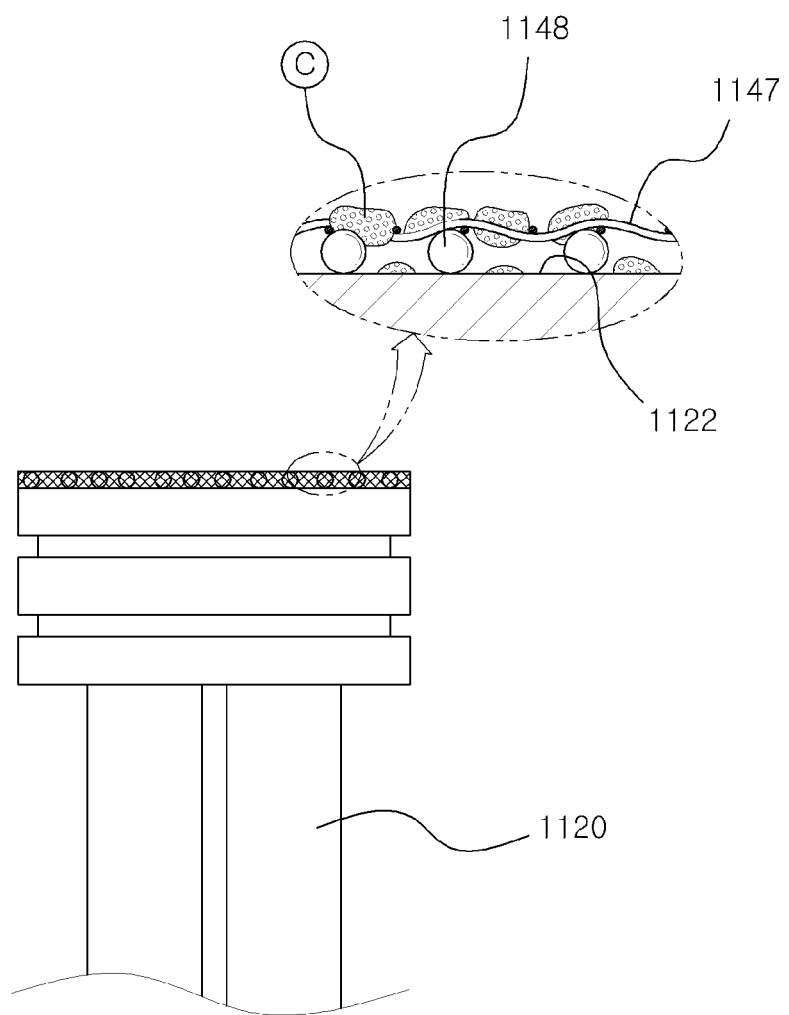

[Fig. 15]
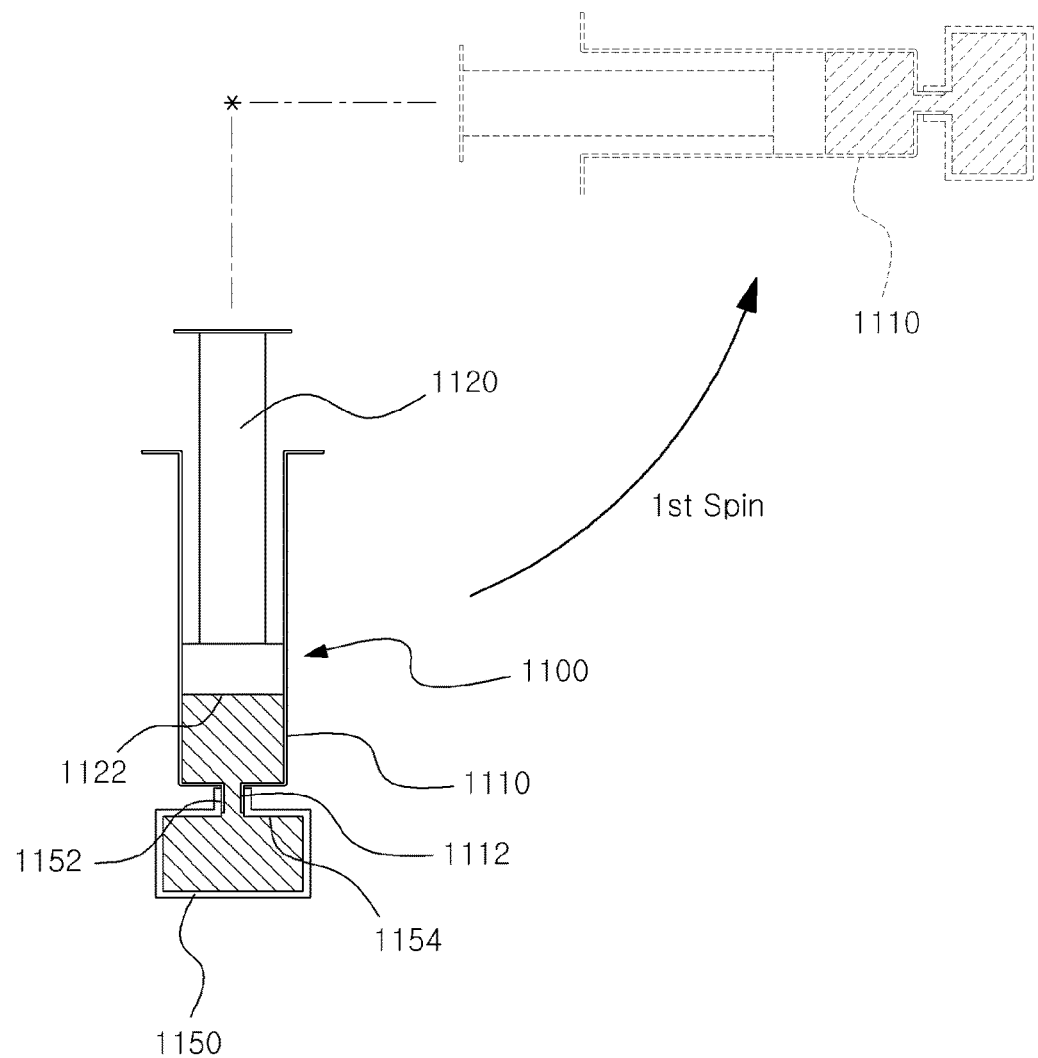

【Fig. 16】
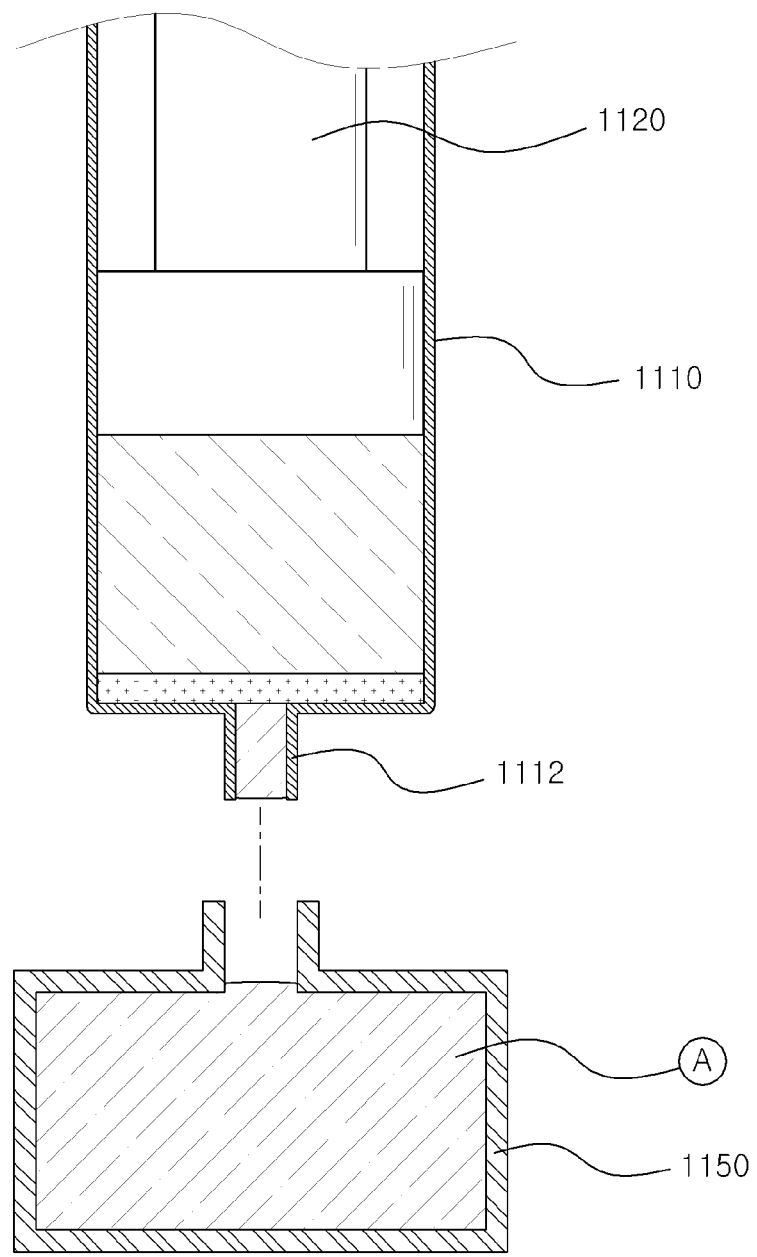

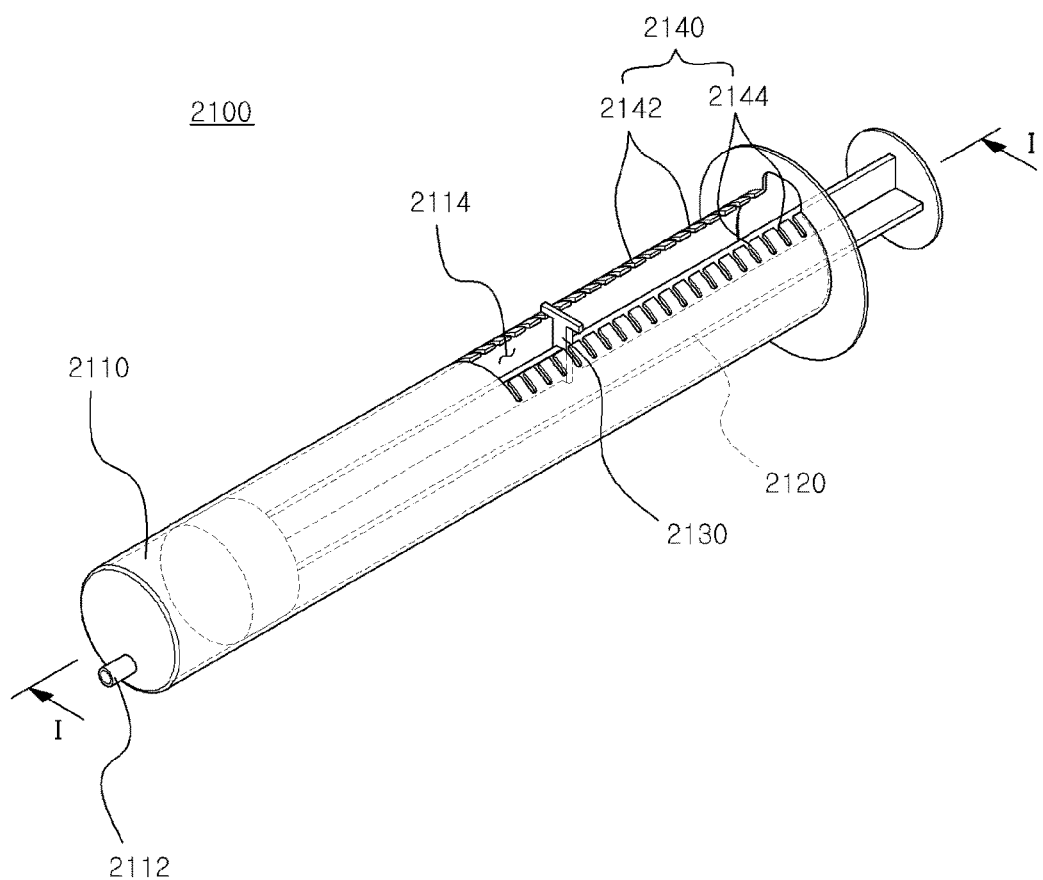
[Fig. 17]

[Fig. 18]
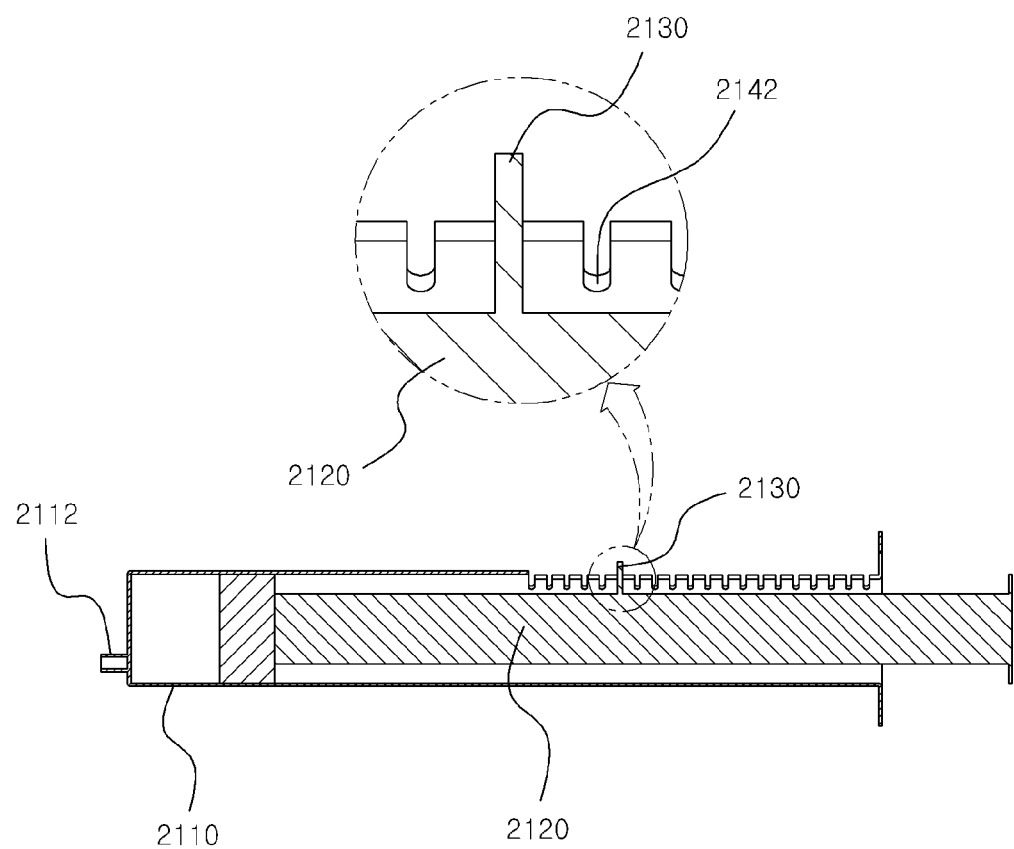

[Fig. 19]
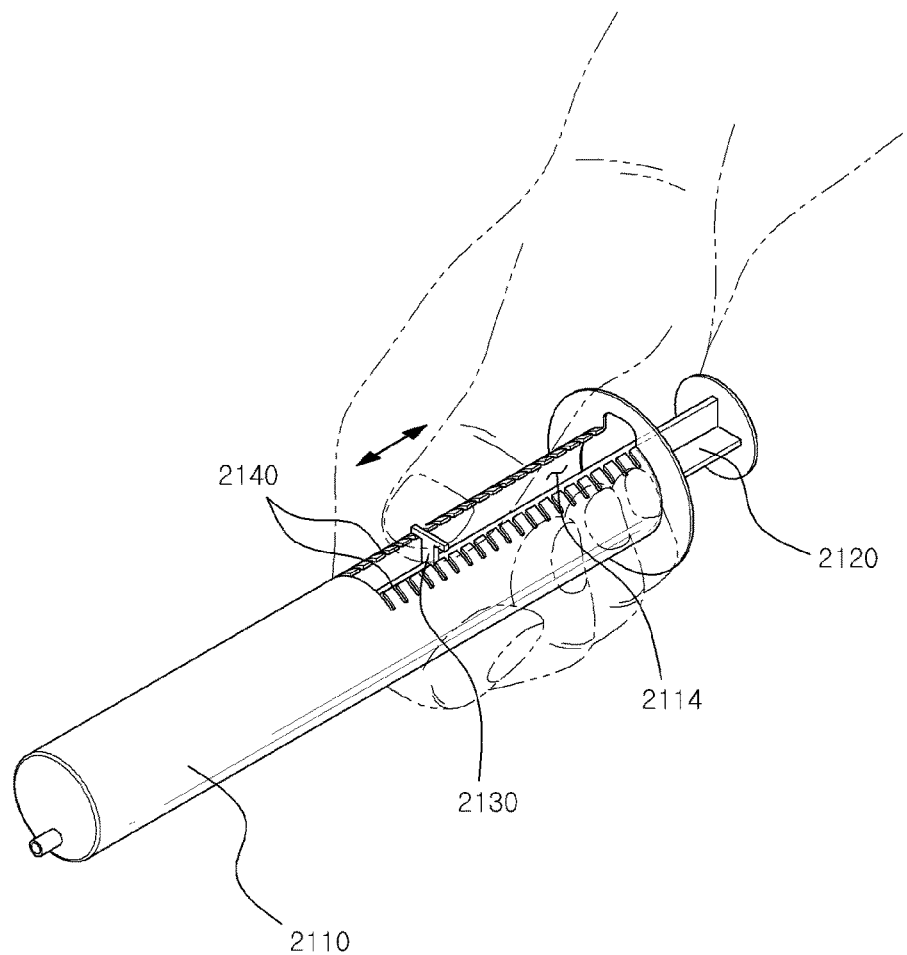

[Fig. 20]
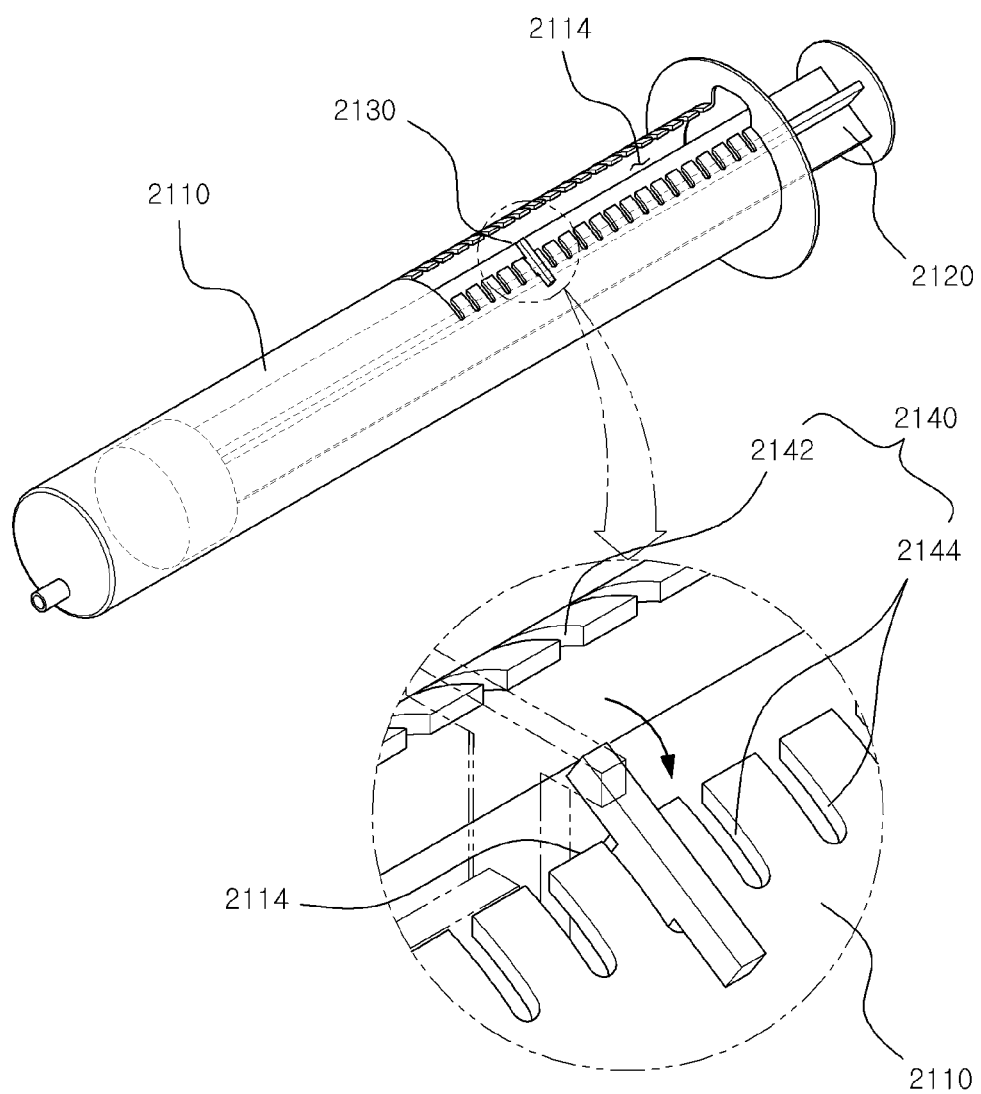

[Fig. 21]
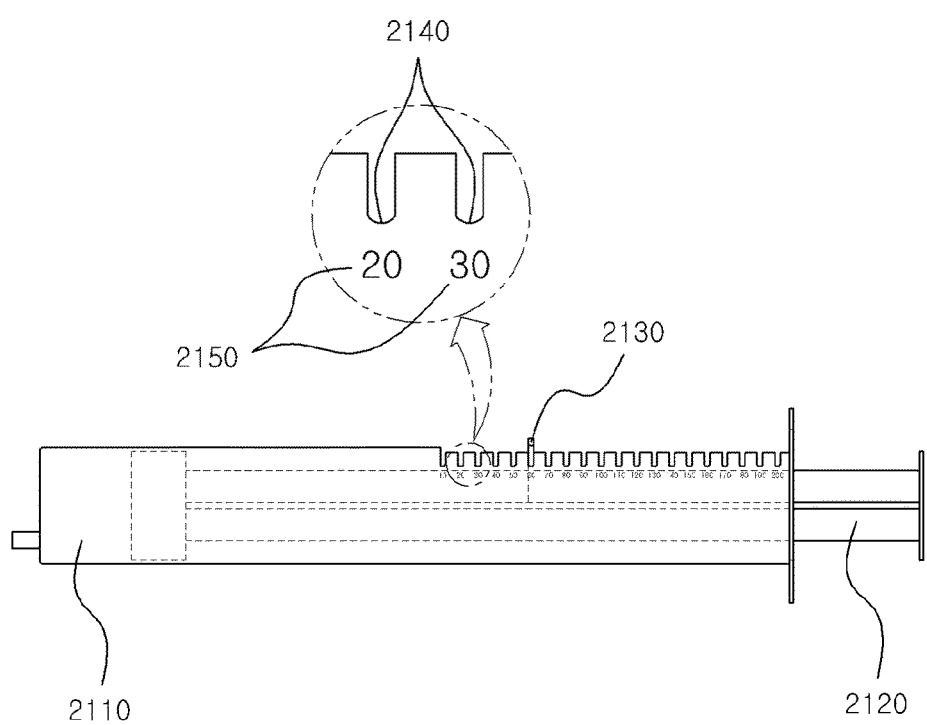

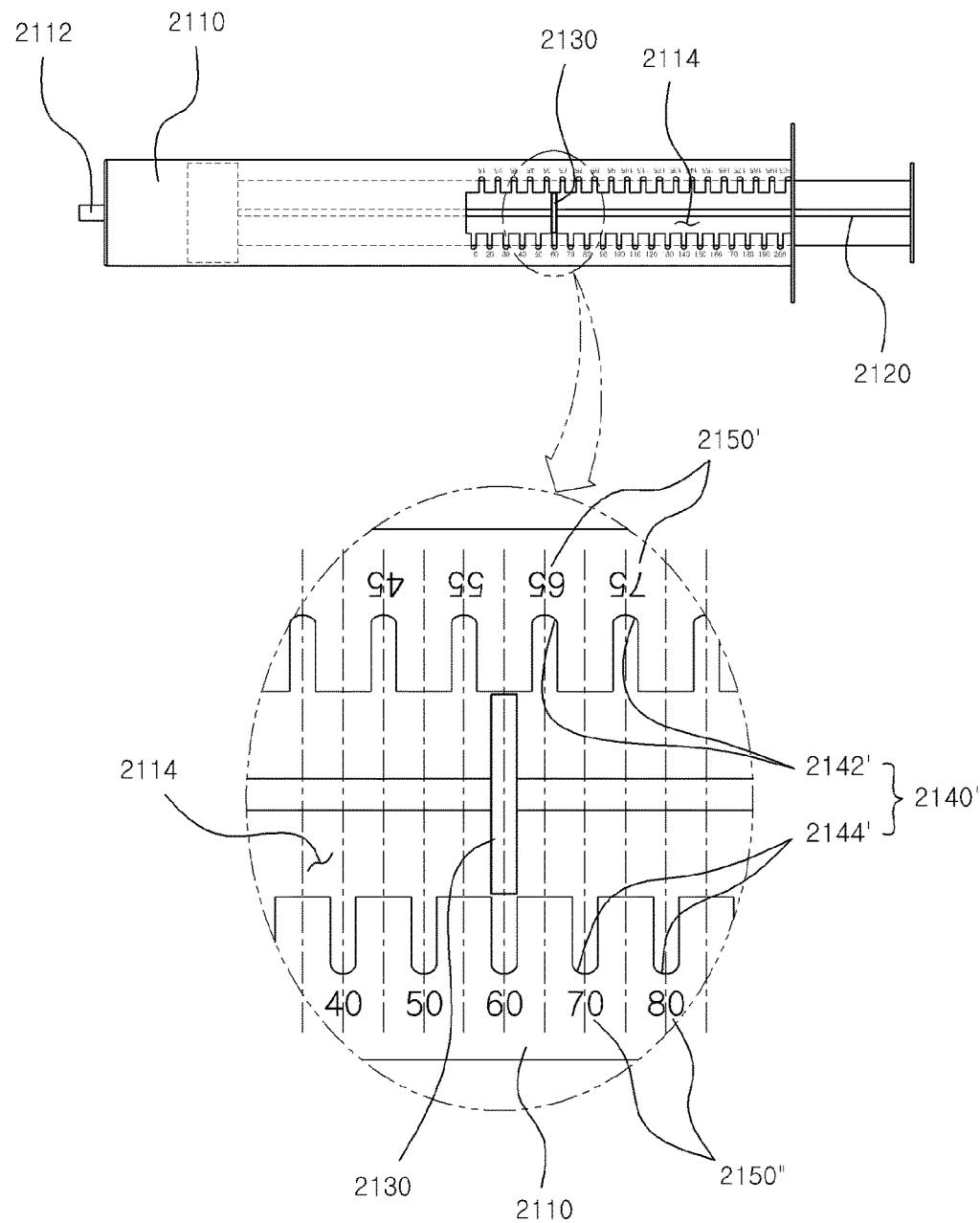
[Fig. 22]

[Fig. 23]
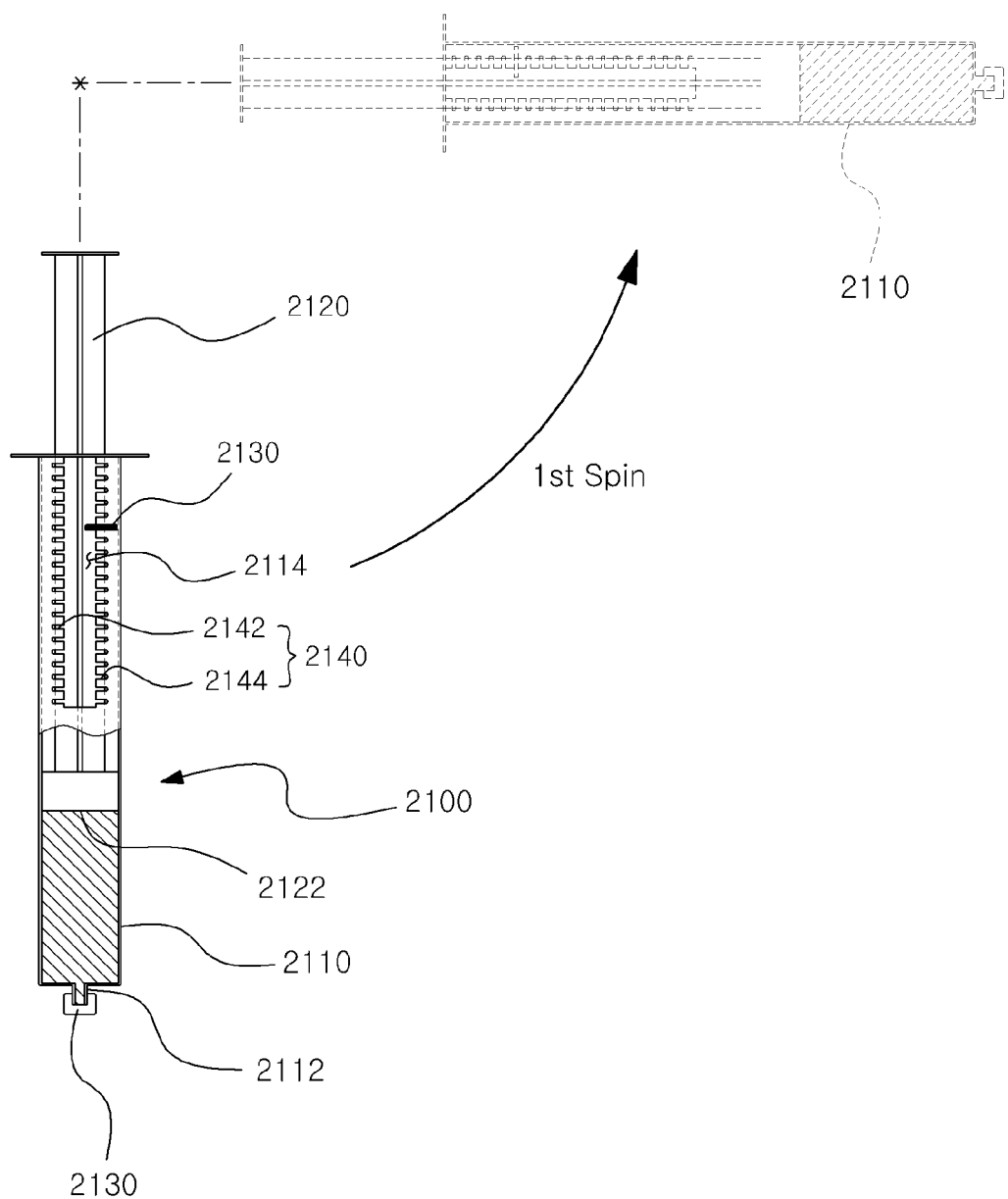

[Fig. 24]
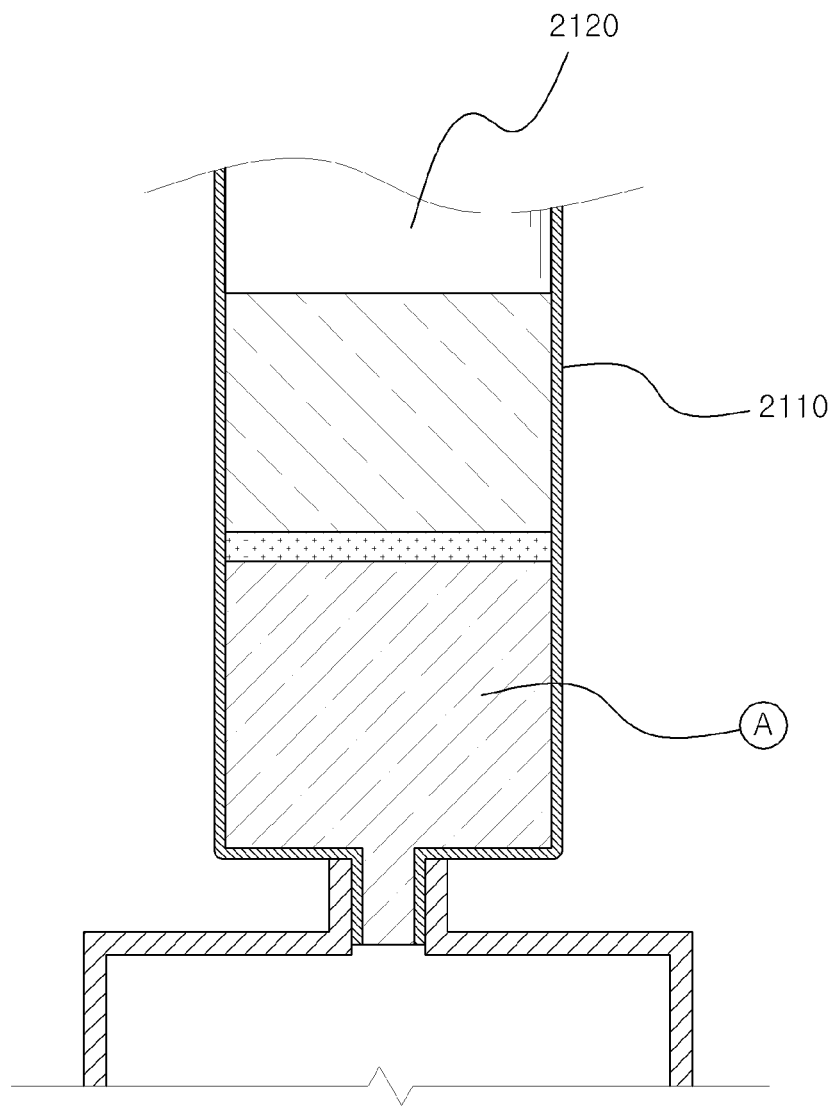

[Fig. 25]
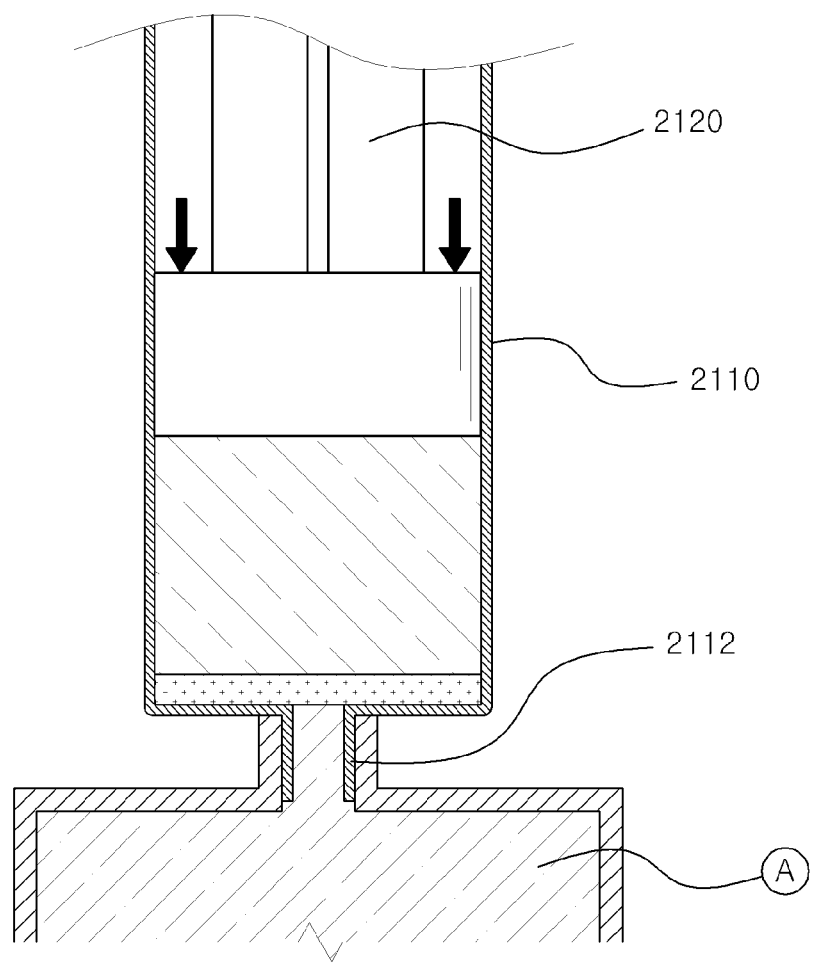

[Fig. 26]
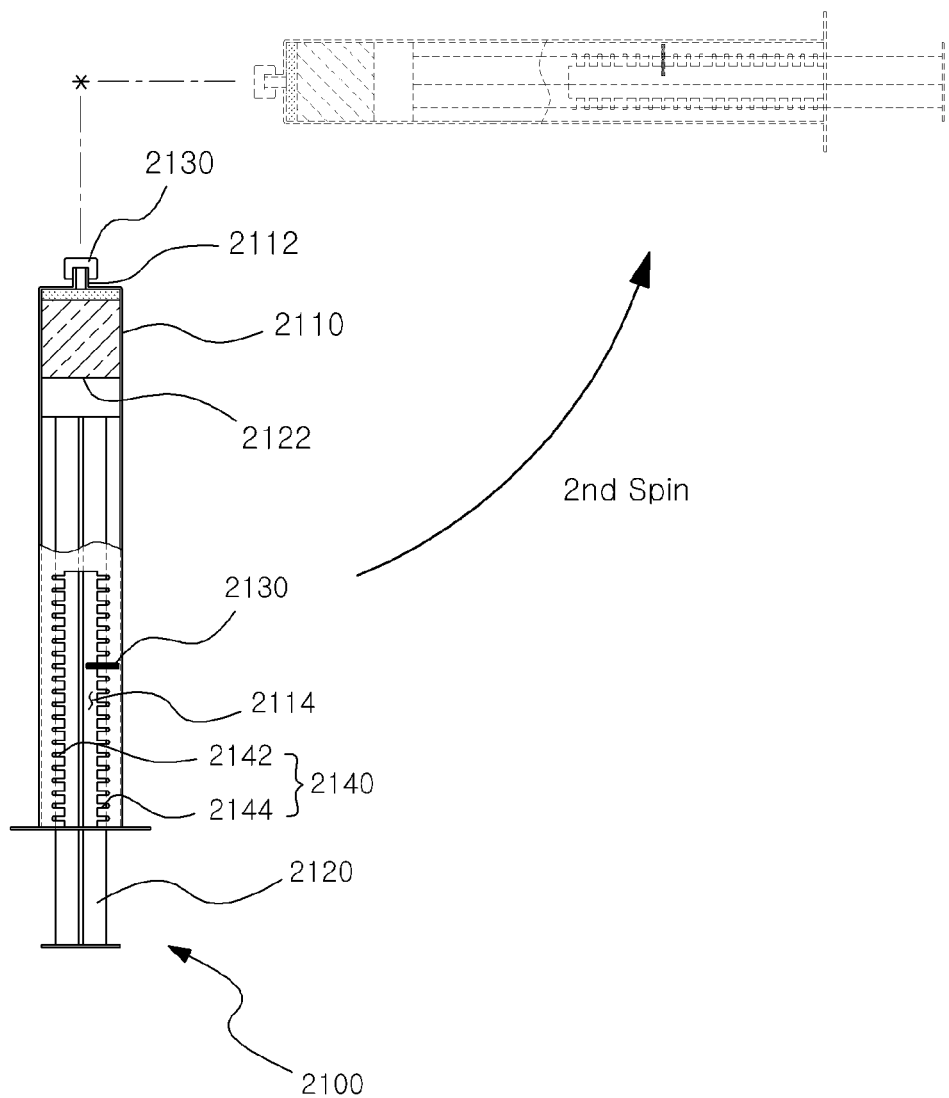

【Fig. 27】
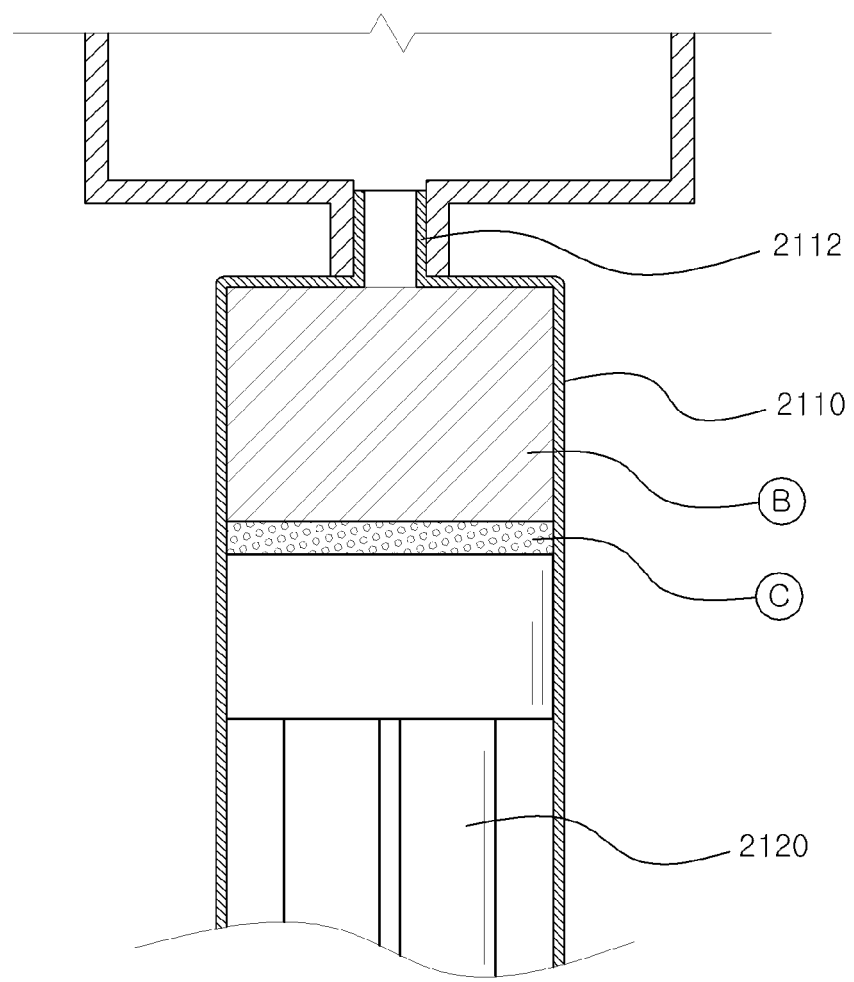

【Fig. 28】
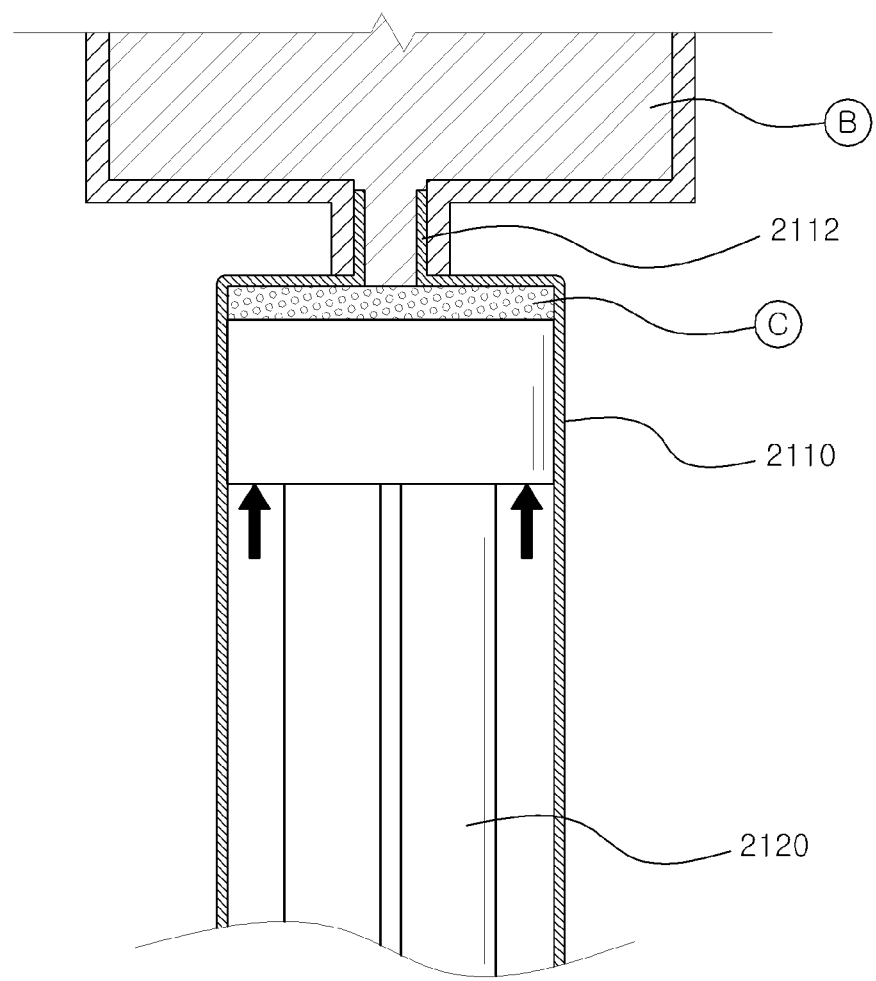

【Fig. 29】
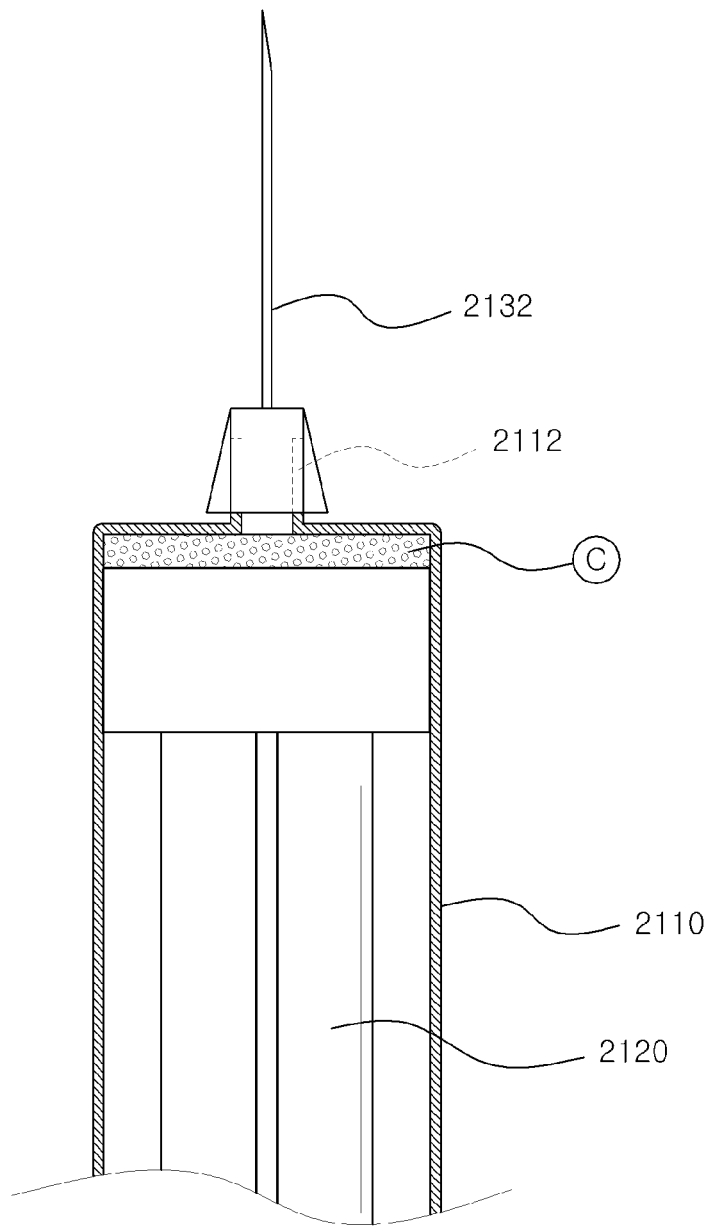

【Fig. 30】
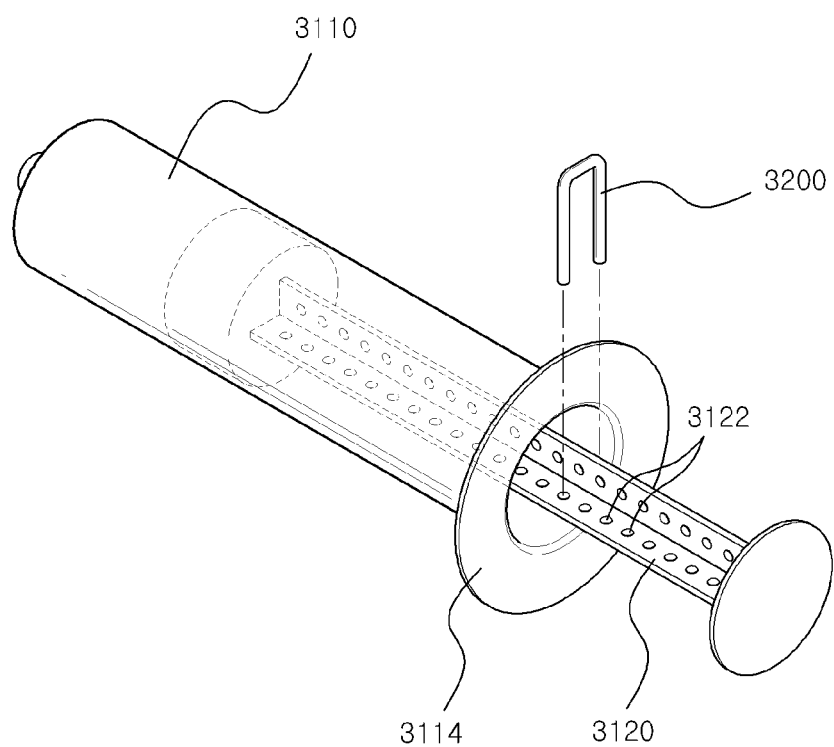

[Fig. 31]
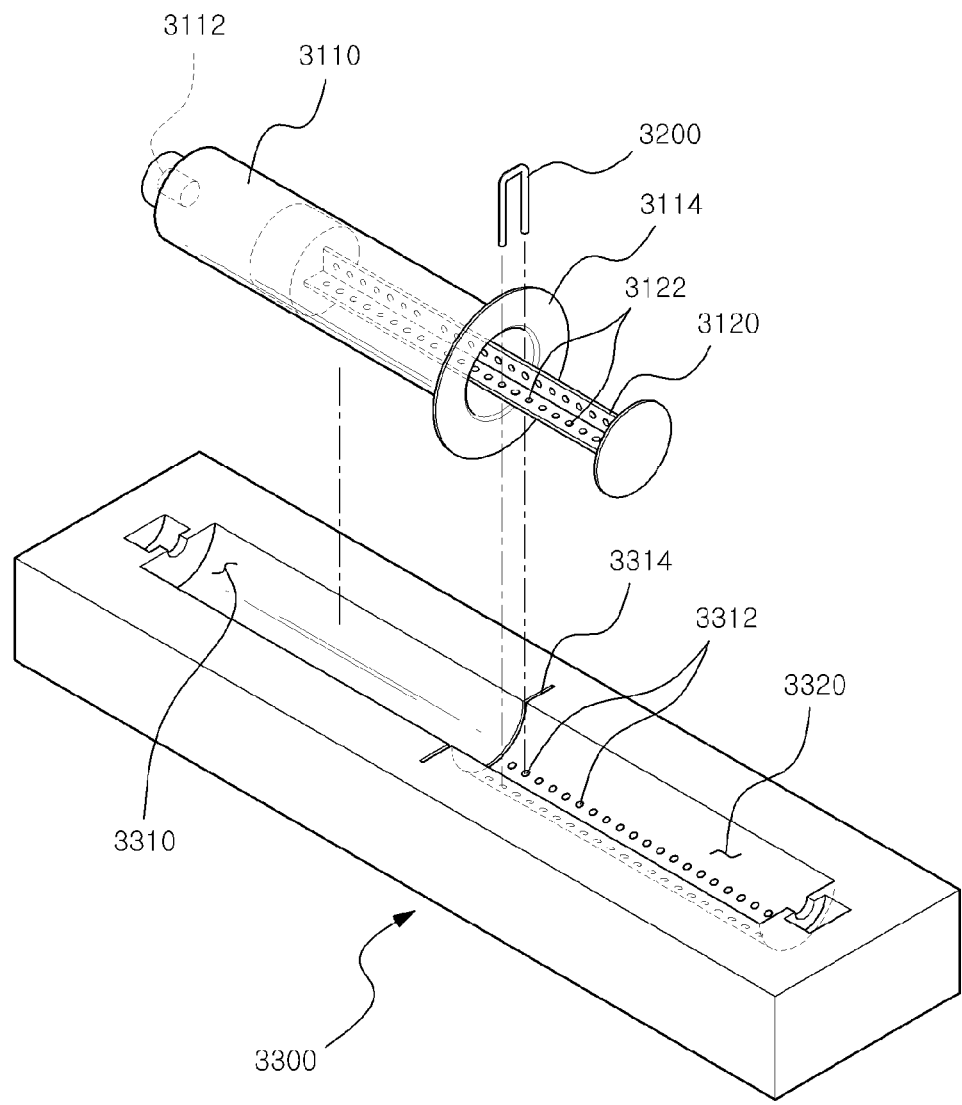

[Fig. 32]
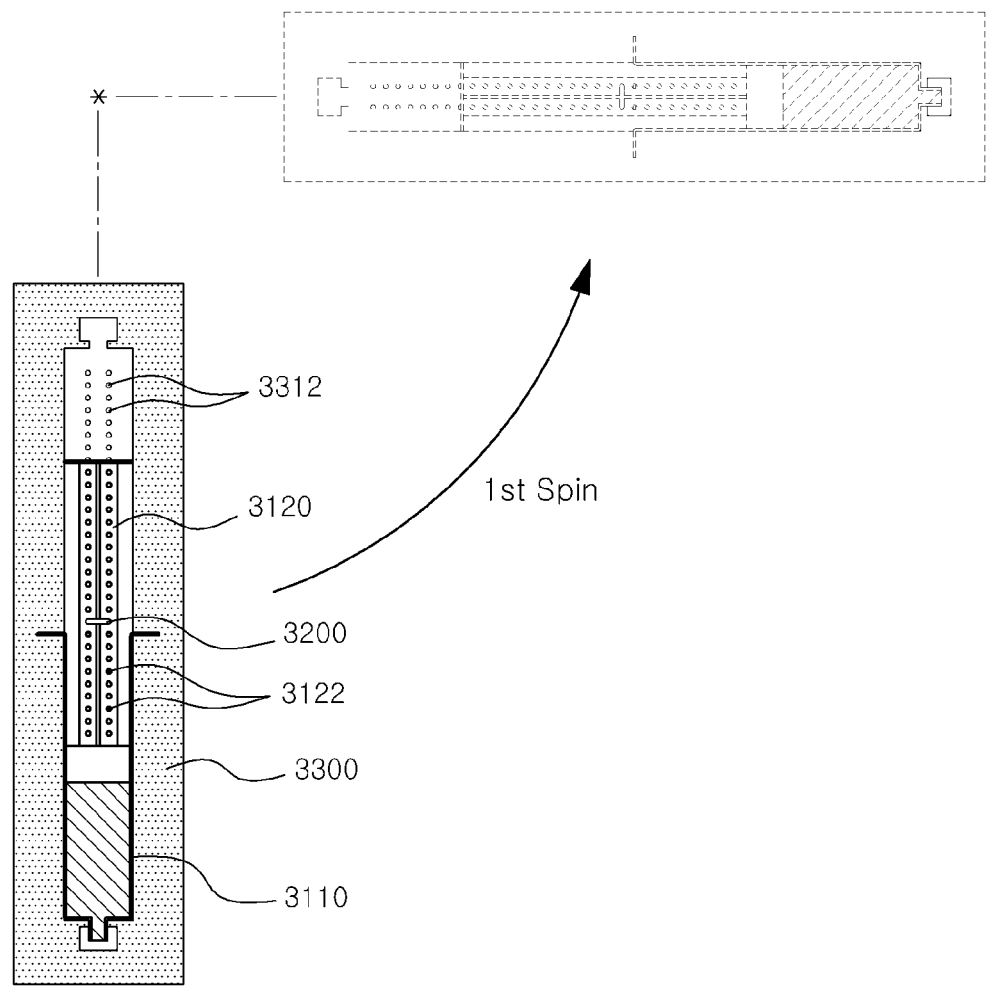

【Fig. 33】
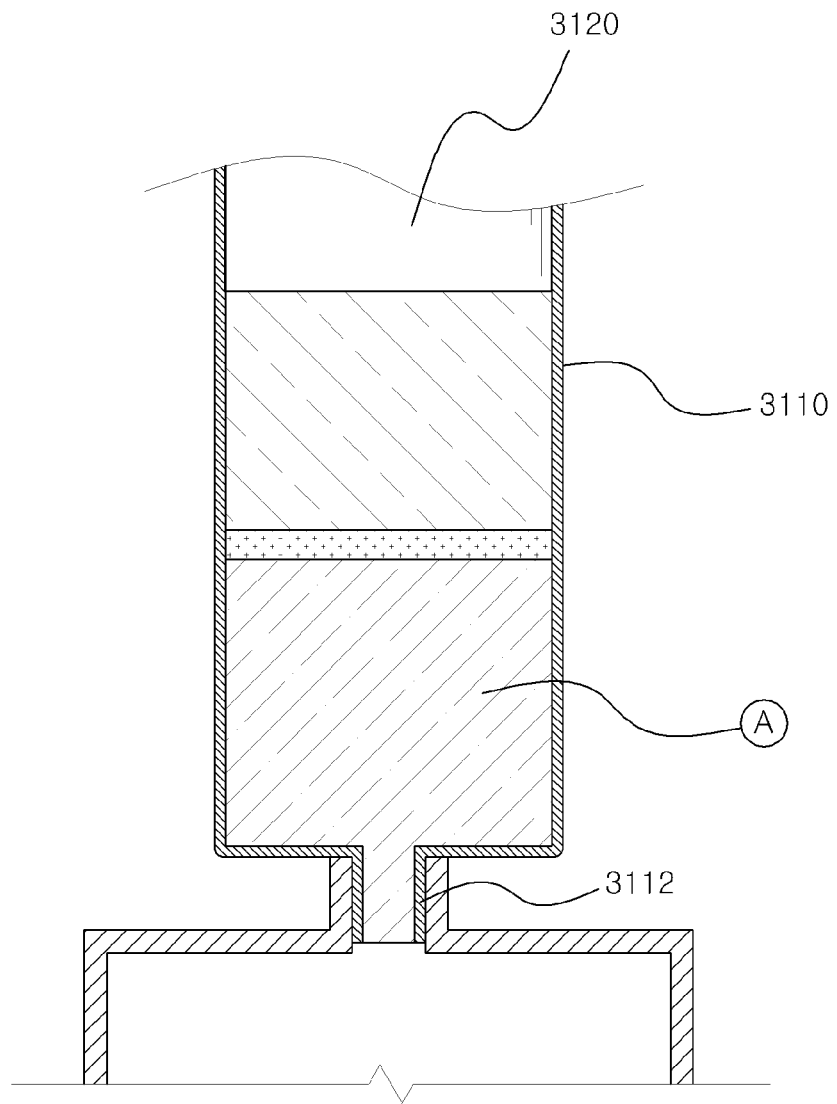

[Fig. 34]
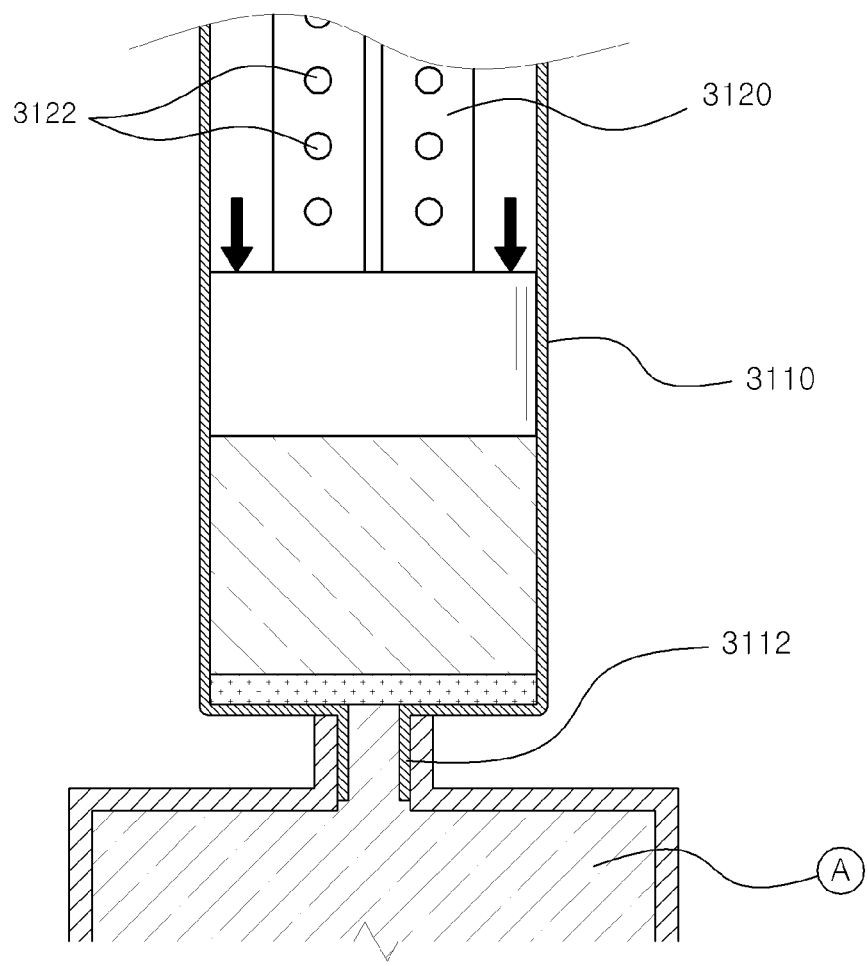

[Fig. 35]
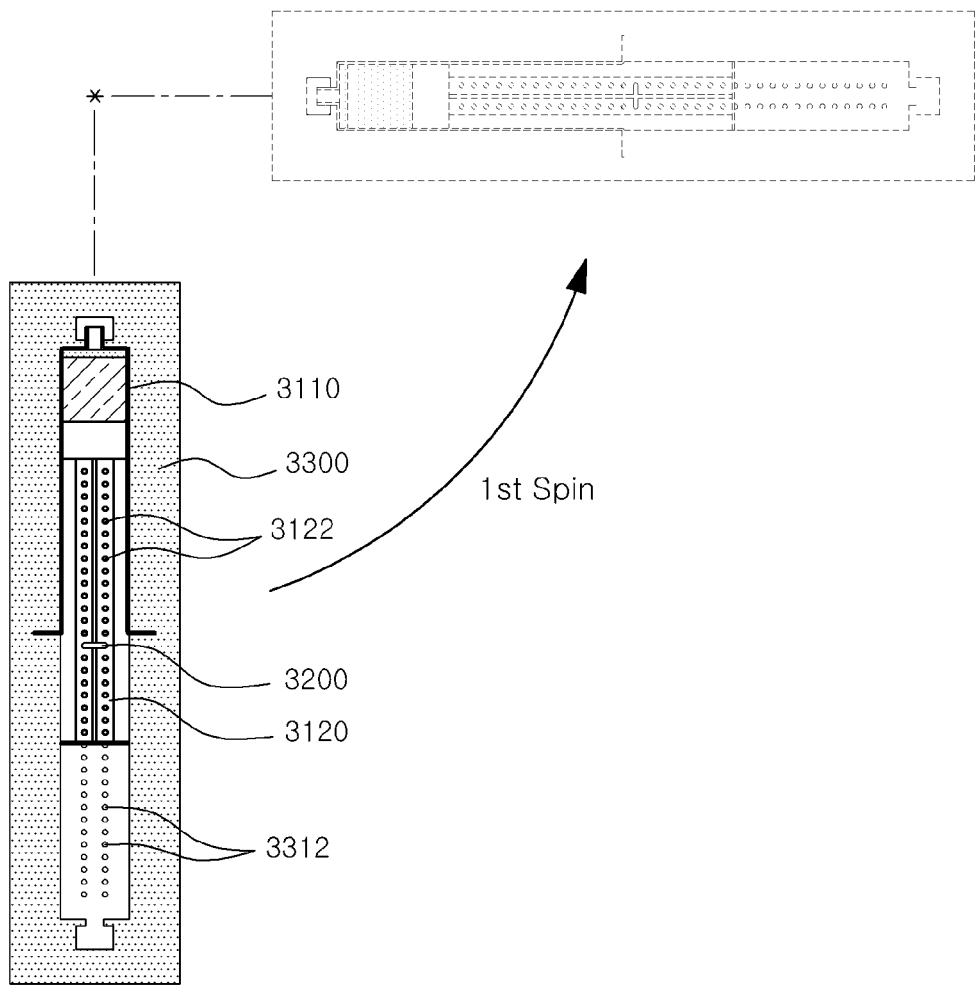

[Fig. 36]
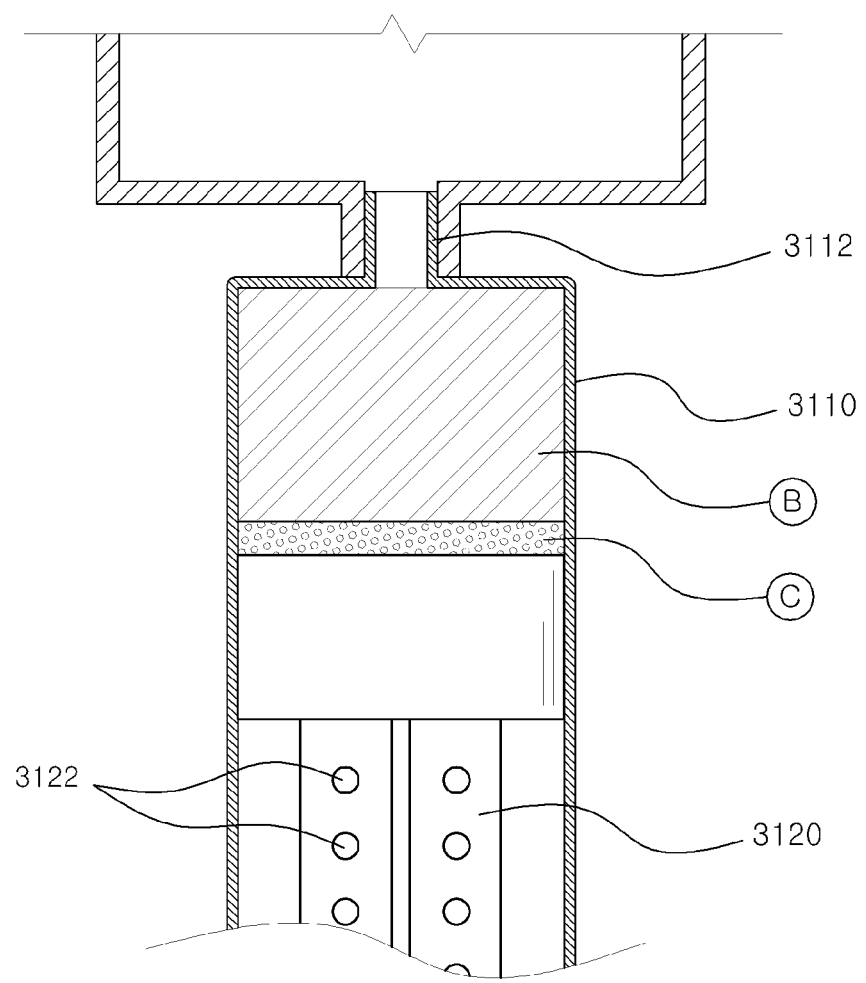

【Fig. 37】
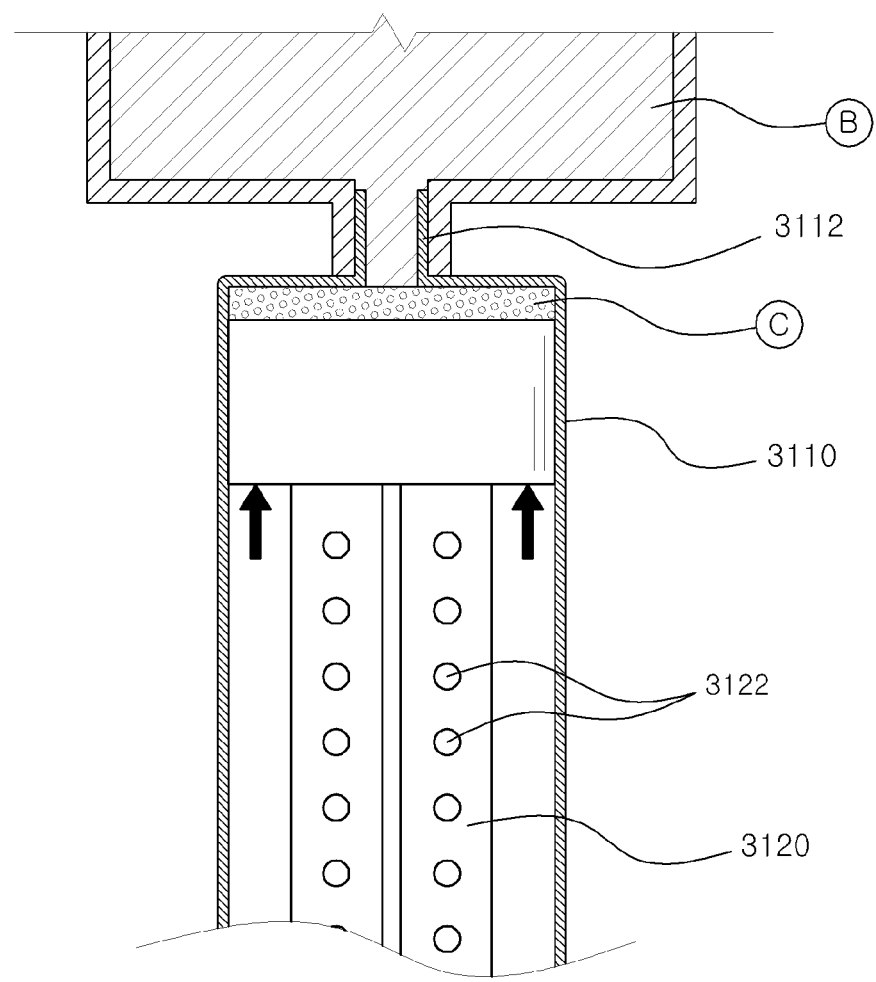

【Fig. 38】
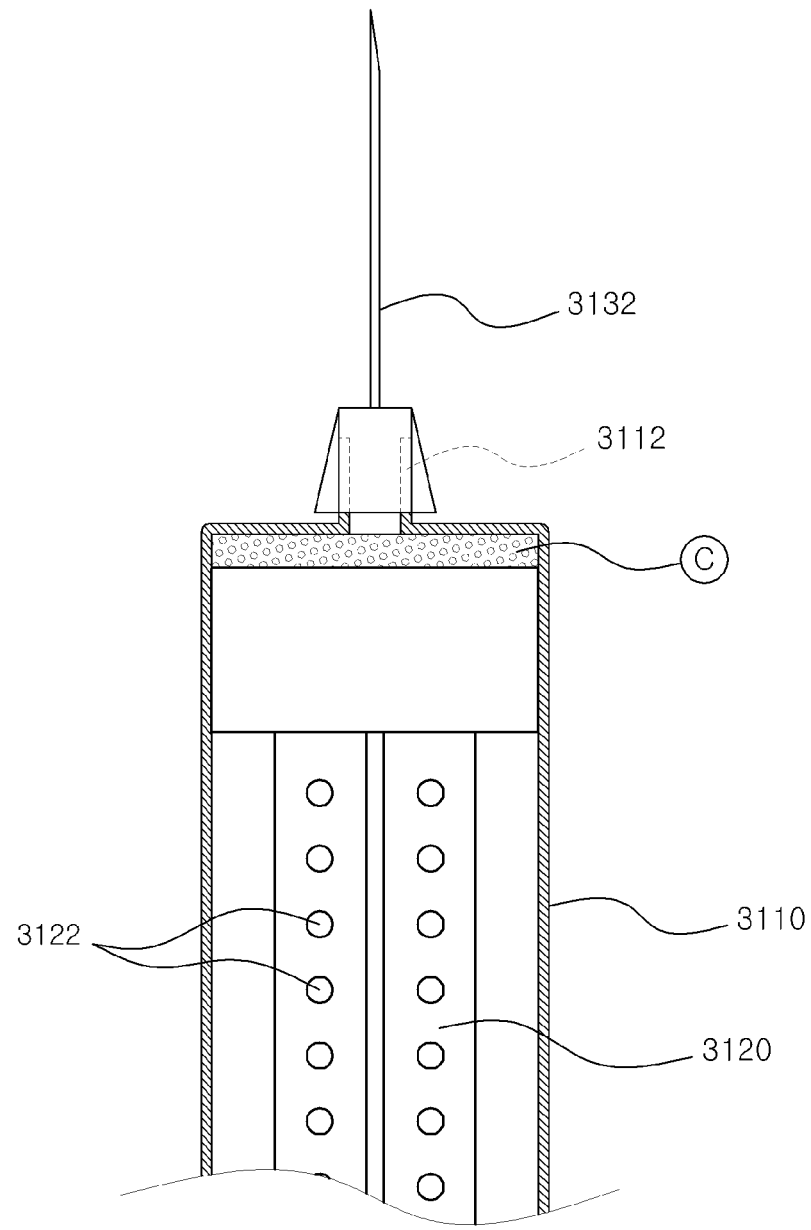

[Fig. 39]
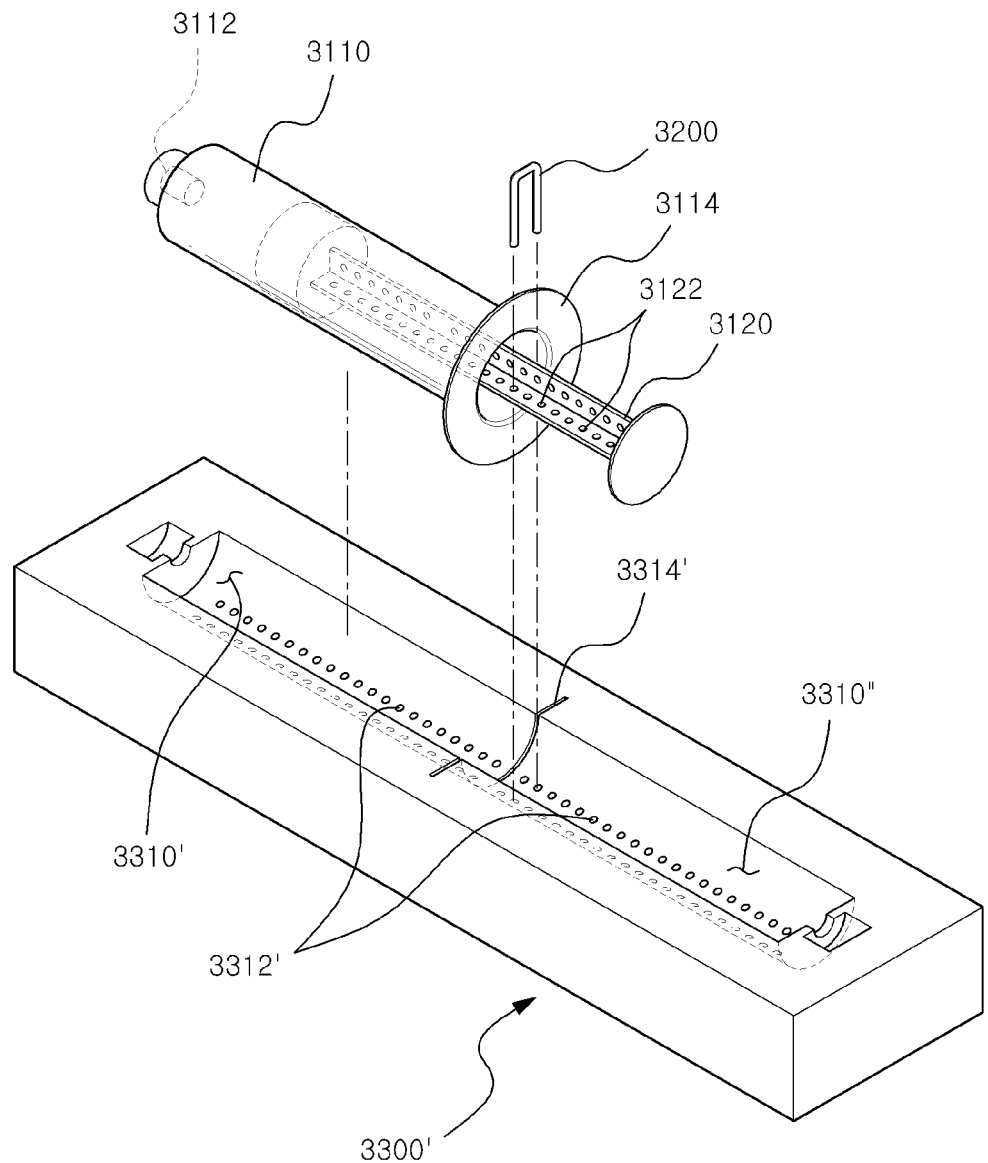

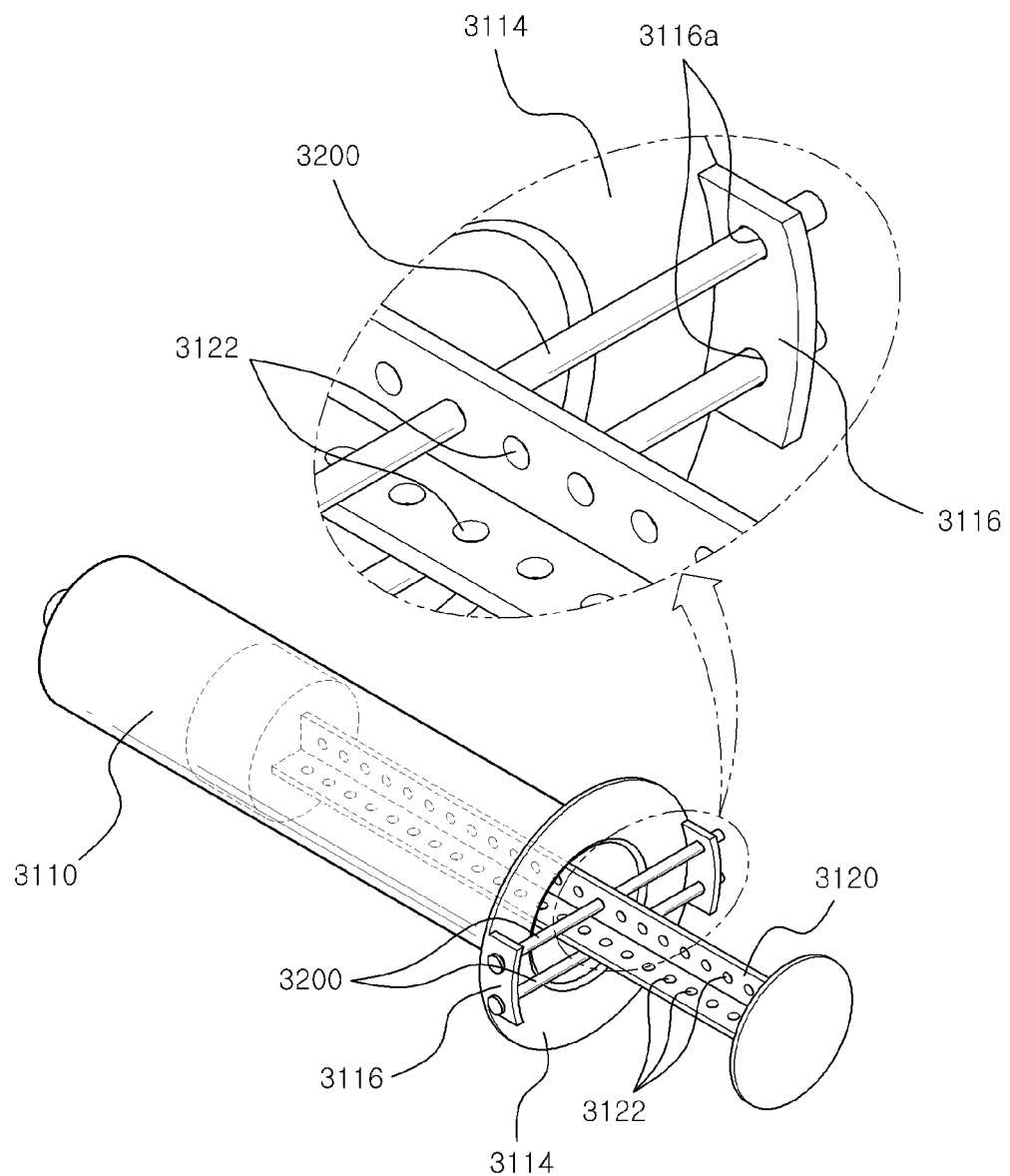
[Fig. 40]

[Fig. 41]
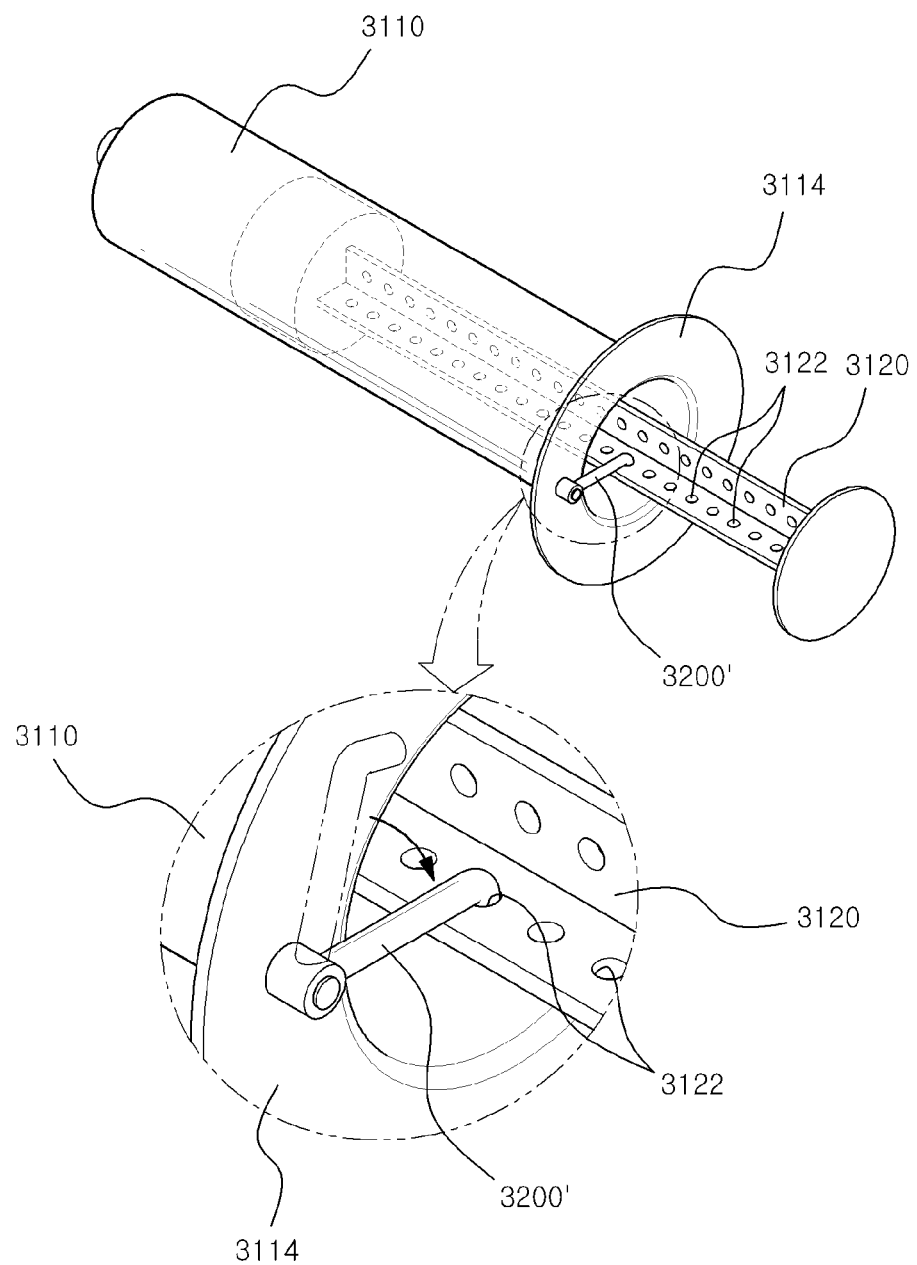

[Fig. 42]
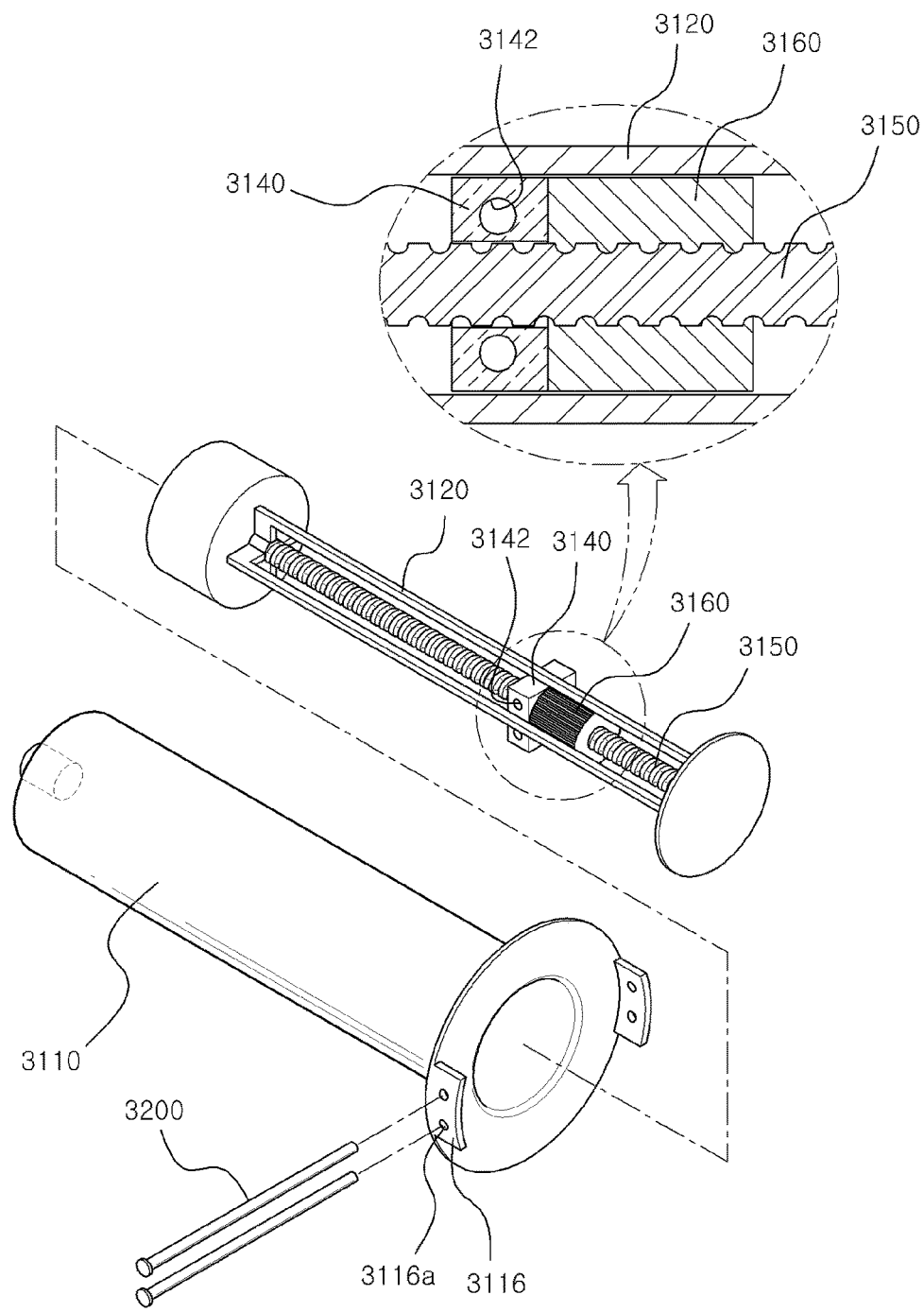

[Fig. 43]
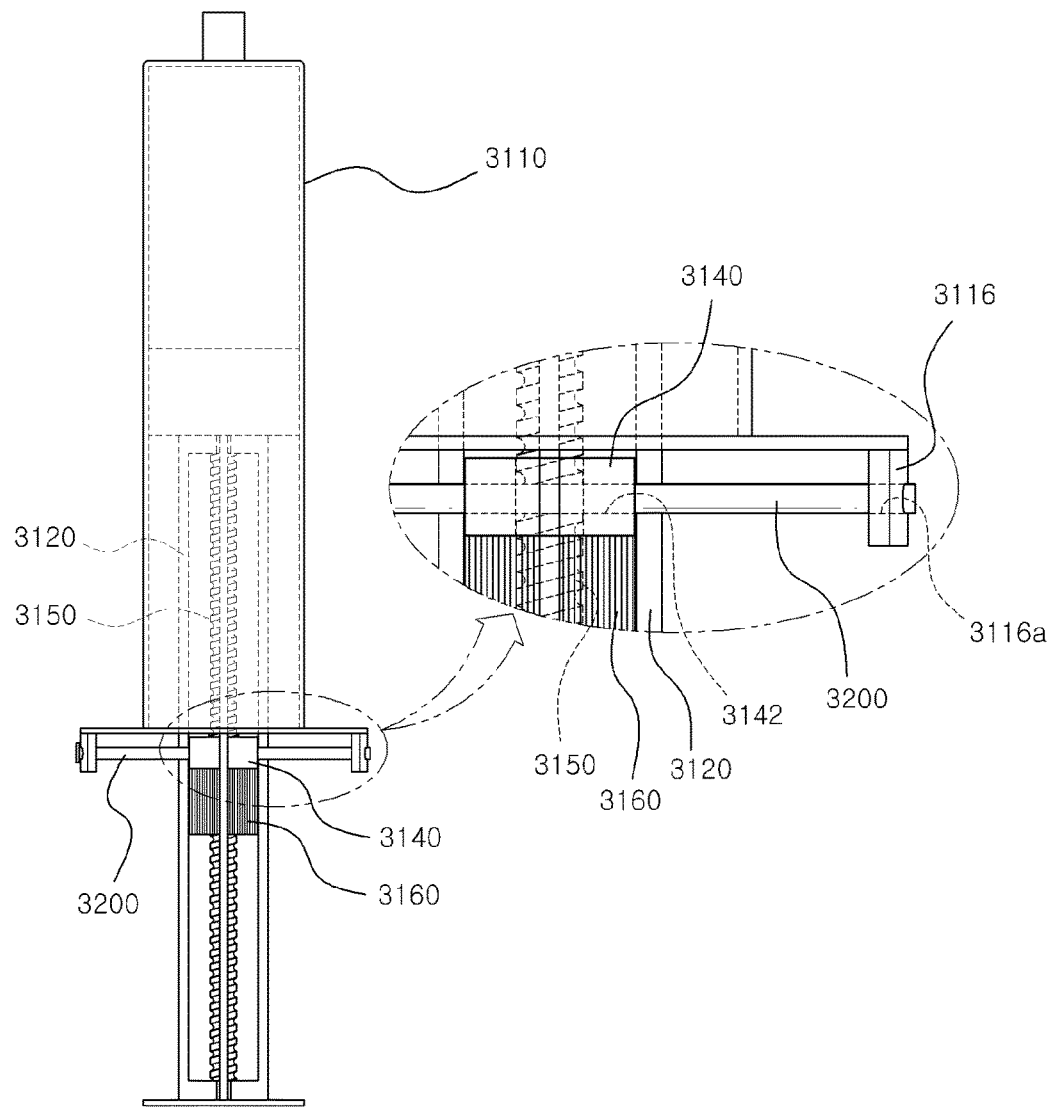

[Fig. 44]
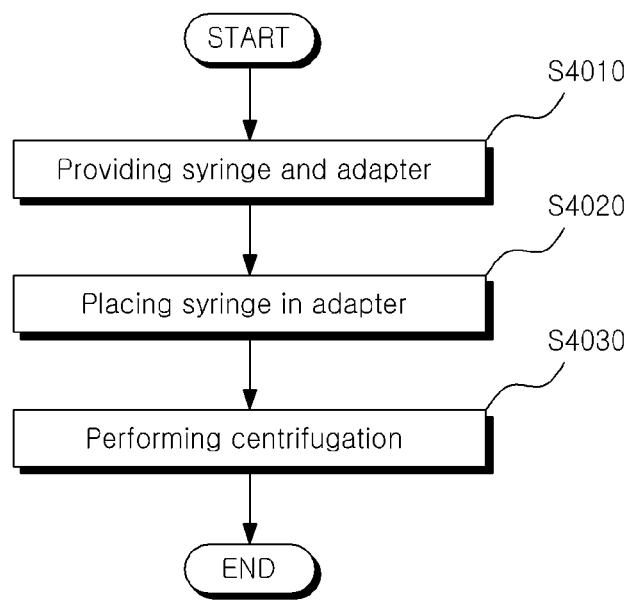

[Fig. 45]
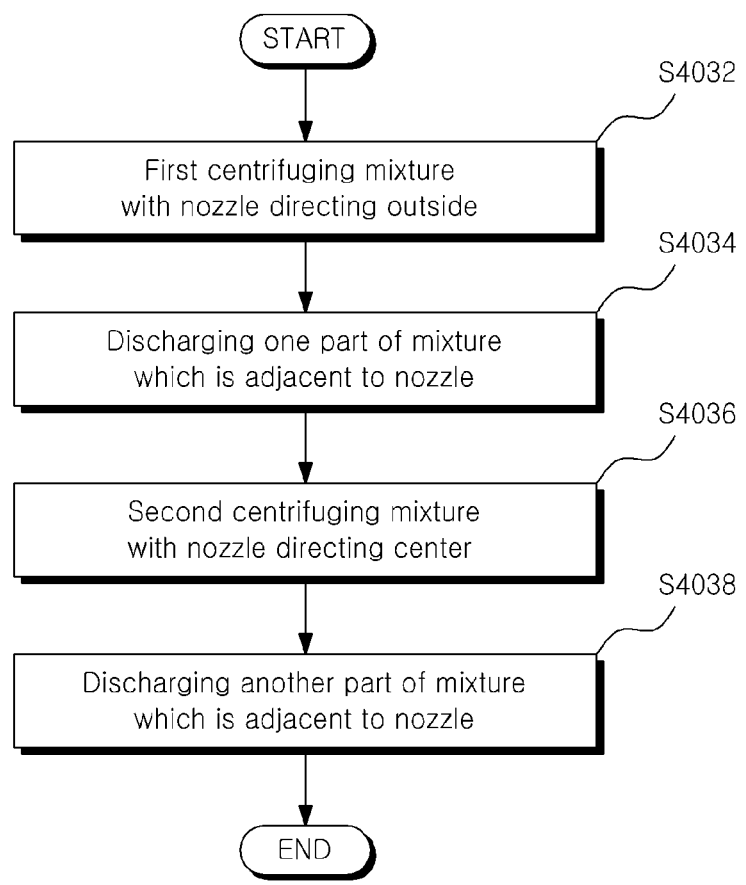

[Fig. 46]
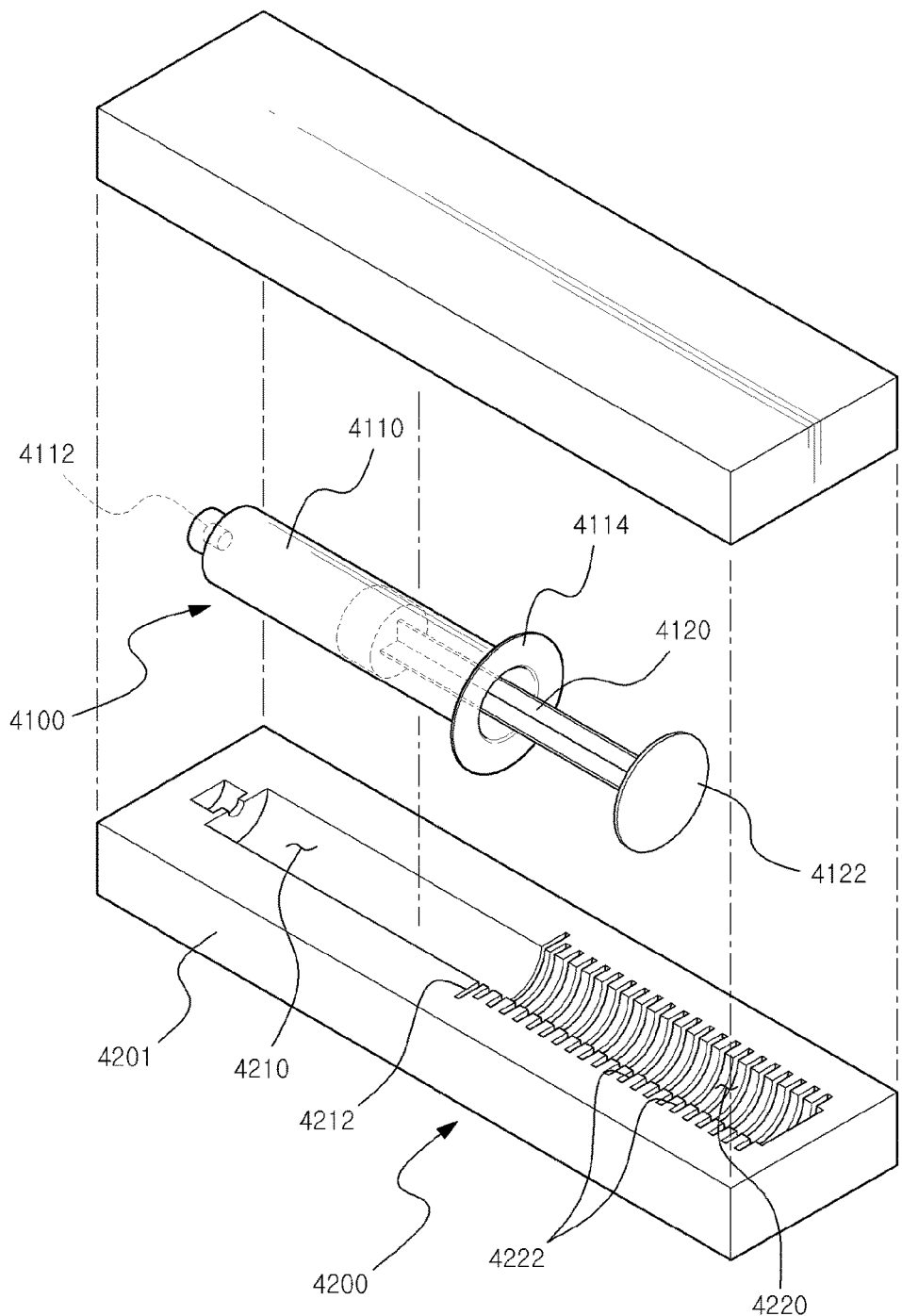

[Fig. 47]
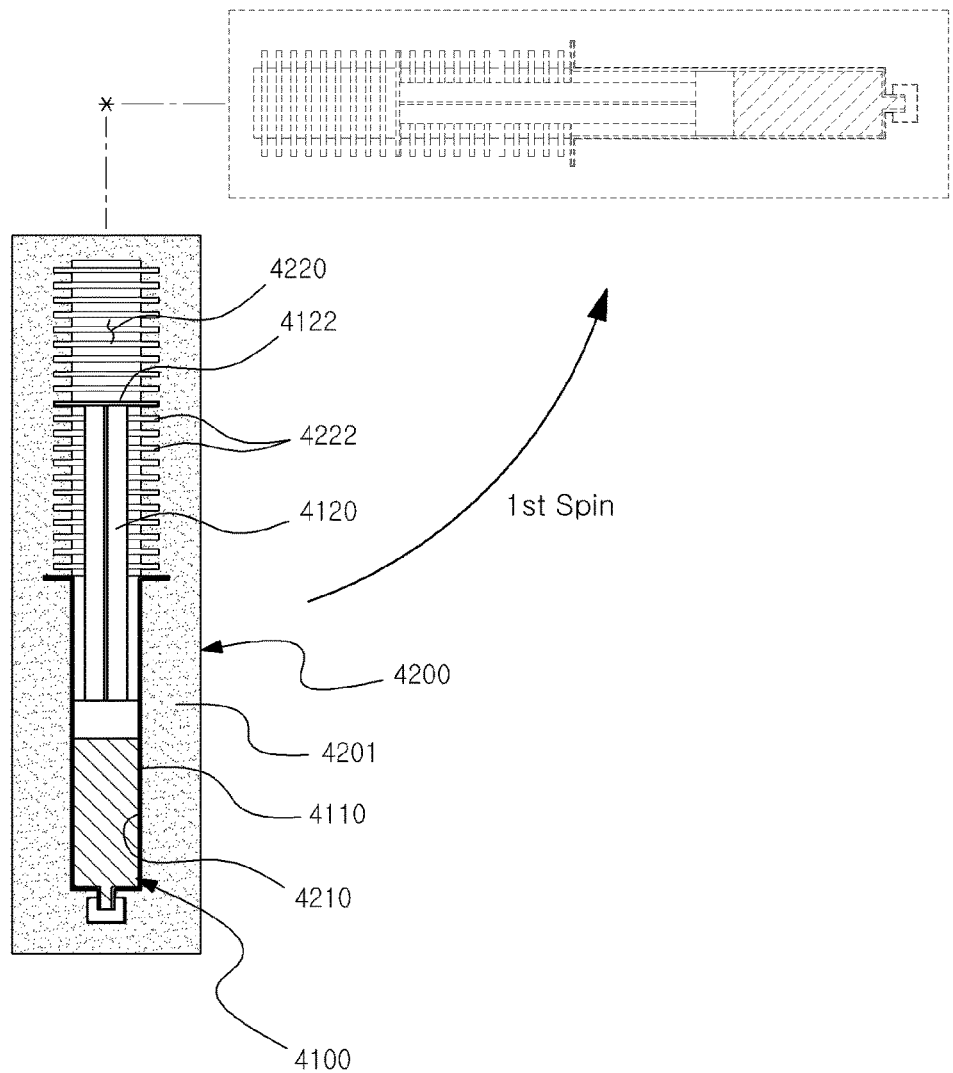

【Fig. 48】
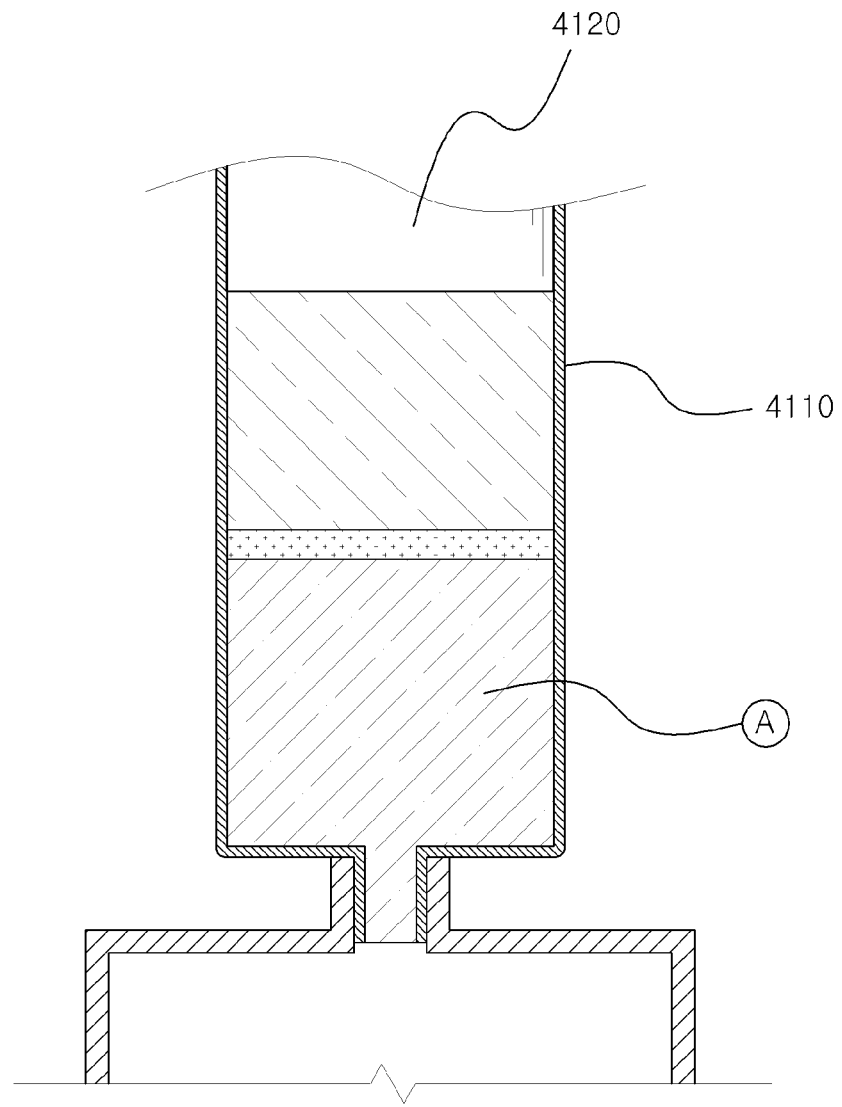

[Fig. 49]
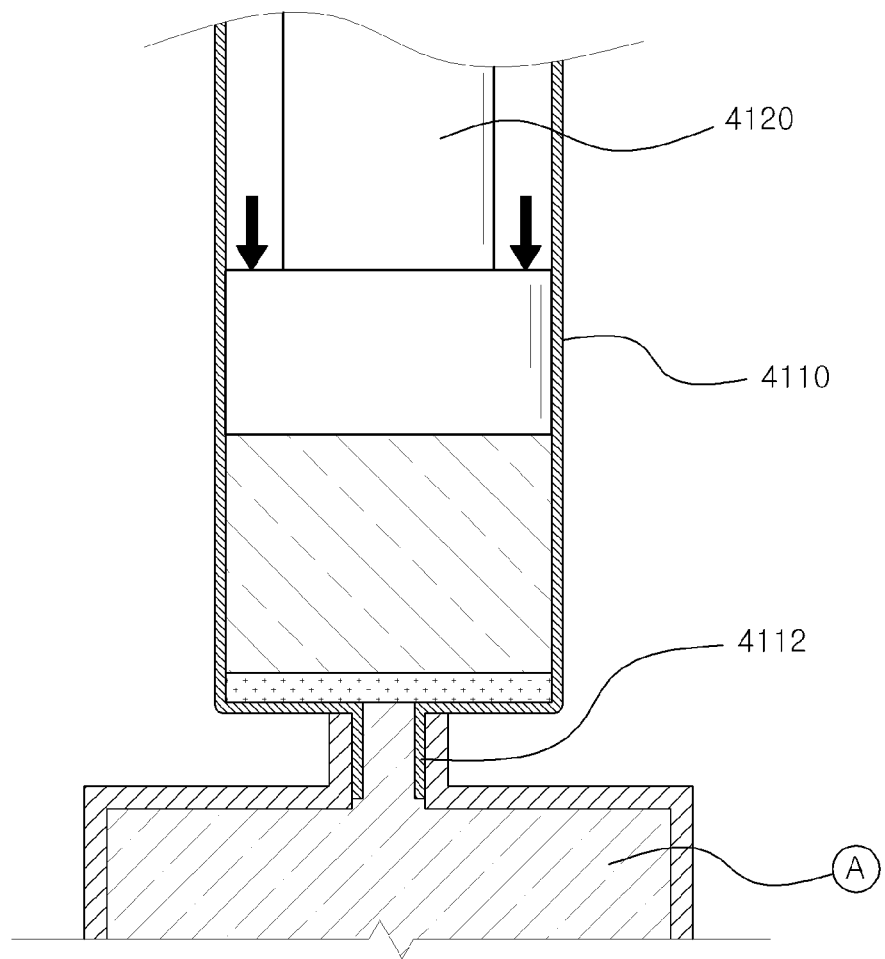

[Fig. 50]
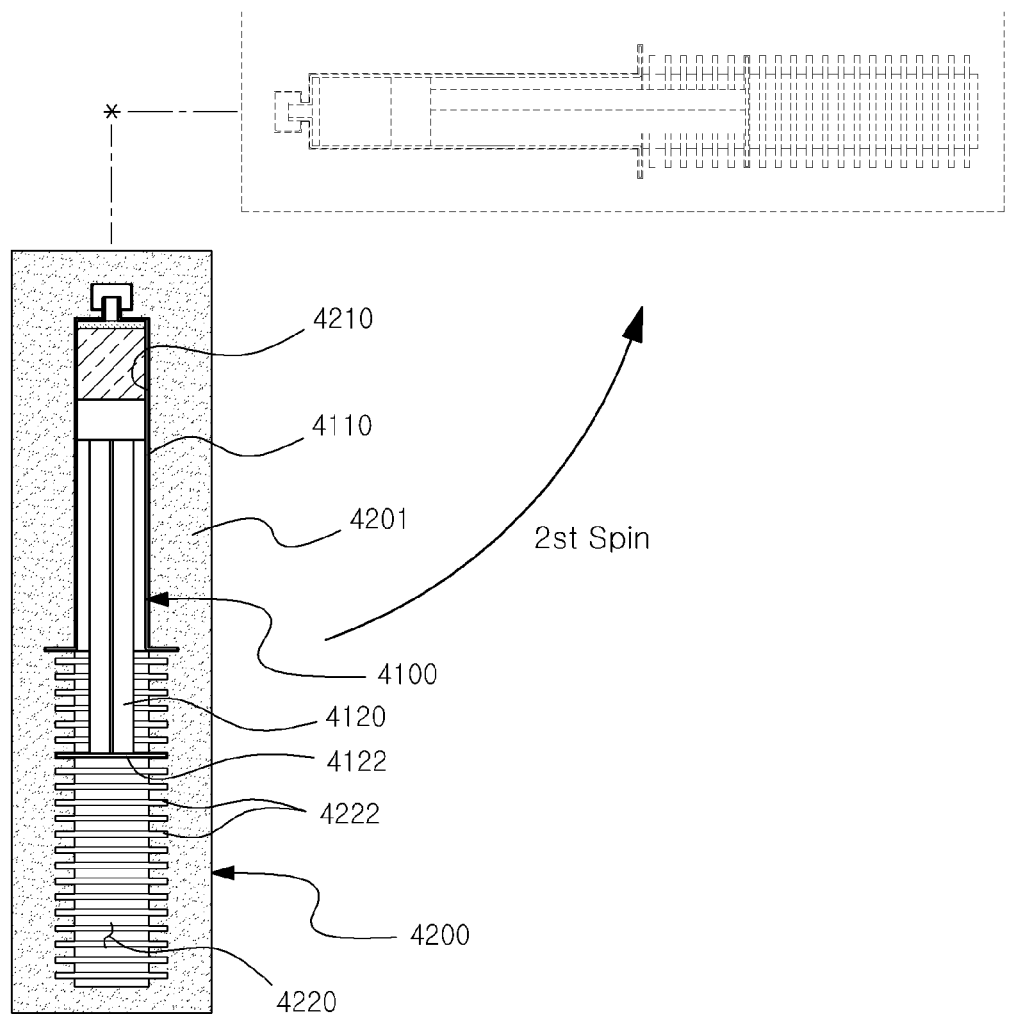

[Fig. 51]
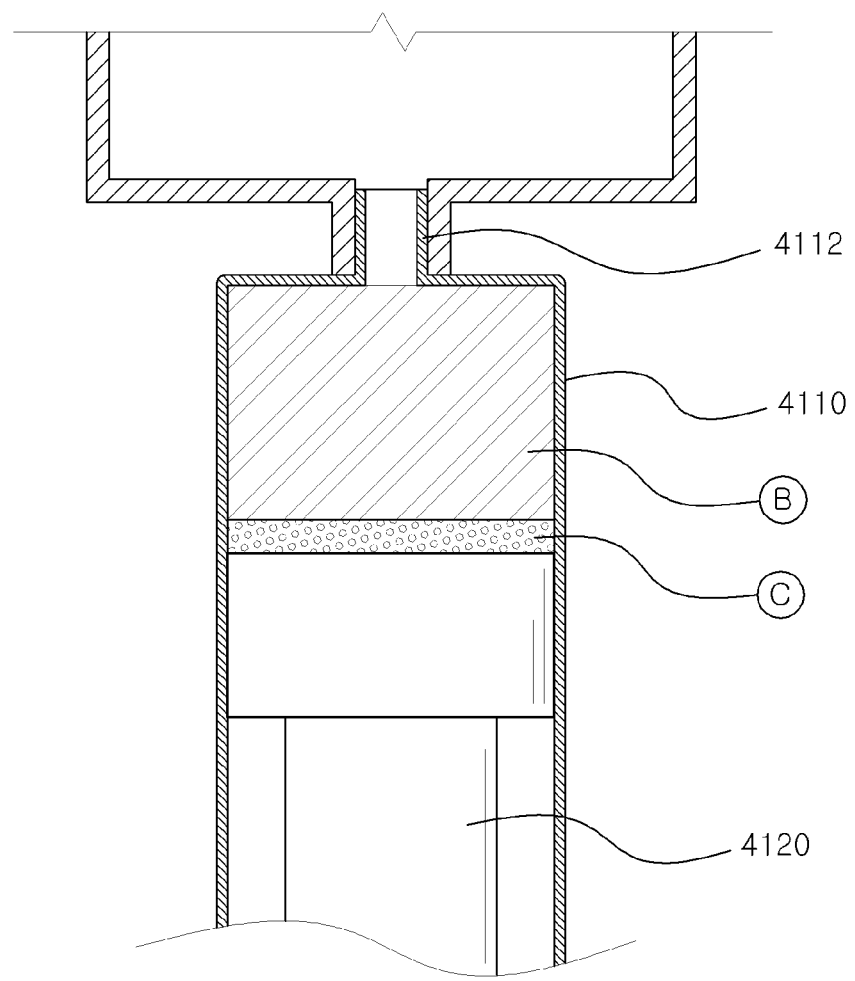

【Fig. 52】
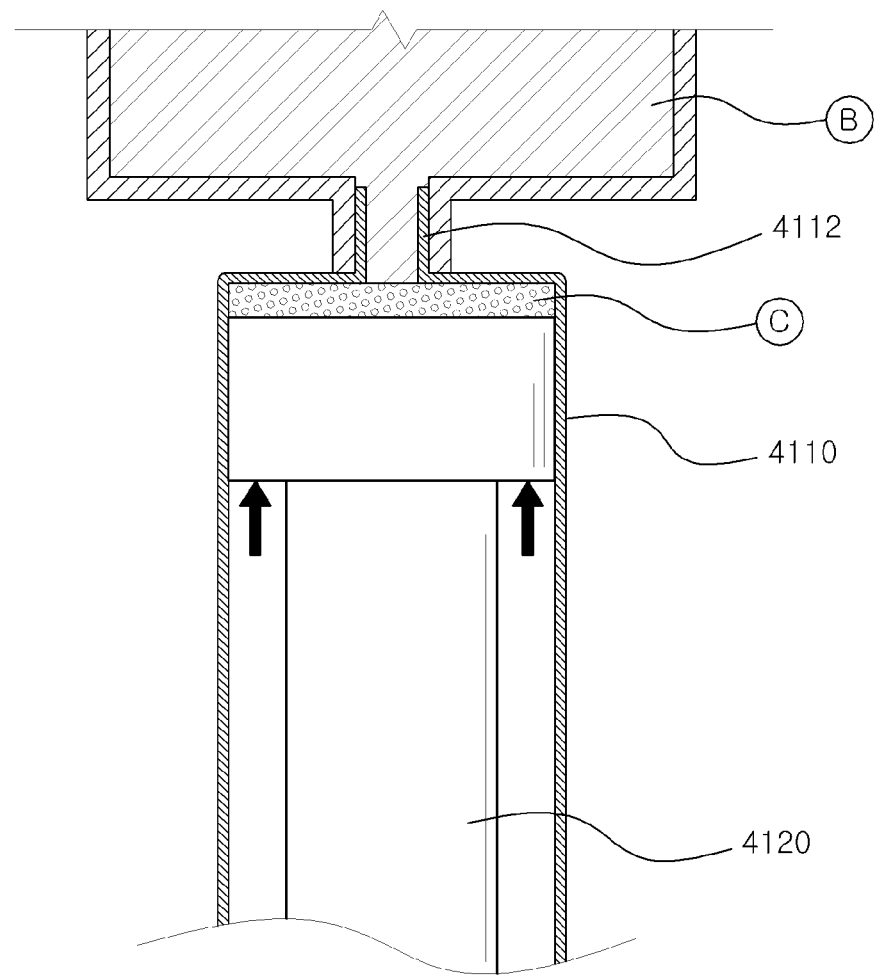

【Fig. 53】
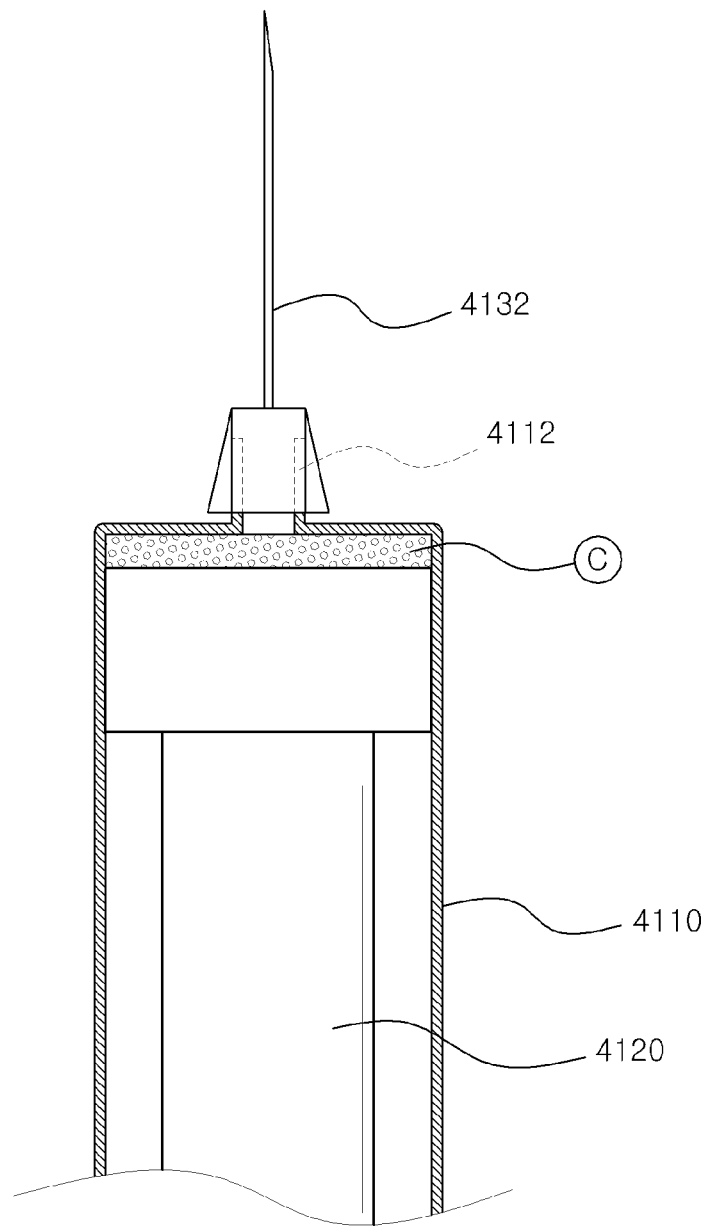

[Fig. 54]
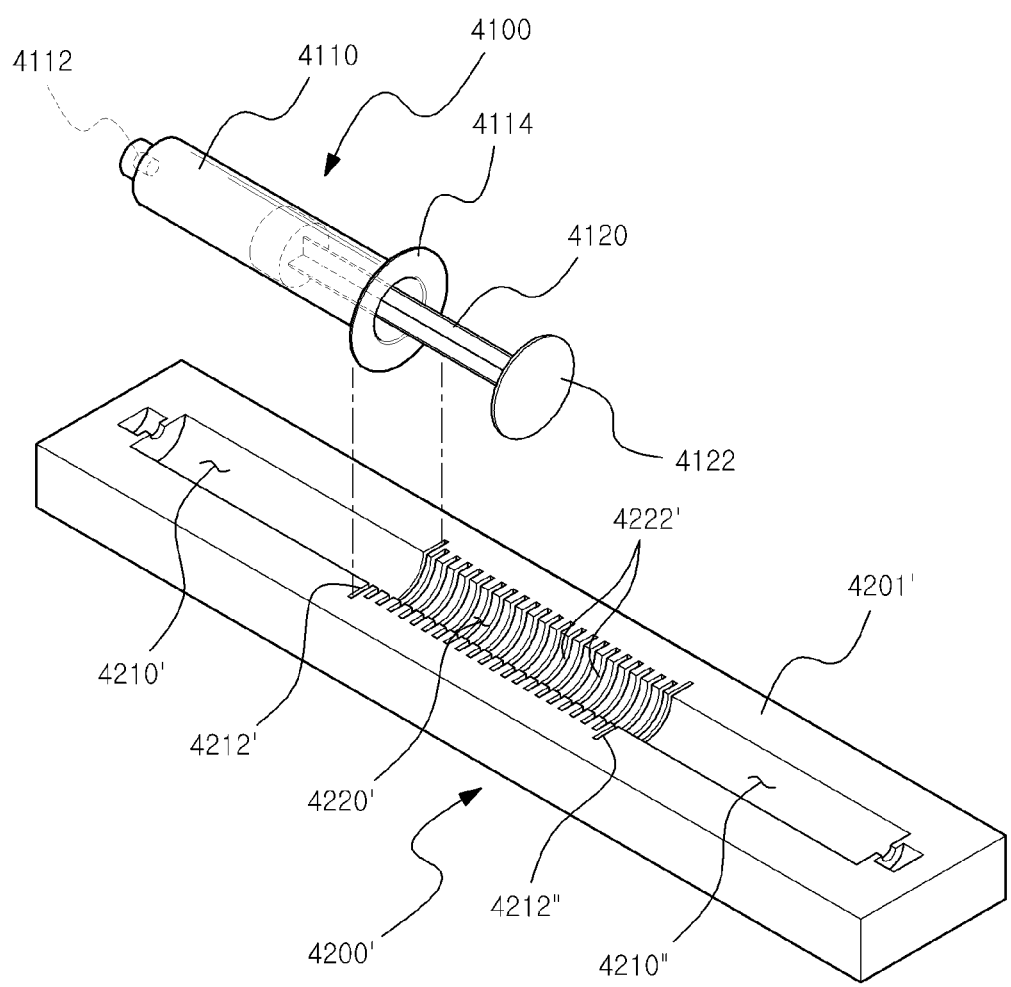

[Fig. 55]
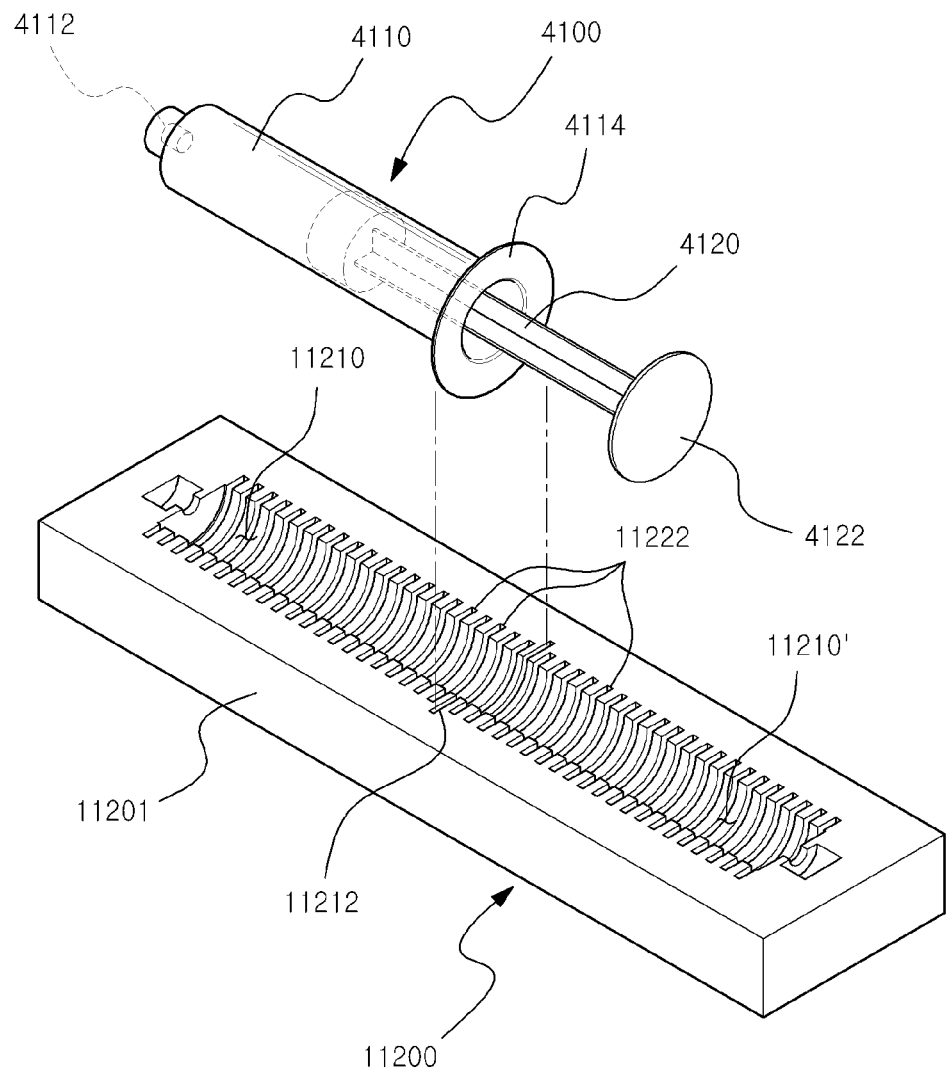

[Fig. 56]
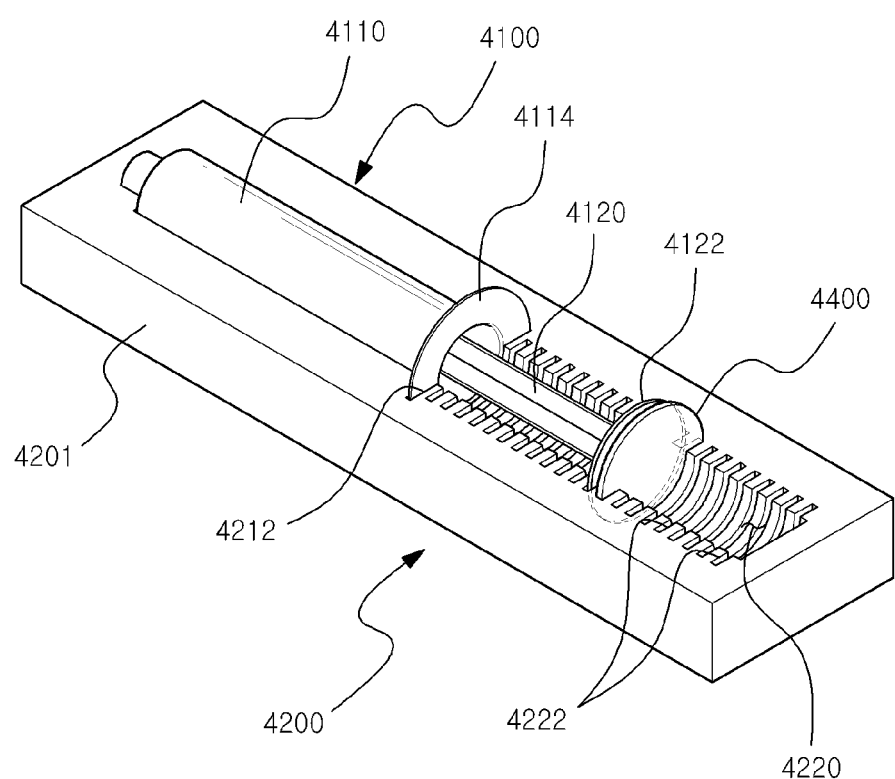

【Fig. 57】
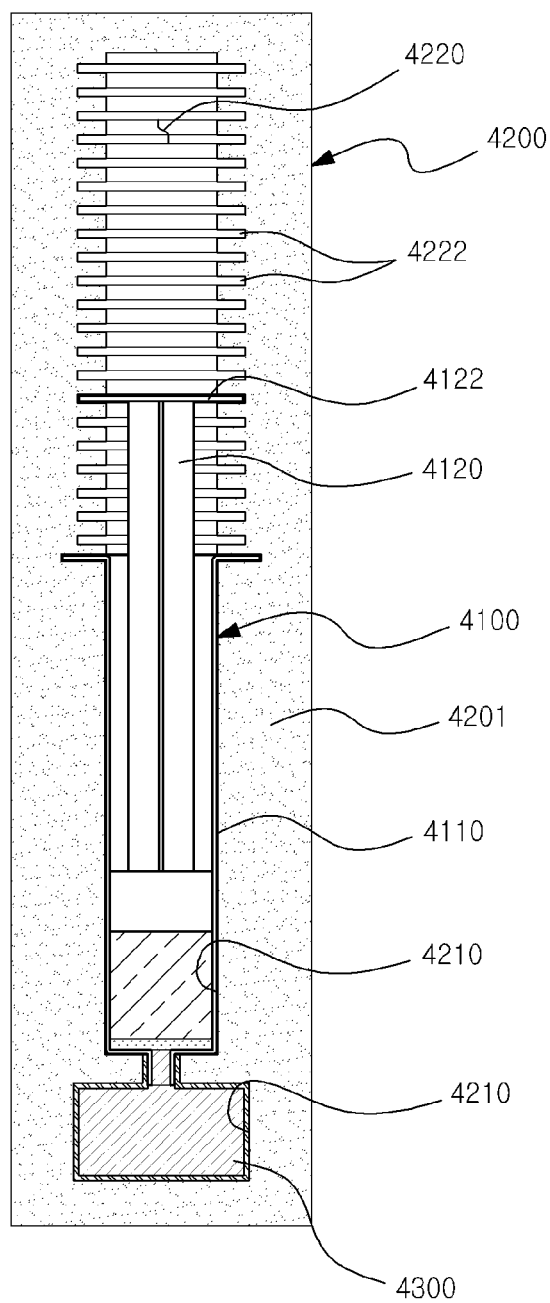

[Fig. 58]
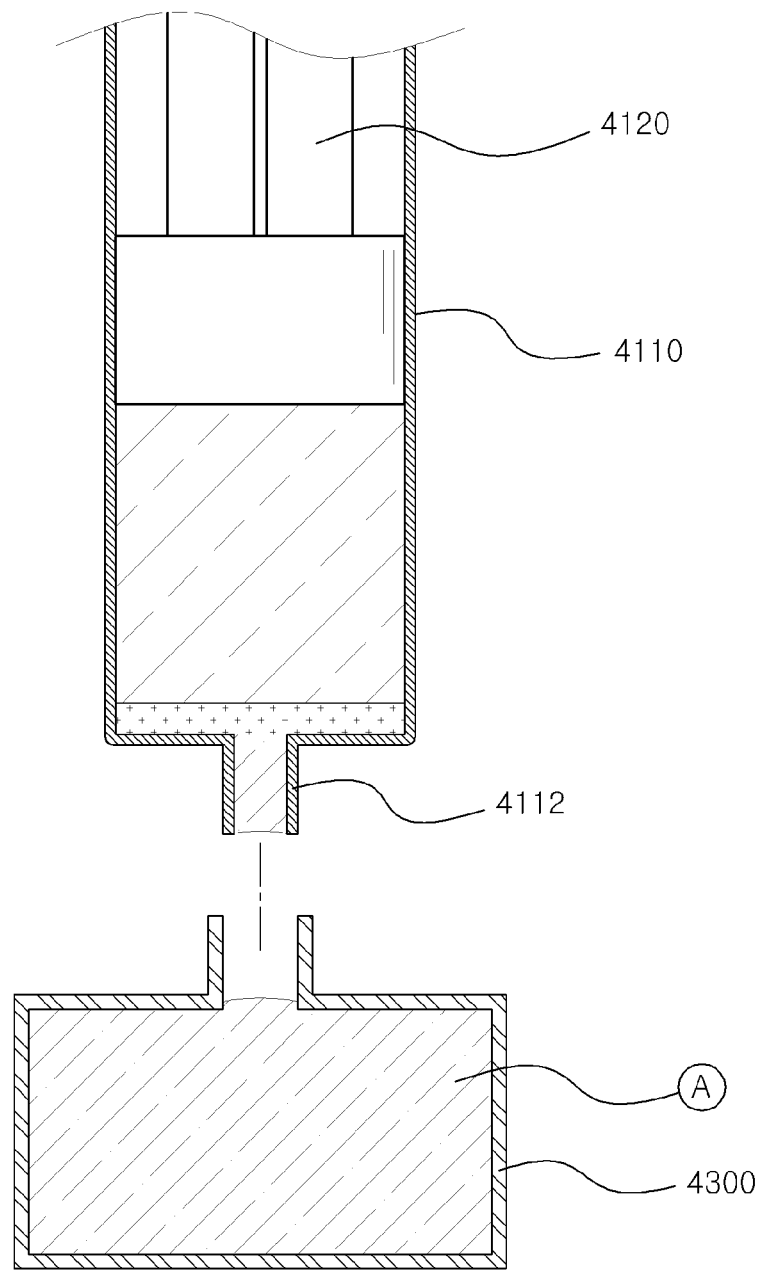

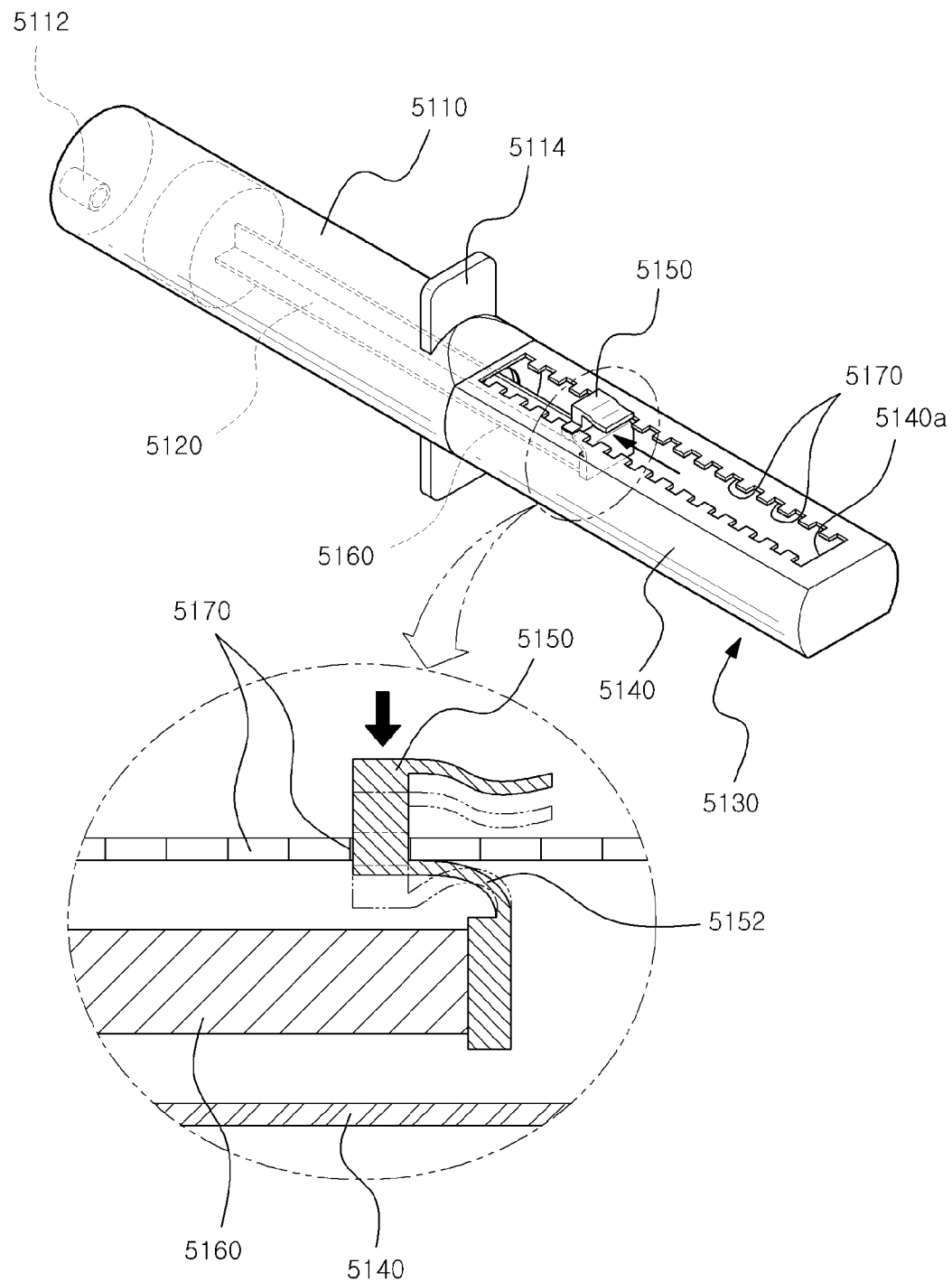
[Fig. 59]

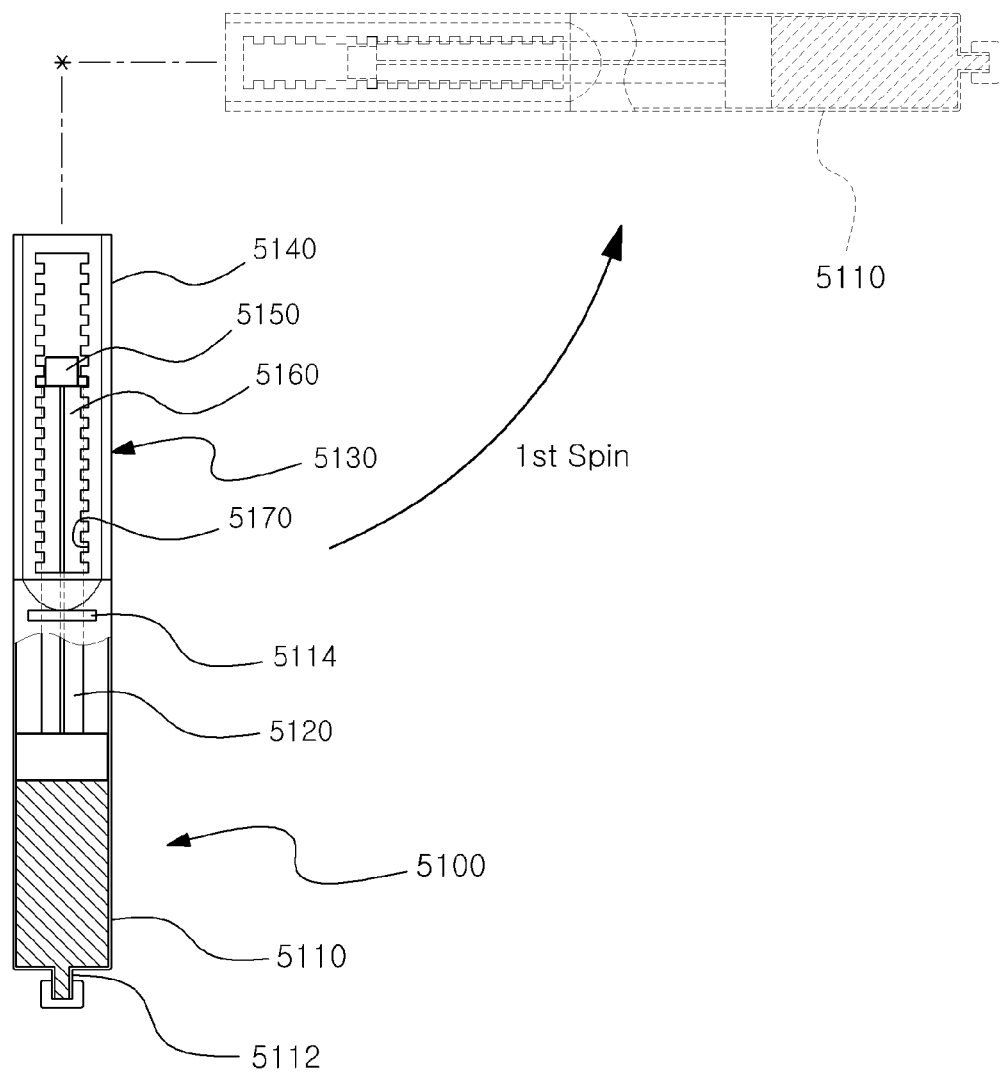
[Fig. 60]

[Fig. 61]
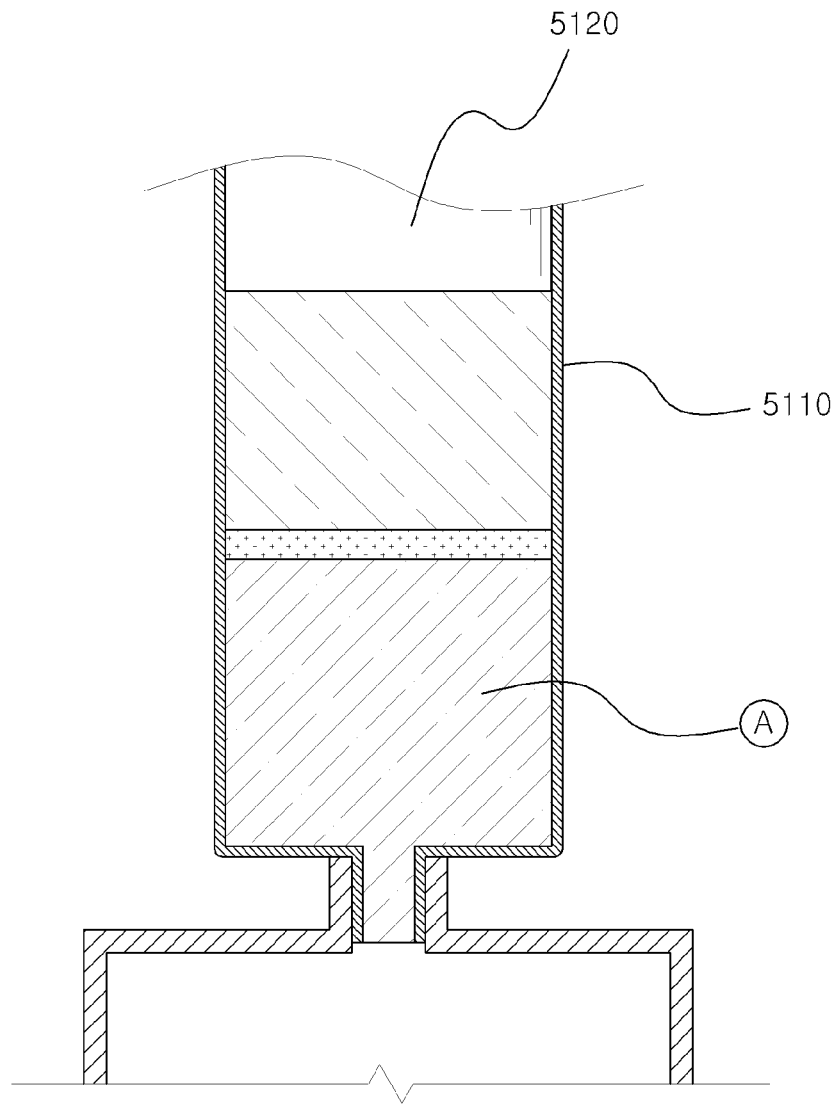

[Fig. 62]
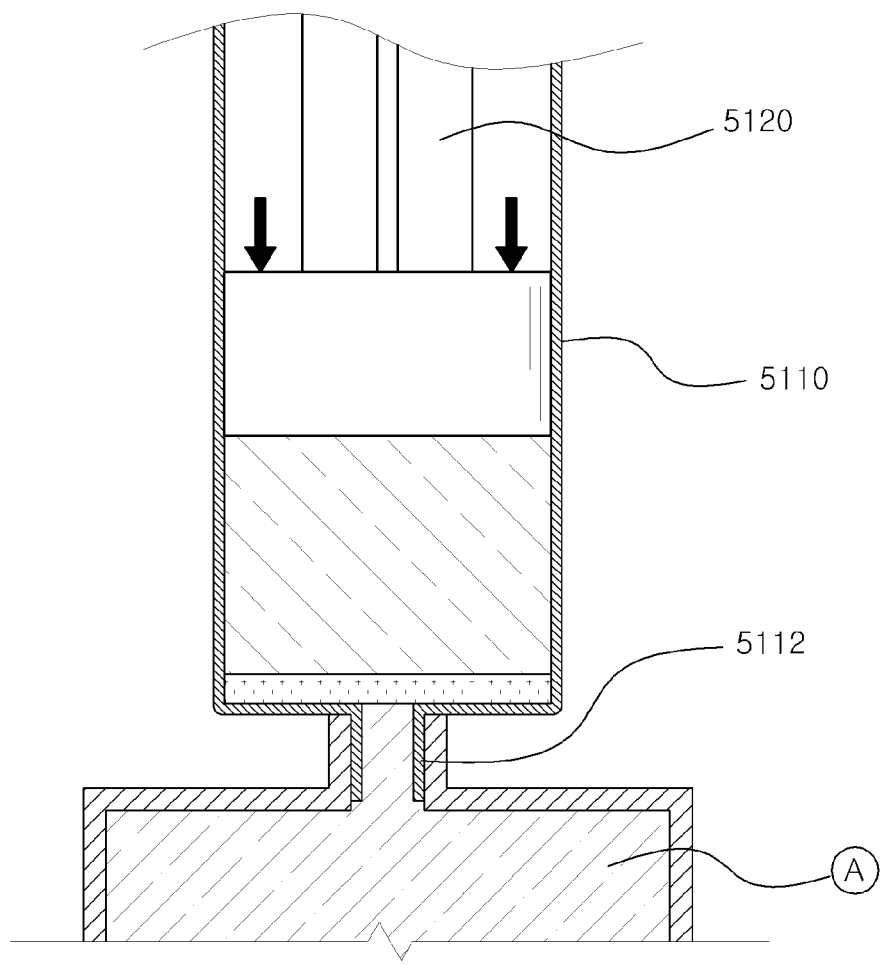

[Fig. 63]
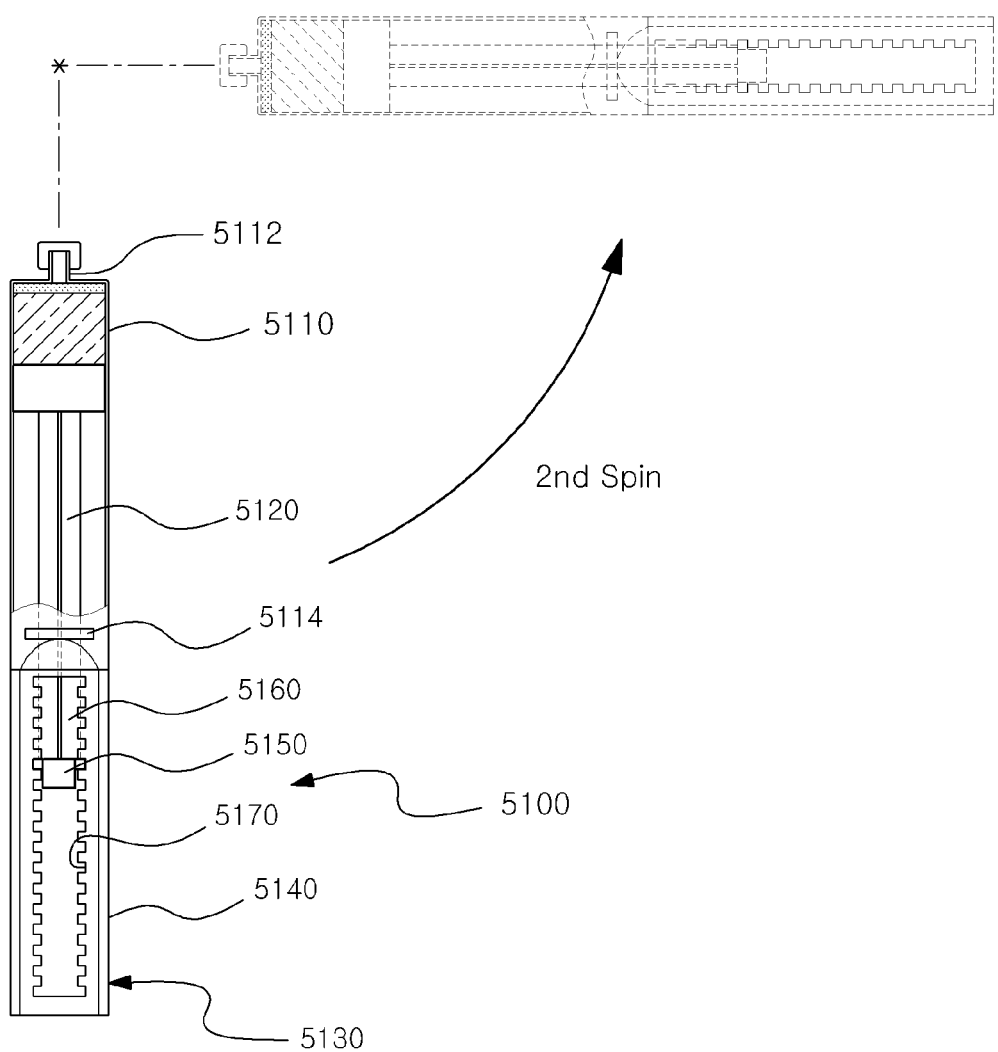

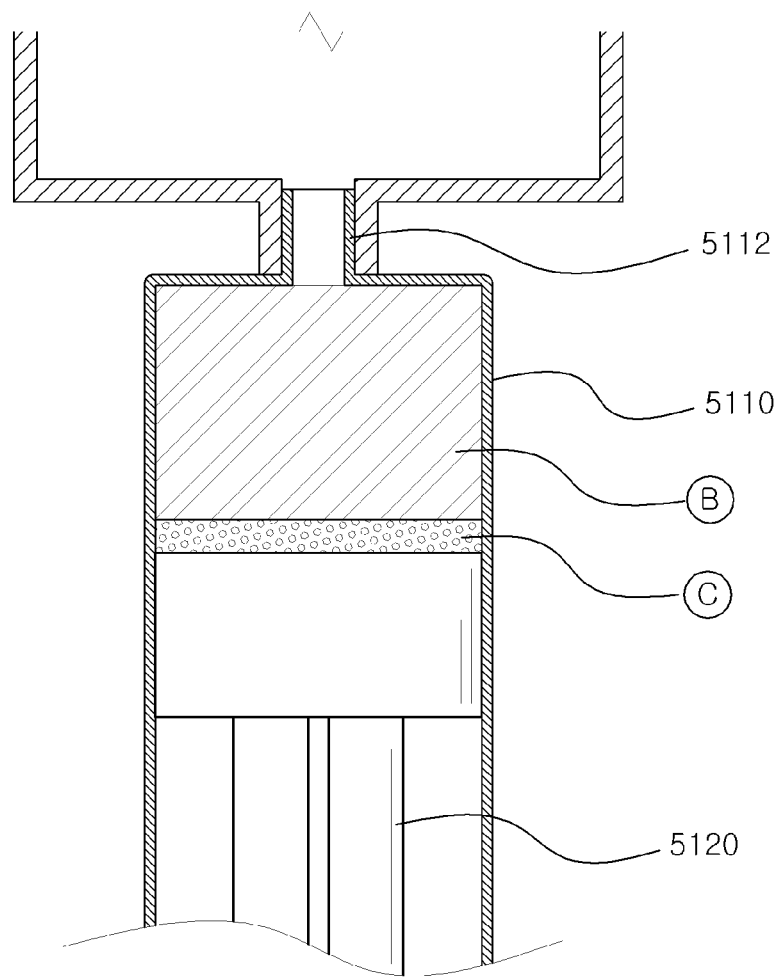
[Fig. 64]

[Fig. 65]
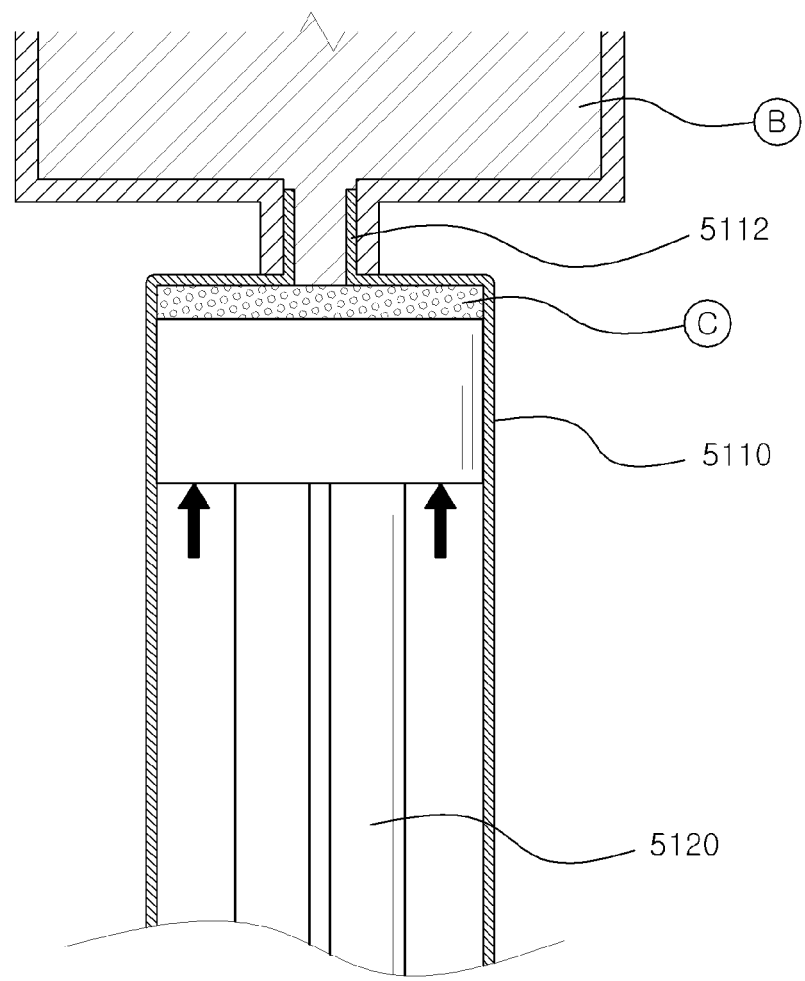

[Fig. 66]
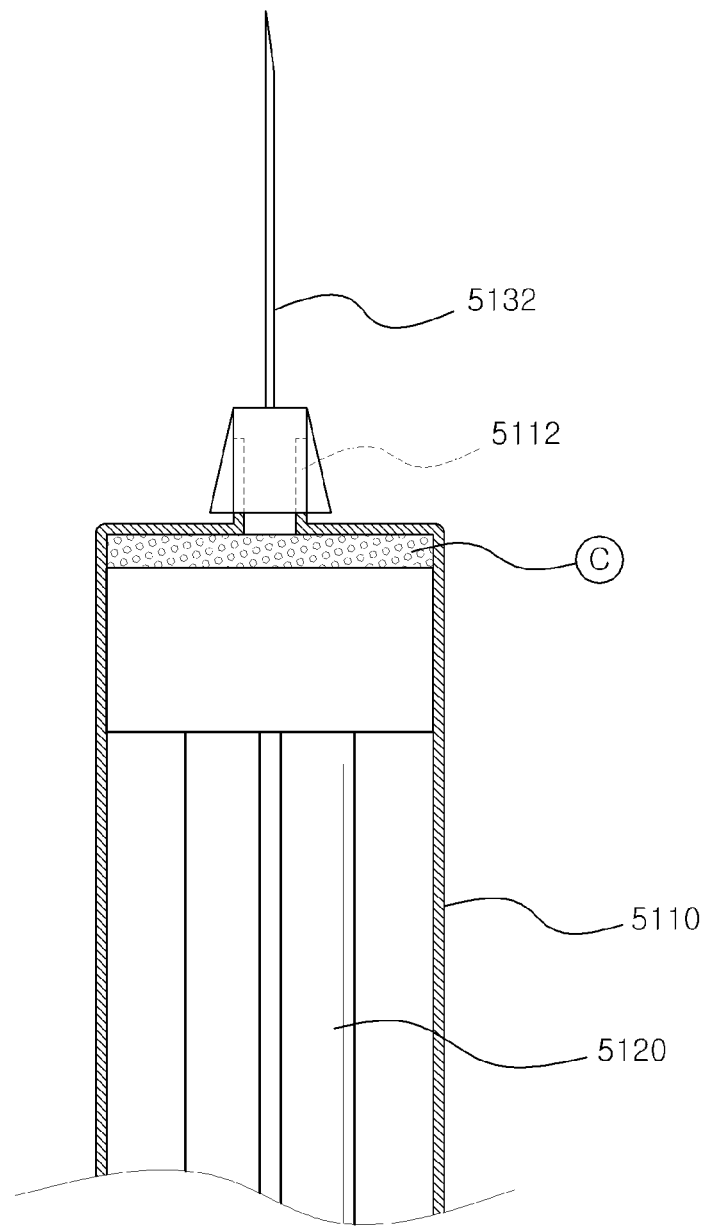

[Fig. 67]
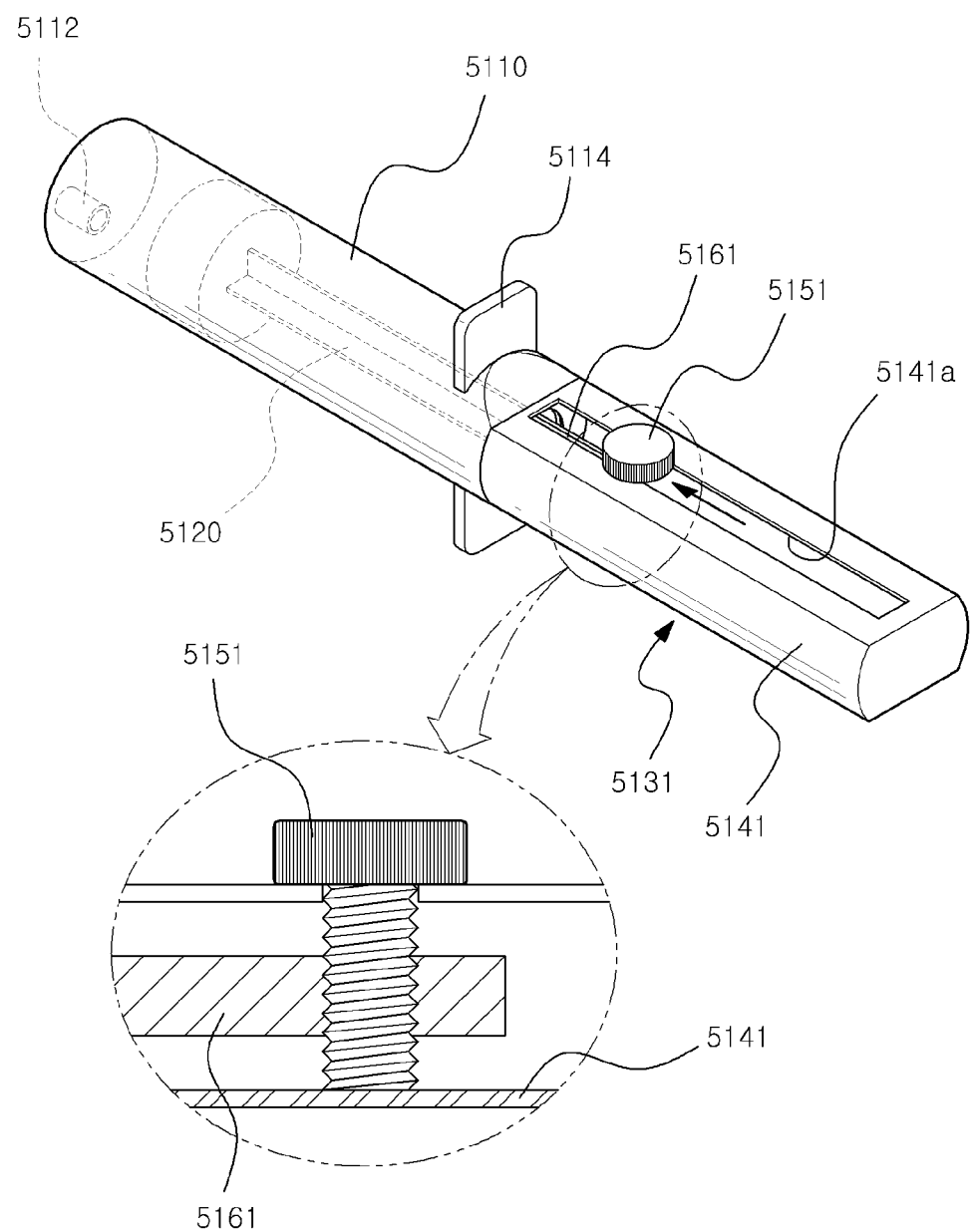

[Fig. 68]
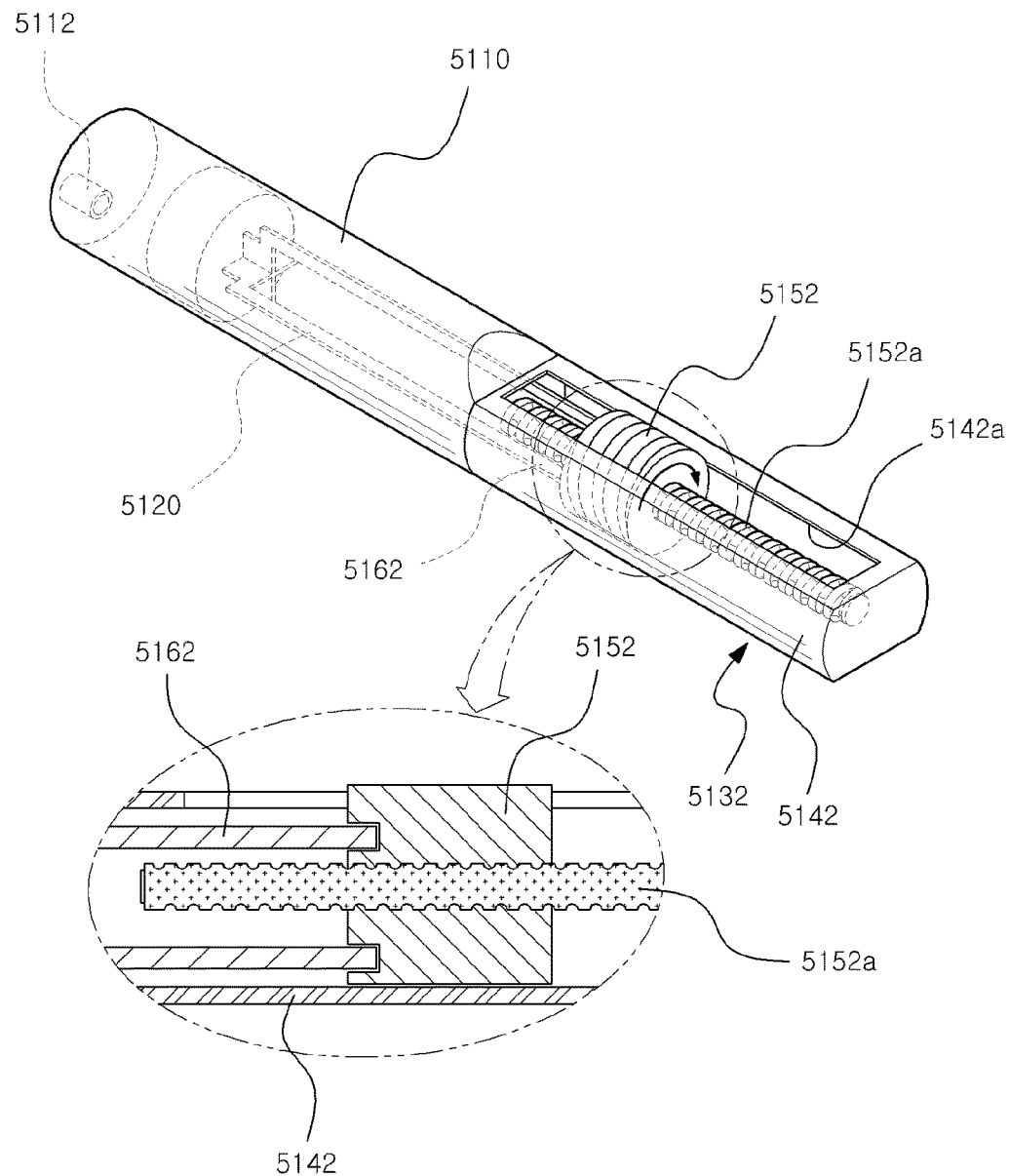

[Fig. 69]
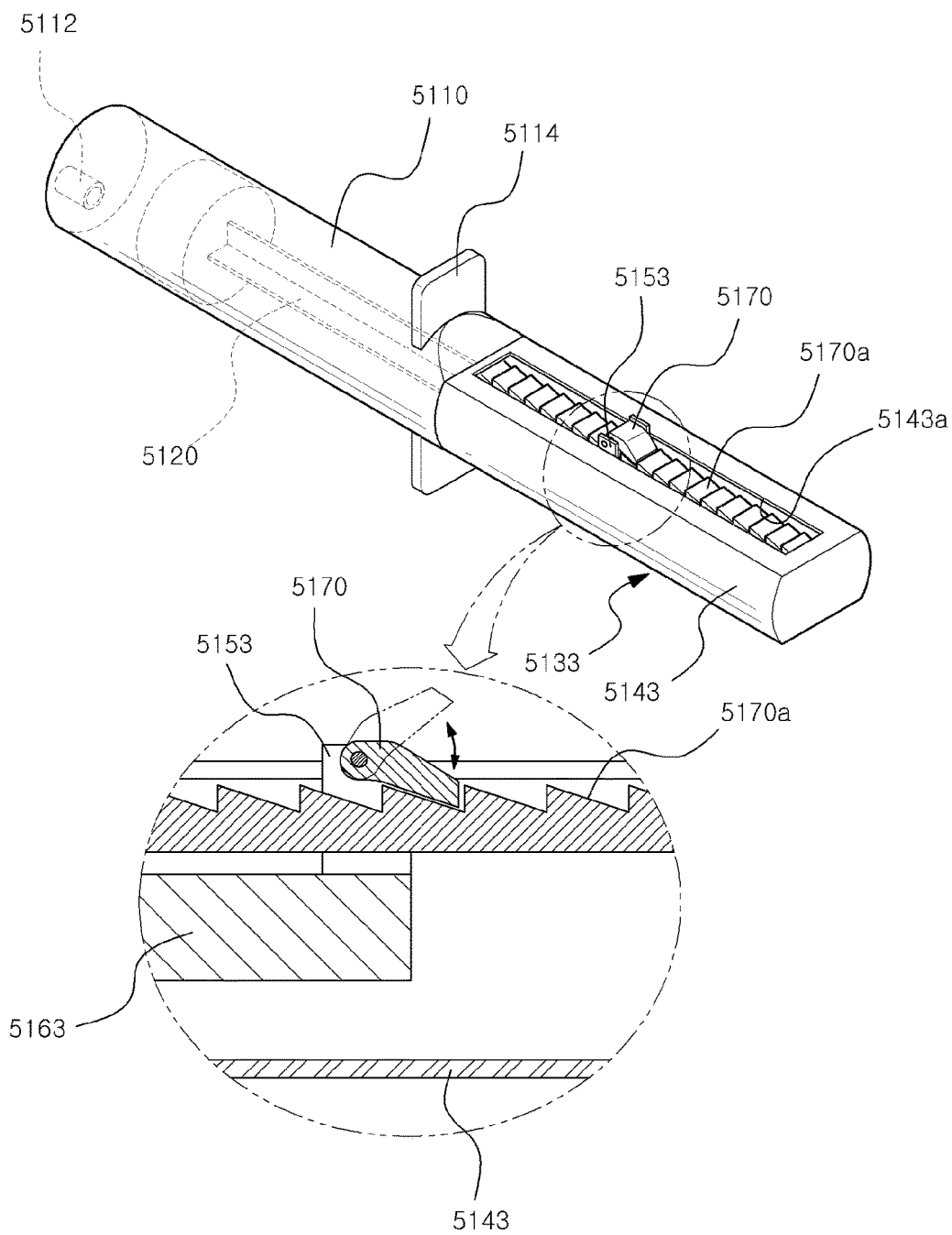

[Fig. 70]
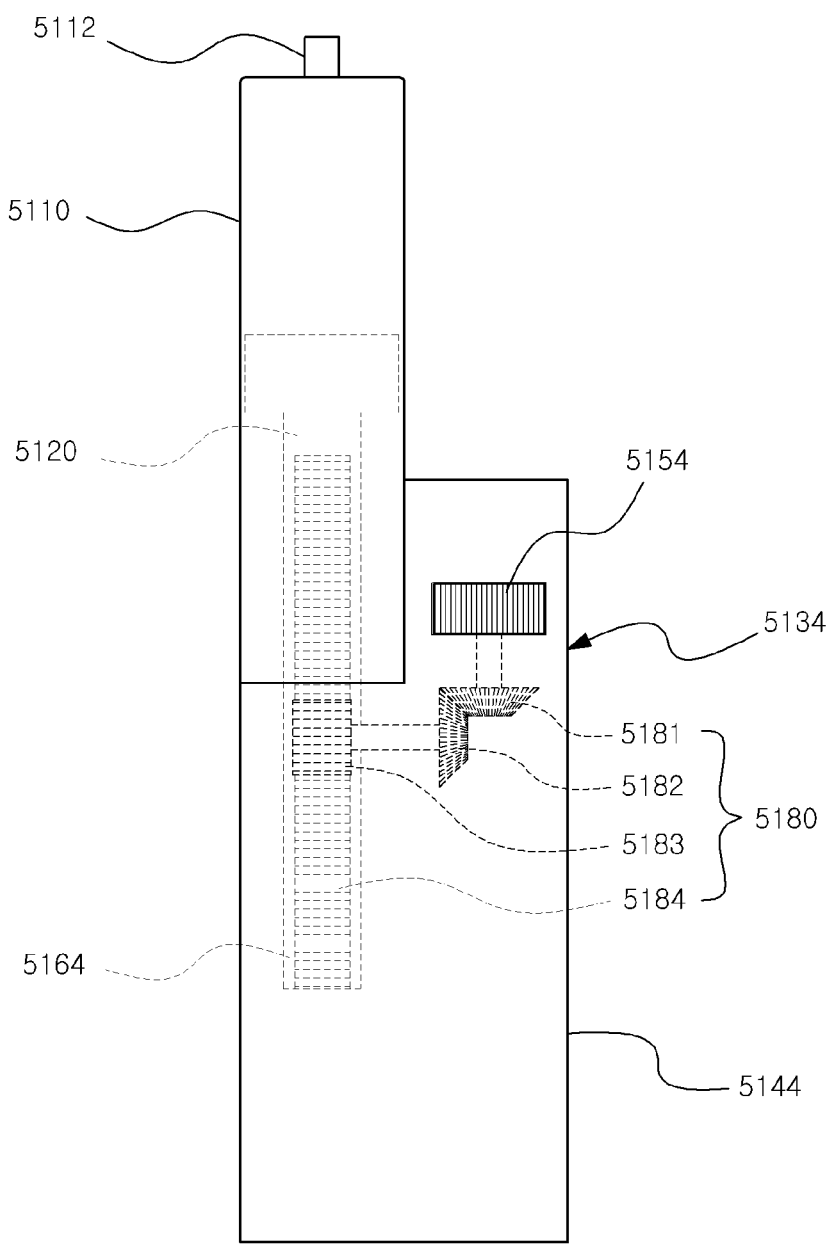

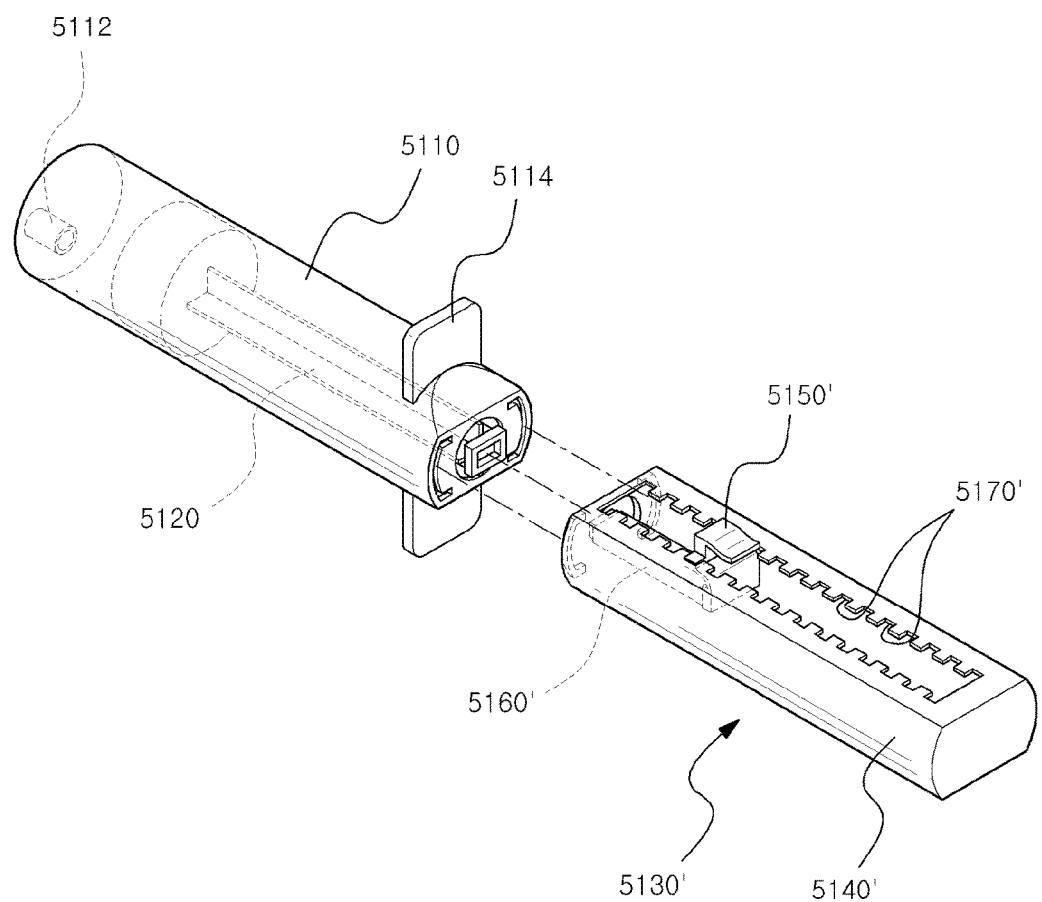
[Fig. 71]

[Fig. 72]
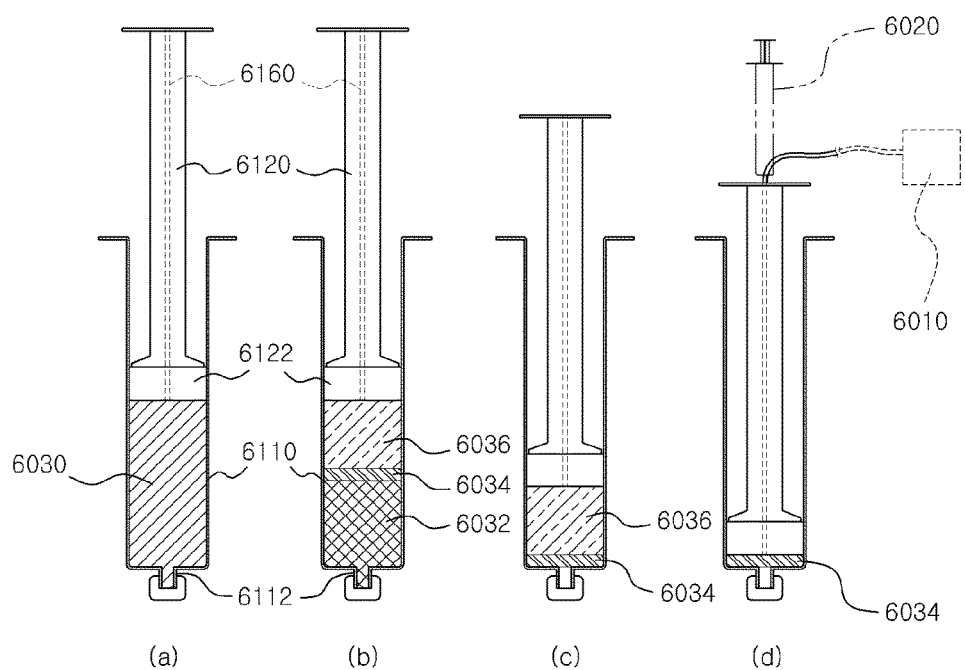

[Fig. 73]
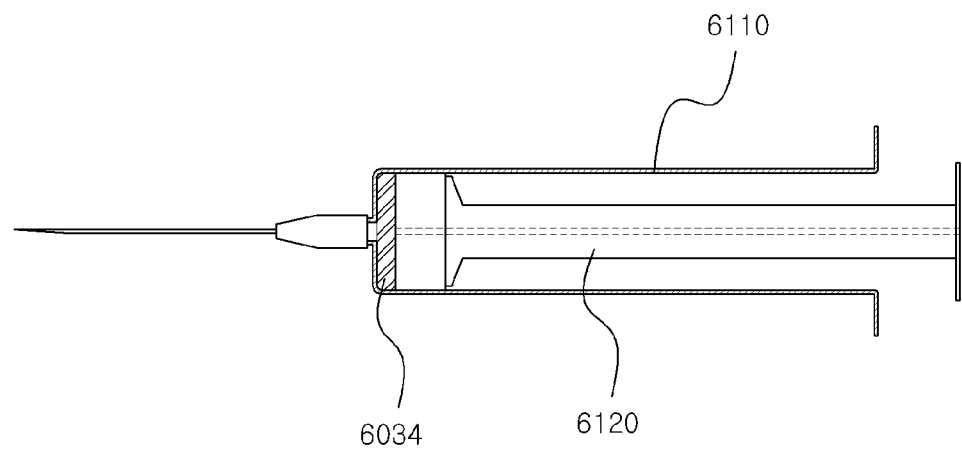

[Fig. 74]
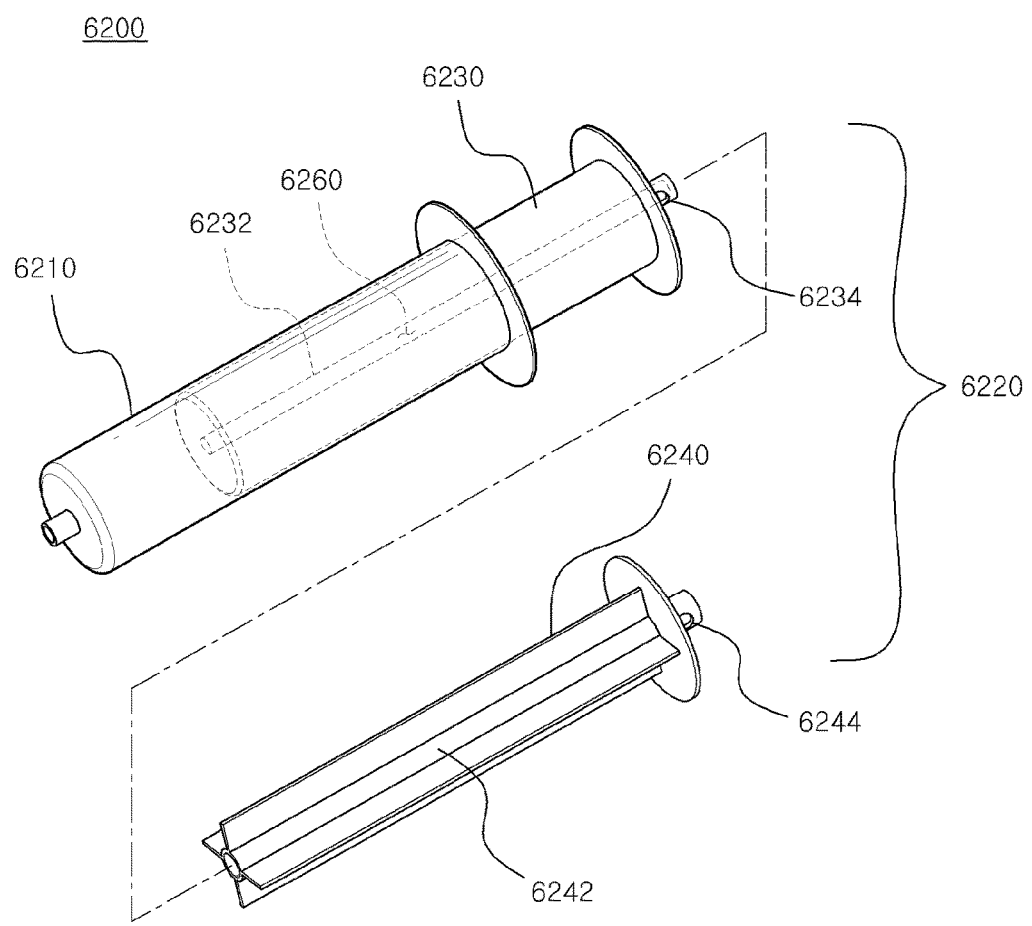

[Fig. 75]
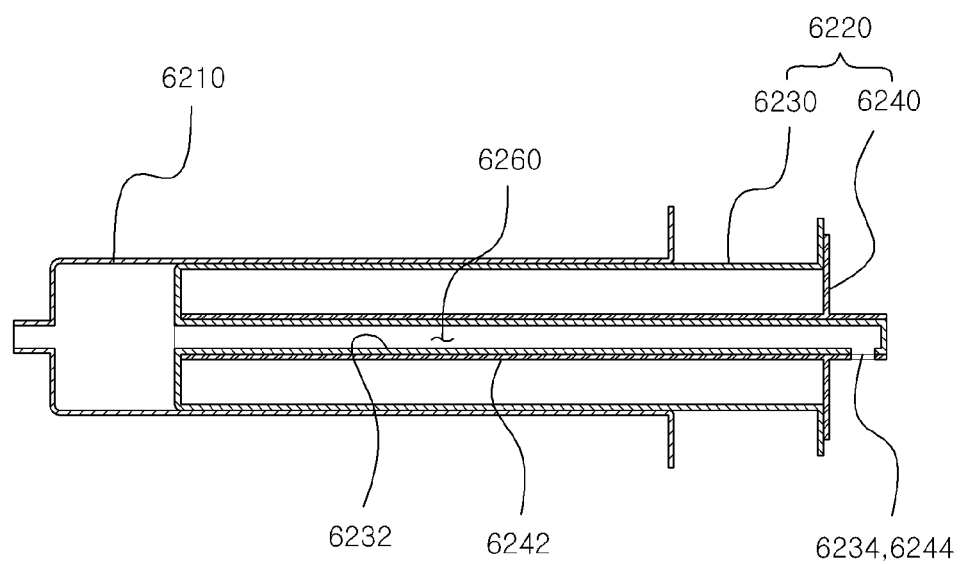

[Fig. 76]
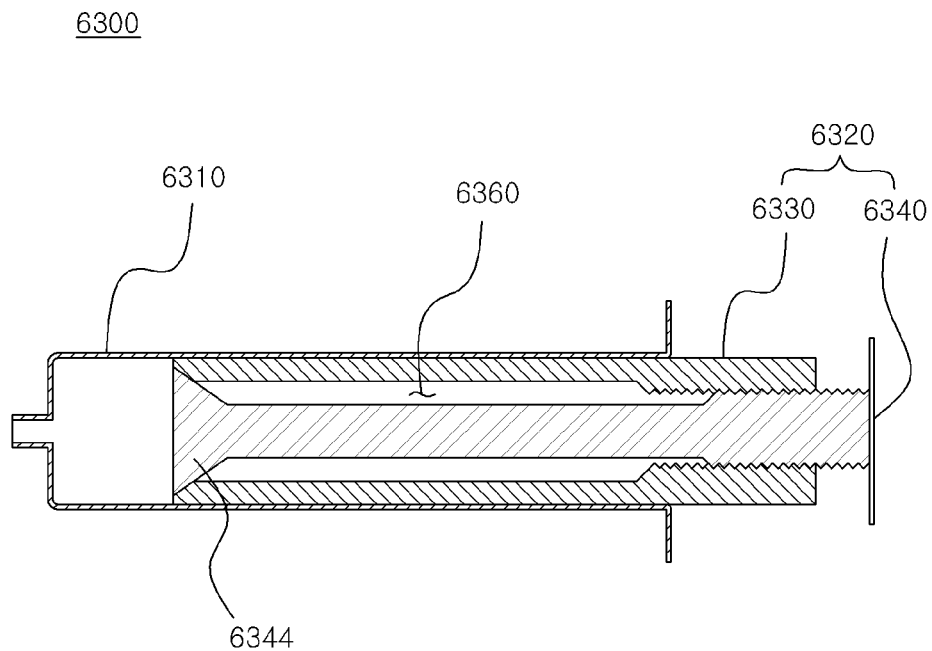

【Fig. 77】
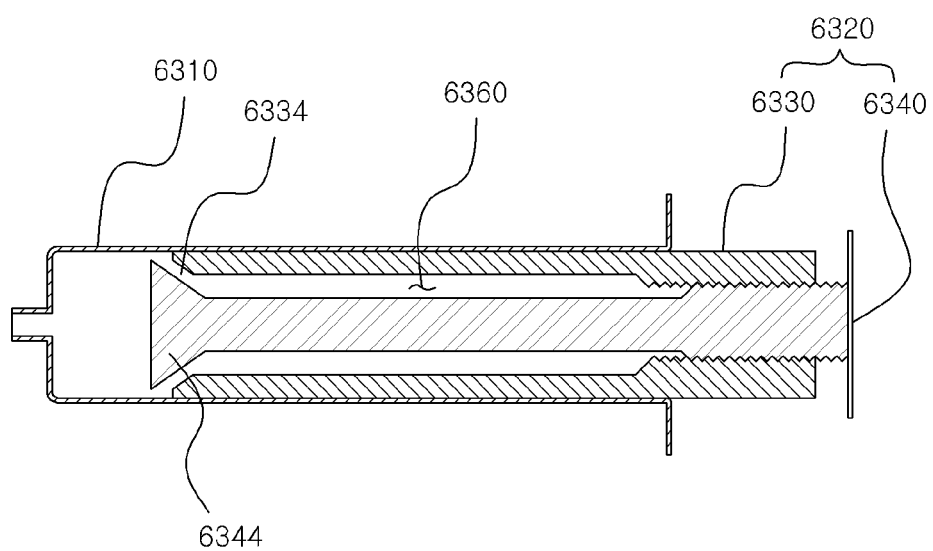

[Fig. 78]
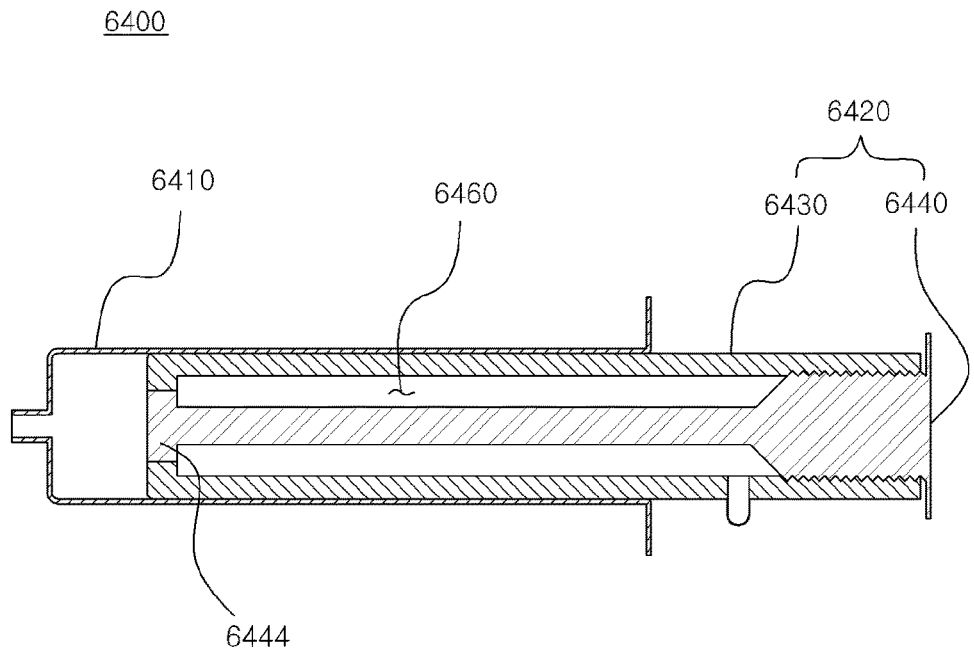

[Fig. 79]
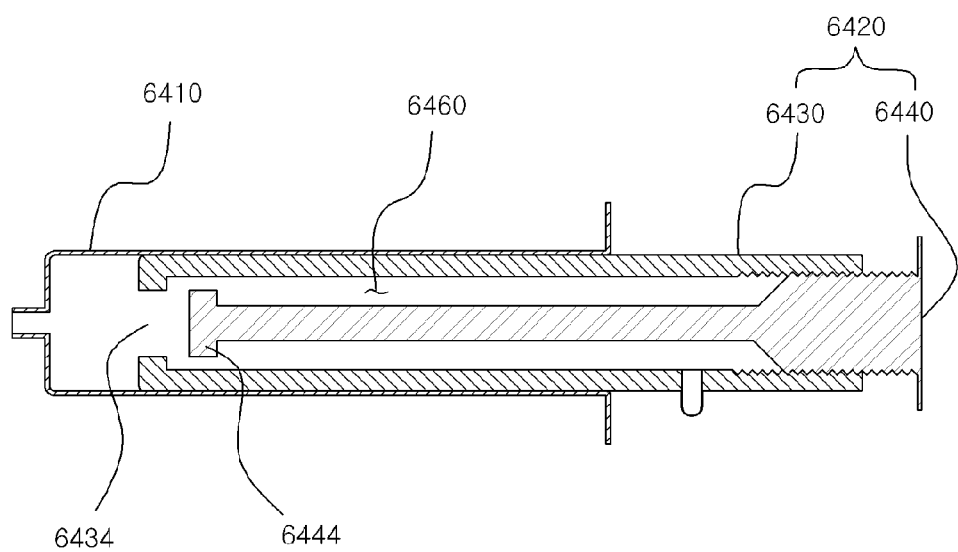

[Fig. 80]
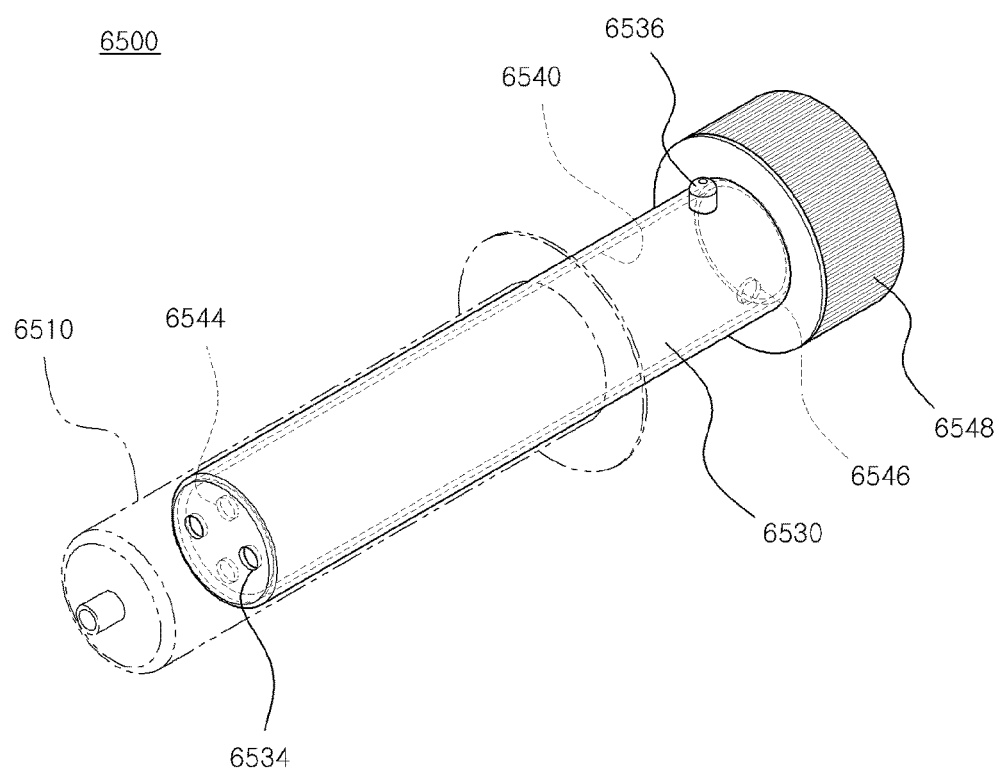

[Fig. 81]
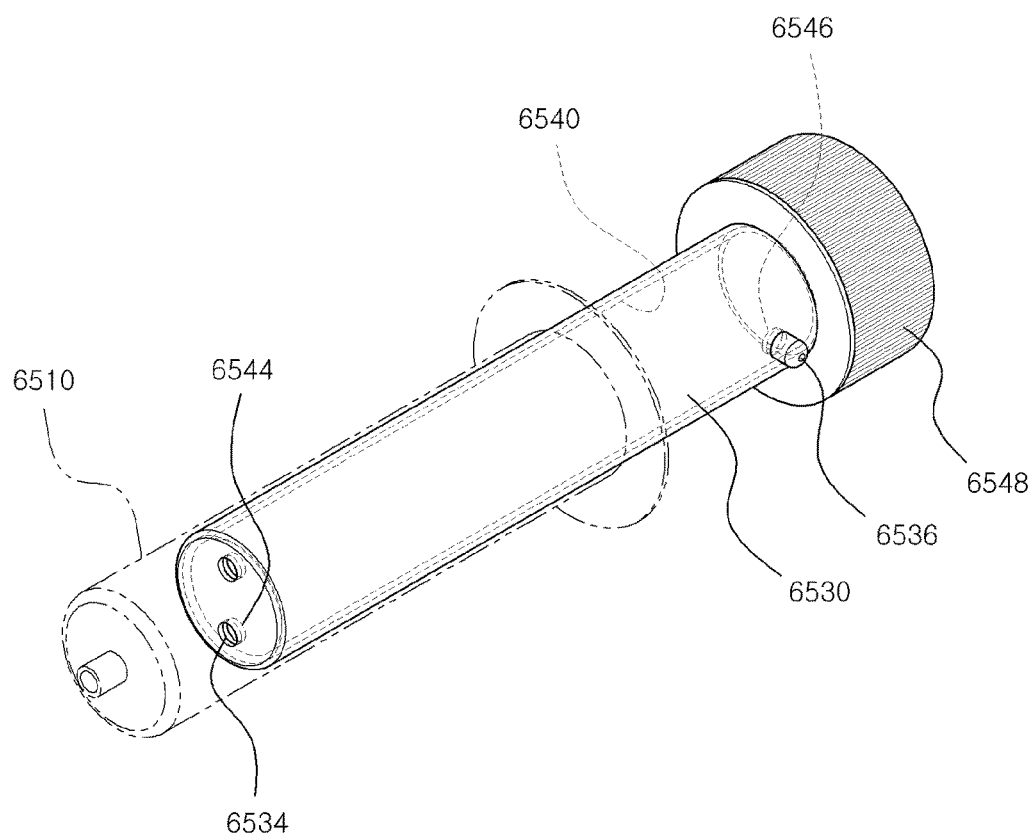

[Fig. 82]
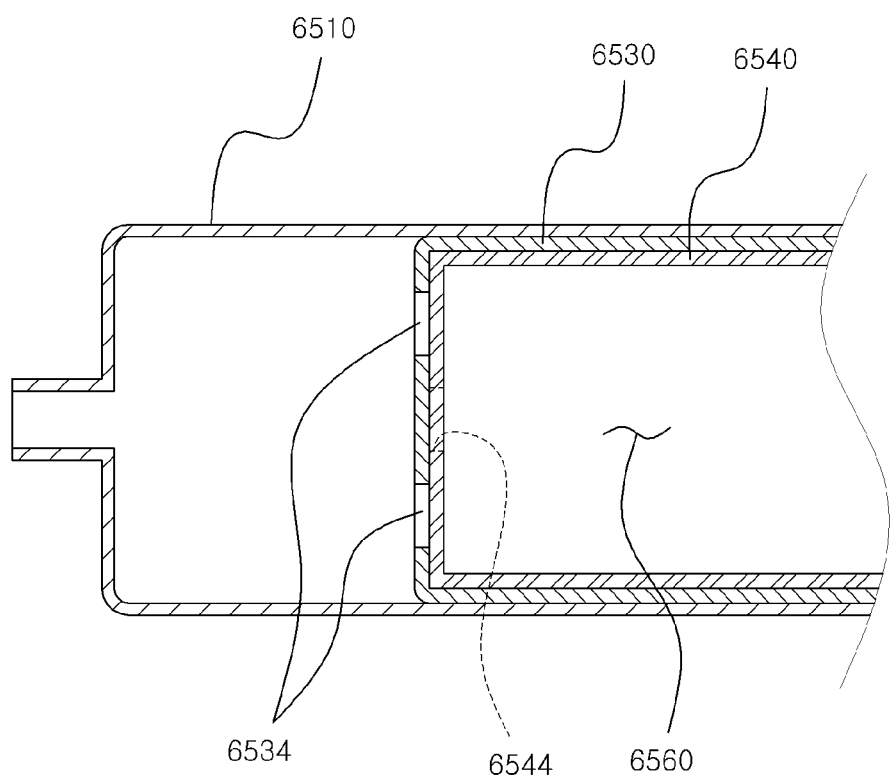

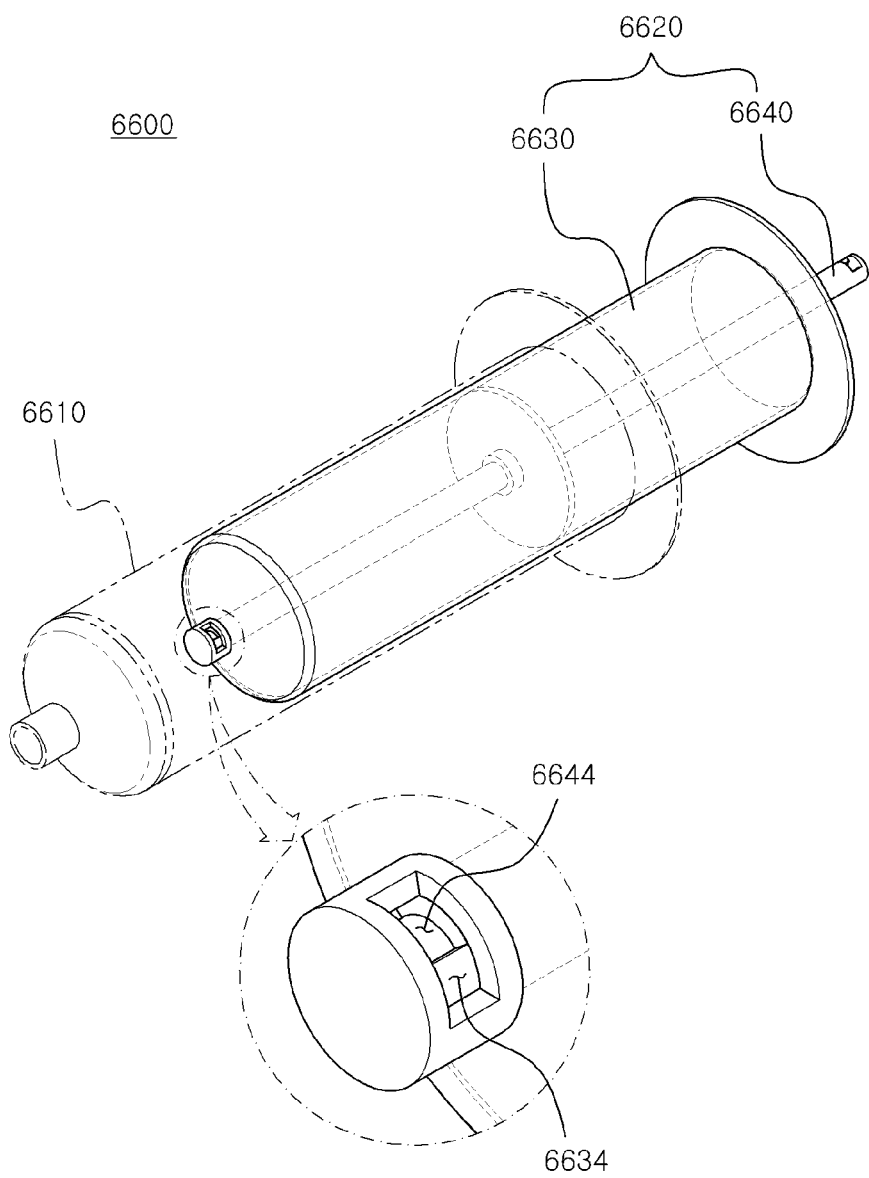
[Fig. 83]

[Fig. 84]
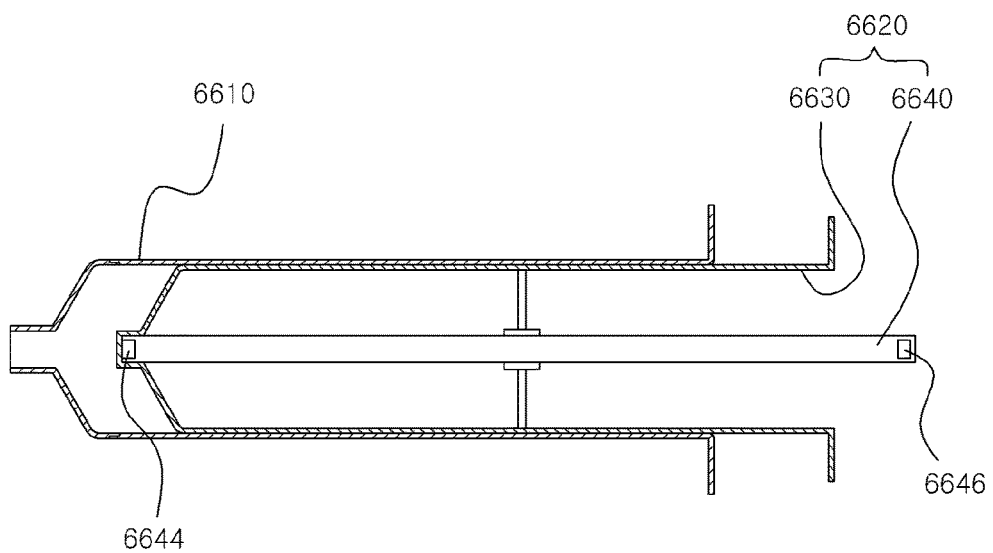

CENTRIFUGATION METHOD WITH A REVERSED SYRINGE POSITION

TECHNICAL FIELD

The present invention relates to a method and a device for centrifuging, more particularly, relates to a method and a device for centrifuging a mixture quickly and simply.

BACKGROUNDS

In general, blood is composed of blood cells and blood plasma. The blood cells are classes as red blood cell, white blood cell and blood platelet. The blood plasma is mainly composed of water and includes some blood coagulation element and ions.

As mentioned the above, blood is a mixture which includes various elements. In these days, blood extracting technologies for lots of medical uses are widely spread, and especially blood centrifugations are generally used.

The blood centrifugation uses differences of blood elements in weight to separate the elements by rotating the mixture at a high speed. When centrifuging whole blood, the red blood cells which are heaviest move downward or outside to form the lowest layer. On the layer of the red blood cells, layers of white blood cells, plasma and platelets are formed in order.

On the other hand, PRP (Platelet Rich Plasma) in the plasma may be positioned at the lower portion in the blood plasma layer, which can be usefully used specially for blood coagulation or stopping bleeding. Since the PRP contains cytokine, PDCF, TGF-BETA1, VEGP and the like, some research papers or articles reveal that the PRP is good for skin ailment and wound healing.

However, there are some problems that extracting target element like PRP from the whole blood is very complicated and difficult.

In the conventional methods, the red blood cells are separated from the blood through a centrifugation, and the blood platelet can be separated from remained blood through one more centrifugation. Accordingly, extracting platelets from blood needs at least two times of centrifugations, such that it is very inconvenient and complicated. Most of all, the blood should be exposed to the air when transferring the blood in the conventional methods.

In the conventional methods, since it takes too much time for the extraction of target element, it has been very difficult to inject the platelet extracted through at least two times of centrifugations in situ.

In these days, actively pushed are developments for centrifuging blood quickly and simply.

DISCLOUSE OF INVENTION

Technical Goals

The present invention provides a method and device for centrifuging a mixture, such as blood, more quickly and simply.

The present invention provides a method and device for centrifuging, which can extract target element without exposure or transfer of the mixture and prevent the mixture from be spoiled or infected because of exposure in the air.

The present invention provides a method and device for centrifuging, which can save time for the centrifugations and make it possible to directly apply the extracted element.

The present invention provides a centrifuging device which can extract target element from a mixture more easily.

Technical Solutions

According to one exemplary embodiment of the present invention, a method of centrifuging a mixture using a syringe which has a nozzle at one end, comprises the steps of taking the mixture in the syringe, first centrifuging the mixture in the syringe, discharging one part of the mixture which is adjacent to the nozzle after the first centrifuging, second centrifuging the mixture in the syringe after reversing the syringe, and discharging another part of the mixture which is adjacent to the nozzle after the second centrifuging.

For reference, a mixture in this specification may mean a object for centrifugation and may be selected in all kinds of material or mixture. For example, the mixture may be blood, secretion or any sample collected from human or animals.

The syringe may be a general medical syringe which includes a barrel and a plunger, and may not limit the scope of the present invention by its kind or property. The barrel includes a nozzle at its one end, which let a mixture enter or go out. The nozzle may be shut down during the first and the second centrifuging. In this specification, the "syringe" may mean a conventional syringe having a barrel and a plunger, or may mean other devices that include a reservoir and a piston to work like a syringe.

In the step of taking the mixture in the syringe, the mixture, such as blood, may move from human body directly to the barrel, otherwise it may be transferred to the barrel after being contained in another reservoir.

The first and the second centrifuging may be performed in the conventional centrifuging devices, and the present invention may not be limited by the kind or the property of the centrifuging devices. The rotating speed of the first and the second centrifuging may be different.

According to the necessary conditions, the syringe may be held in various directions and orders. For one example, the nozzle of the syringe may direct to the center at the first centrifuging and be reversed to see the outside at the second centrifuging.

During the first and the second centrifuging, the syringe may be treated in various ways. For example, the nozzle of the syringe in the first centrifuging may be arranged to direct the outside opposite to the center, then in the second centrifuging may be arranged to direct the inside to face the center. Occasionally, the nozzle may be arranged to direct to the center in the first centrifuging and to direct to the outside in the second centrifuging.

For reference, the rotating "center" may mean a rotating axis of a rotor in the centrifuging device, and the term "direct to the outside" may mean that the central line of the nozzle and the barrel comes into line with the rotating center or may mean that their central line passes substantially near the rotating center.

When the mixture is human blood, the heaviest element is located the outside of the barrel after the first centrifuging, and the heaviest element may involve red blood cells which is relatively heavy in the whole blood.

After the second centrifuging, other element remaining in the barrel, such as blood plasma and platelet, may form layers in the barrel due to the density difference. In this instance, the lightest element in the remaining elements may located near the nozzle to include blood plasma.

By discharging portions centrifuged near the nozzle after the first and the second centrifuging, target element remained in the barrel may contain blood platelet.

The syringe may further include a separable chamber can be selectively mounted to the nozzle. Portion of the one part discharged by the first centrifuging may be contained in the separable chamber after the first centrifuging and the separable chamber may be separated after the first centrifuging. Because heaviest element of the mixture is collected in the separable chamber by the first centrifuging, the amount of the one part which should be discharged may be reduced in the barrel, thereby to increase the purity of the target element.

According to one exemplary embodiment of the present invention, a centrifuging syringe for extracting target element from a mixture by centrifuging, may comprise a barrel having a nozzle at one end, and a plunger entering through the other end of the barrel to move straightly in the barrel, in which a plunger head of the plunger is provided with an adhesion barrier to prevent the target element from being adhered on the plunger head after the centrifuging.

The adhesion barrier may have a structure to prevent the target element from being adhered on the plunger head. For example, the adhesion barrier may include many protrusions formed on the plunger head. The protrusions for the adhesion barrier may be shaped of cone, pyramid, truncated cone, prismoid, cylinder, polyhedron or cylindroids. The protrusions may be arranged in a predetermined way, such as a grid array, wherein they may be formed to be equal or different in size. In other embodiments, the protrusion may be formed to have a shape of a ridge to form straight lines or curves.

Another adhesion barrier may be provided using mesh which is separated from a surface of the plunger head. The mesh or net for the adhesion barrier may be supported by a spacer interposed between the mesh and the plunger head.

According to one exemplary embodiment of the present invention, a syringe including a barrel having a nozzle at one end and a plunger entering through the other end of the barrel to move straightly in the barrel, may comprises a plunger handle positioned outside the barrel and mounted to the plunger to move together with the plunger, thereby the plunger moves straightly by operation of the plunger handle.

According to one exemplary embodiment of the present invention, a centrifuging device for extracting target element from a mixture through centrifuging, may comprise a barrel having a nozzle at one end, a plunger entering through the other end of the barrel to move straightly in the barrel, the plunger including a coupling hole, and a lock member selectively coupled with the coupling hole to lock the plunger to the barrel.

According to one exemplary embodiment of the present invention, a method of centrifuging for extracting target element from a mixture, by using a syringe which includes a barrel having a nozzle and a plunger moving straightly in the barrel to have an end flange, may comprising a step of providing an adapter including a barrel receiving portion for holding the barrel and a plunger receiving portion having a plurality of slits for holding the end flange, a step of placing the barrel in the barrel receiving portion and the end flange in one of the slits, and a step of performing a centrifugation by rotating the adapter.

According to one exemplary embodiment of the present invention, an adapter used for centrifuging using a syringe which including a barrel having a nozzle and a plunger moving straightly in the barrel to have an end flange, may comprises an adapter body, a barrel receiving portion formed in the adapter body for holding the barrel, and a plunger receiving portion for holding the plunger, wherein the plunger receiving portion includes a plurality of slits for holding the end flange.

According to one exemplary embodiment of the present invention, a syringe may comprises a barrel having a nozzle at one end, a plunger moving straightly in the barrel, and a plunger managing member provided at the other end of the barrel to be interlocked with the plunger, thereby the plunger moves straightly by operation of the plunger managing member.

According to one exemplary embodiment of the present invention, a centrifuging syringe for extracting target element from a mixture, which includes a barrel having a nozzle at one end and a plunger entering through the other end of the barrel to move straightly in the barrel, for extracting target element from a mixture, may comprise a path provided in the plunger and connected with an inner space defined by the barrel and a plunger head of the plunger, whereby one portion of the mixture can be separated from the other portion of the mixture by be transferred into the barrel via the path after centrifugation.

According to one exemplary embodiment of the present invention, a method of centrifuging for extracting target element from a mixture, by using a syringe which includes a barrel having a nozzle at one end and a plunger entering through the other end to move straightly in the barrel, may comprises providing a path in the plunger which is connected with an inner space defined by the barrel and a plunger head of the plunger, supplying a mixture inside the inner space defined by the barrel and the plunger head, centrifuging the mixture in the syringe, and separating one portion of the mixture near the plunger head from the other portion of the mixture through the path.

Advantageous Effects

According to one centrifuging method and device relating to a first embodiment of the present invention, the blood collected by a syringe needs not be transferred to a test tube or other reservoir and can be treated directly by centrifuging. After the first and the second centrifuging, a target element, for example PRP, may be remained in the syringe and can be injected again without any transferring. Through these processes, the target element can be extracted more sanitarily, quickly and easily.

Since all the extracting processes to get the target element are performed in one syringe, target element contained in the mixture like blood can be separated quickly and easily, and then can be injected directly in a human body.

According to the above centrifuging method and device, since the mixture is kept in one syringe and not exposed to the air, the mixture or the target element may not be spoiled or infected.

Moreover, the working time for the centrifuging may be very short and the result containing the target element can be used in situ. For example, after collecting patient's blood, the centrifuging processes to get the target element can be performed in one syringe and the extracted target element can be injected to the patient by the very syringe.

In case of using a separable chamber in the first centrifuging, part of the mixture which should be discharged is already collected in the separable chamber, not in the barrel, so as to improve the purity of the target element.

An adhesion barrier may be applied on a plunger head of the plunger. The adhesion barrier can reduce the adhesion of the target element on the plunger head, and help the target element be separated from the plunger head after the second centrifuging.

According to one syringe relating to a second embodiment of the present invention, since a plunger of the syringe can be locked to a barrel, the syringe can be used in centrifuging devices.

When performing a centrifuging, the plunger can be locked not to move unwillingly in the barrel. So the syringe of the present invention doesn't need an additional fixing member which can fix the plunger or the barrel and can keep the locking state between the barrel and the plunger by itself.

The syringe of the present invention may be used in multi uses, for example centrifugation, varied experimental tests and researches. In case of using a plunger handle which can move the plunger straightly, users can control the plunger stably by using one hand, without any help of the other hand.

Since the plunger of the present invention is temporarily locked, it may not be moved by unwilled impact or touch, so it can be used as a safe kind of syringe to need high safety and precision requirement.

According to another centrifuging method and device relating to a third embodiment of the present invention, the blood collected by a syringe needs not to be transferred to a test tube or other reservoir and can be treated directly by centrifuging. After the first and the second centrifuging, a target element, for example PRP, may be remained in the syringe and can be injected again without any transferring. Through these processes, the target element can be extracted more sanitarily, quickly and easily.

Since all the extracting processes to get the target element are performed in one syringe, target element contained in the mixture, e.g. blood, can be separated quickly and easily, and then can be injected directly in a human body.

According to another centrifuging method and device of the third embodiment, since the target element is extracted from the mixture without air exposure and transferring, the mixture and the target element may not be spoiled or infected.

The centrifuging processes can be completed in a short time and the result containing the target element can be used in situ. For example, after collecting patient's blood, the centrifuging processes to get the target element can be performed effectively and the extracted target element can be injected to the patient directly.

In this instance, all the steps may be preceded in one syringe to protect the target element from infection, which can occur in the transferring process.

According to another centrifuging method and an adapter for the method relating to a fourth embodiment of the present invention, a method of centrifuging for extracting target element from a mixture, by using a syringe which includes a barrel having a nozzle and a plunger moving straightly in the barrel to have an end flange, may comprise providing an adapter including a barrel receiving portion for holding the barrel and a plunger receiving portion having a plurality of slits for holding the end flange, placing the barrel in the barrel receiving portion and the end flange in one of the slits, and performing a centrifugation by rotating the adapter.

According to the centrifuging method and device of the fourth embodiment, the blood collected by a syringe needs not to be transferred to a test tube or other reservoir and can be treated directly by centrifuging. After the centrifuging, a target element, for example PRP, can be injected without any transferring. Through these processes, the target element can be extracted more sanitarily, quickly and easily.

Since all the extracting processes to get the target element are performed in one syringe in the first and second centrifuging, target element contained in the mixture can be separated quickly and easily, and then can be injected directly in a human body.

According to the centrifuging method and device of the present invention, since the target element is extracted from the mixture without air exposure and transferring, the mixture and the target element may not be spoiled or infected.

The centrifuging processes can be completed in a short time and the result containing the target element can be used in situ. For example, after collecting patient's blood, the centrifuging processes to get the target element can be performed effectively and the extracted target element can be injected to the patient directly.

In this instance, all the steps may be preceded in one syringe to protect the target element from infection, which can occur in the transferring process.

According to one syringe relating to a fifth embodiment of the present invention, since a plunger of the syringe can be locked to a barrel, the syringe can be used in centrifuging devices.

When performing a centrifuging, the plunger can be locked not to move unwillingly in the barrel. So the syringe of the present invention doesn't need an additional fixing member which can fix the plunger or the barrel and can keep the locking state between the barrel and the plunger by itself. Accordingly, in one implementation, no parts of the syringe move relative to each other during the first centrifuging or the second centrifuging.

The syringe of the fifth embodiment may be used in multi uses, for example centrifugation, varied experimental tests and researches. In case of using a plunger handle which can move the plunger straightly, users can control the plunger stably by using one hand, without any help of the other hand.

Since the plunger of the present invention is temporarily locked, it may not be moved by unwilled impact or touch, so it can be used as a safe kind of syringe to need high safety and precision requirement.

According to another centrifuging method and device relating to a sixth embodiment of the present invention, target element can be extracted from a mixture through few centrifuging processes in a syringe. In this method, the mixture and the target element are not exposed to the air, the target element can be separated quickly and simply. More particularly, because the mixture is not exposed to the outside, there is no problem about spoiling and infection due to the exposure.

In the sixth embodiment, the target element can be separated from the other elements via only one centrifuging. The upper and the lower layers of a target layer can be discharged from an inner space of the barrel, so as to remain the target layer containing the target element, which can reduce a working time to extract the target element.

BRIEF DESCRIPTION OF DRAWINGS

FIG. 1 is a block diagram illustrating a centrifuging method according to a first embodiment of the present invention, FIGS. 2 to 4 are sectional views illustrating processes of a first centrifuging and discharging to remove one part of a mixture according to the first embodiment of the present invention, FIGS. 5 to 7 are sectional views illustrating processes of a second centrifuging and discharging to remove another part of the remained mixture according to the first embodiment of the present invention, FIG. 8 is a sectional view illustrating a practical usage of target element extracted after the second centrifuging according to the first embodiment of the present invention, FIGS. 9 to 14 are enlarged perspective views illustrating various examples of the adhesion barriers according to the first embodiment of the present invention, FIGS. 15 and 16 are sectional views illustrating a centrifuging method according to another embodiment of the present invention, FIG. 17 is a perspective view illustrating a centrifuging syringe according to a second embodiment of the present invention, FIG. 18 is a sectional view along I-I' line in FIG. 17, FIGS. 19 and 20 are perspective views illustrating usages of the syringe according to the second embodiment, FIGS. 21 and 22 are side view of plan view illustrating another syringe of the present invention, FIGS. 23 to 25 are sectional views illustrating processes of a first centrifuging and discharging to remove one part of a mixture according to the second embodiment of the present invention, FIGS. 26 to 28 are sectional views illustrating processes of a second centrifuging and discharging to remove another part of the remained mixture according to the second embodiment of the present invention, FIG. 29 is a sectional view illustrating a practical usage of target element extracted after the second centrifuging according to the second embodiment of the present invention, FIGS. 30 and 31 are perspective views illustrating the structures of a centrifuging device according to a third embodiment of the present invention, FIGS. 32 to 34 are sectional views illustrating processes of a first centrifuging and discharging to remove one part of a mixture according to the third embodiment of the present invention, FIGS. 35 to 37 are sectional views illustrating processes of a second centrifuging and discharging to remove another part of the remained mixture according to the third embodiment of the present invention, FIG. 38 is a sectional view illustrating a practical usage of target element extracted after the second centrifuging according to the third embodiment of the present invention, FIGS. 39 to 43 are perspective views illustrating various structures of the centrifuging syringes according to other embodiments of the present invention, FIG. 44 is a block diagram illustrating a centrifuging method according to a fourth embodiment of the present invention, FIG. 45 is a block diagram illustrating a centrifuging process in detail according to the fourth embodiment of the present invention, FIG. 46 is a perspective view illustrating a structure of a centrifuging adapter according to the fourth embodiment of the present invention, FIGS. 47 to 49 are sectional views illustrating processes of a first centrifuging and discharging to remove one part of a mixture according to the fourth embodiment of the present invention, FIGS. 50 to 52 are sectional views illustrating processes of a second centrifuging and discharging to remove another part of the remained mixture according to the fourth embodiment of the present invention, FIG. 53 is a sectional view illustrating a practical usage of target element extracted after the second centrifuging according to the fourth embodiment of the present invention, FIGS. 54 and 55 are perspective views illustrating the structures of centrifuging adapters according to other embodiments of the present invention, FIGS. 56 to 58 are views illustrating an adapter according to another embodiment of the present invention, FIG. 59 is a perspective view illustrating a syringe according to the fifth embodiment of the present invention, FIGS. 60 to 62 are sectional views illustrating processes of a first centrifuging and discharging to remove one part of a mixture according to the fifth embodiment of the present invention, FIGS. 63 to 65 are sectional views illustrating processes of a second centrifuging and discharging to remove another part of the remained mixture according to the fifth embodiment of the present invention, FIG. 66 is a sectional view illustrating a practical usage of target element extracted after the second centrifuging according to the fifth embodiment of the present invention, FIGS. 67 to 71 are perspective views illustrating syringes according to other embodiments of the present invention, FIG. 72 is a sectional view illustrating a syringe and a centrifuging method according to a sixth embodiment of the present invention, FIG. 73 is a sectional view illustrating a practical usage of the syringe and the centrifuging method of the sixth embodiment of the present invention, FIG. 74 is a perspective view illustrating a centrifuging syringe according to one embodiment of the present invention, FIG. 75 is a sectional view illustrating the centrifuging syringe of FIG. 74, FIG. 76 is a sectional view illustrating a centrifuging syringe according to one embodiment of the present invention, FIG. 77 is a sectional view illustrating the operating mechanism of the centrifuging syringe of FIG. 76, FIG. 78 is a sectional view illustrating a centrifuging syringe according to one embodiment of the present invention, FIG. 79 is a sectional view illustrating the operating mechanism of the centrifuging syringe of FIG. 78, FIG. 80 is a perspective view illustrating a centrifuging syringe according to one embodiment of the present invention, FIG. 81 is a perspective view illustrating an operating mechanism of the centrifuging syringe of FIG. 80, FIG. 82 is a partially enlarged sectional view illustrating the structure of the syringe of FIG. 80, FIG. 83 is a perspective view illustrating a centrifuging syringe according to one embodiment of the present invention, and FIG. 84 is a sectional view illustrating the centrifuging syringe of FIG. 83.

BEST MODE FOR CARRYING OUT THE INVENTION

Reference will now be made in detail to embodiments of the present invention, examples of which are illustrated in the accompanying drawings, wherein like reference numerals refer to the like elements throughout. The embodiments are described below in order to explain the present invention by referring to the figures.

FIG. 1 is a block diagram illustrating a centrifuging method according to a first embodiment of the present invention, FIGS. 2 to 4 are sectional views illustrating processes of a first centrifuging and discharging to remove one part of a mixture according to the first embodiment of the present invention, FIGS. 5 to 7 are sectional views illustrating processes of a second centrifuging and discharging to remove another part of the remained mixture according to the first embodiment of the present invention, and FIG. 8 is a sectional view illustrating a practical usage of target element extracted after the second centrifuging according to the first embodiment of the present invention.

Referring to FIG. 1, a centrifuging method according to the first embodiment of the present invention may be performed by using a syringe 1100 which has a nozzle 1112 at its one end. The centrifuging method comprises taking the mixture in the syringe 1100 (S1010), first centrifuging the mixture in the syringe 1100 (S1020), discharging one part of the mixture which is adjacent to the nozzle 1112 after the first centrifuging (S1030), second centrifuging the mixture in the syringe 1100 after reversing the syringe 1100 (S1040), and discharging another part of the mixture which is adjacent to the nozzle 1112 after the second centrifuging (S1050).

The syringe 1100 may be a general syringe which includes a barrel 1110 and a plunger 1120. The scope of the present invention is not limited by the kind or property of the syringe 1100.

The barrel 1110 may have a hollow cylindrical body with a predetermined diameter or volume. The barrel 1110 includes one end where the nozzle 1112 is located and the other end which is opened to permit the plunger 1120 to enter and move. The nozzle 1112 can be temporarily sealed by a cap 1130 or other sealing members.

The plunger 1120 enters into the barrel 1110 to move straightly in the barrel 1110, and the mixture can be took into the barrel 1110 via the nozzle 1112 by the movement of the plunger 1120.

For reference, the mixture in this specification may mean a object for centrifugation and may be selected in all kinds of material or mixture. For example, the mixture may be blood, secretion or any sample collected from human or animals.

Hereinafter, the centrifuging method using the one syringe is described referring to FIGS. 2 to 7.

At first, blood may be collected in the barrel 1110. As mentioned the above, the blood can enter into the barrel 1110 via the nozzle 1112 when the plunger 1120 moves back. The blood as the mixture may be supplied directly from the human body through a needle (see Ref. No. 1132 in FIG. 8) mounted to the nozzle 1112. Otherwise, the blood may be supplied from another reservoir containing ready-collected blood.

As shown in FIG. 2, the syringe 1100 may be rotated by a conventional centrifuging device (not shown) to perform a first centrifuging with the blood in the barrel 1110. In this instance, the syringe 1100 is arranged on the centrifuging device, in which the nozzle 1112 directs to the outside opposite to a rotating center.

The syringe 1100 may be mounted on a rotor of a conventional centrifuging device. For one example, the rotor where the syringe 1100 is mounted may be a swing-type rotor or a fixed-angle rotor, which is not limited by kinds or properties of the rotor. The rotating center of the syringe 1100 may understood as equal to a rotating axis of the rotor.

When the syringe 1100 of which the nozzle 1112 directs outside rotates for centrifuging, the mixture can be divided into layers due to the differences of the densities of the elements. In this instance, one specific part A which is heavies in the blood is positioned at the most outside layer which is farthest from the rotating center. For reference, the layer for the heaviest element in the blood may contain red blood cells.

Then the one specific part of the blood, which is adjacent to the nozzle 1112 after the first centrifuging, may be discharged via the nozzle 1112. As shown in FIG. 4, the plunger 1120 moves toward the nozzle 1112 to make the one specific part A be discharged from the barrel 1110 to the outside.

In FIG. 5, the second centrifuging may be performed to divide the blood remained in the syringe 1100. The syringe 1100 is mounted in reversed direction, of which the nozzle 1112 directs to the rotating center.

When rotating the syringe 1100 in which the nozzle 1112 directs to the center, the remained mixture may be divided into layers of plasma and platelets as shown in FIG. 6. In this instance, the another specific part B which is relatively light in the remained blood is positioned at the most inside layer which is nearest to the nozzle 1112 in the barrel 1110. For reference, the layer for the light element in the blood may contain blood plasma.

The rotating speeds for the first and the second centrifuging may be different from each other. For one example, the rotating speed for the first centrifuging may be about 2500~3300 rpm, while the rotating speed for the second centrifuging may be about 4000~5500 rpm.

And then the anther specific part of the blood, which is adjacent to the nozzle 1112 after the second centrifuging, may be discharged via the nozzle 1112 too. As shown in FIG. 7, the plunger 1120 moves toward the nozzle 1112 to make the another specific part B be discharged from the barrel 1110 to the outside.

After the one specific part A and the second specific part B are discharged from the blood, the target element C remaining in the barrel 1110 may contain blood platelet richly.

As mentioned the above, the blood platelets may be extracted from the blood in the syringe 1100, through the first and the second centrifuging, and the extracted blood platelets may be used to various medical experiments and researches, or may be injected directly to patient by the syringe 1100 and a needle 1132 mounted to the nozzle 1112, as shown in FIG. 8.

By the way, when the blood platelets is separated from the blood plasma by the second centrifuging, the blood platelets may be concentrated on a plunger head 1122. If the plunger head 1122 has a flat surface, the blood platelets may be adhered on the flat surface of the plunger head 1122. To prevent the adhesion of the platelets, the syringe 1100 according to the first embodiment of the present invention further includes an adhesion barrier 1140.

FIGS. 9 to 14 are enlarged perspective views illustrating various examples of the adhesion barriers according to the first embodiment of the present invention. In the drawings, several elements substantially same to the elements described in the above may use the same reference numerals referring to the above descriptions.

Referring to FIG. 9, the centrifuging syringe 1100 of the first embodiment may be used to extract the target element from the mixture, comprises the barrel 1110 having the nozzle 1112 at one end, and the plunger 1120 entering through the other end of the barrel 1110 to move straightly in the barrel 1110, wherein the plunger head 1122 of the plunger 1120 is provided with the adhesion barrier 1140 to prevent the target element from being adhered on the plunger head 1122 after the centrifuging.

The adhesion barrier 1140 may be provided with various structure which can prevent the target element from being adhered on the surface of the plunger head 1122. For one example, the adhesion barrier 1140 may be formed to have protrusions 1141 formed on the surface of the plunger head 1122.

Accordingly, when the target element is concentrated on the surface of the plunger head 1122 by the centrifuging, the target element would not be adhered on the plunger head 1122 to be scattered by the protrusions 1141, so that the adhesions of the target element can be remarkably reduced and easily removed from the plunger head 1122.

The adhesion barrier 1140 may be formed in various shapes, such as in a shape of cone, pyramid (ex. square pyramid, triangular pyramid, etc.), truncated cone, prismoid, cylinder, polyhedron and cylindroids.

The protrusions 1141 may be arranged in a predetermined way, such as a grid array, wherein they may be formed to be equal or different in size. In this embodiment, the protrusions 1141 are equal in size and shaped of a square pyramid, as shown in FIG. 9.

Otherwise, as shown in FIG. 10, protrusions 1142 may be formed in a shape of a ridge. For one example, the protrusions 1142 is formed in a ring shape to have a triangular section, which are arranged concentrically. In other embodiments, ridge-shaped protrusions may have a cross section shape of square or other geometric section, or may be formed in a spiral arrangement.

Some protrusions 1143 may be provided in a shape of a half sphere as shown in FIG. 11, and other protrusions 1144 may be provided in a shape of a hexahedron as shown in FIG. 12.

According to another embodiment, an adhesion bather may be provided using a mesh or a net which is separated from a surface of the plunger head 1122. As shown in FIG. 13, the adhesion barrier 1140' may include a mesh 1147 spatially separated from the surface of the plunger head 1122.

Referring to FIG. 14, the mesh 1147 of the adhesion barrier 1140' may be supported by a spacer 1148 interposed between the mesh 1147 and the plunger head 1122. The spacer 1148 may be spheres provided between the mesh 1147 and the plunger head 1122.

To form the adhesion bather, the surface of the plunger head may be scratched to have a rough surface, or be provided in varied structures or methods.

FIGS. 15 and 16 are sectional views illustrating a centrifuging method according to another embodiment of the present invention.

Referring to FIGS. 15 and 16, the syringe 1100 may be provided with a separable chamber 1150 which can be mounted to or separated from the nozzle 1112. In case of performing the first centrifuging to discharge the one specific part of the mixture, the one specific part of the mixture may be collected mainly in the separable chamber 1150, and then the separable chamber 1150 may be separated together with the one specific part.

The separable chamber 1150 may be formed to have a hollow body which is connected to the barrel 1110. The separable chamber 1150 may have a connecting member 1152 to fix the chamber to the nozzle.

When using the separable chamber 1150, the separable chamber 1150 may be coupled to the nozzle 1112 of the syringe 1100 during the first centrifuging. By rotating the syringe 1100 coupled with the separable chamber 1150, the layer separation of the elements of the blood may occur in the barrel 1110 and the separable chamber 1150, and the boundary of the layer separation can be controlled to be positioned near the nozzle 1112, and the red blood cells which are heaviest in the blood can be collected mainly in the separable chamber 1150.

In this instance, it is not preferable that all the red blood cells are collected in the separable chamber 1150 during the first centrifuging, because portion of the blood platelets can be collected in the separable chamber. Accordingly, it is preferable that little portion of the red blood cells remain in the barrel adjacent to the nozzle.

By using the separable chamber 1150 in the first centrifuging, the red blood cells may be collected mainly in the separable chamber 1150 and prevent the purity of the platelets from being decreased due to the red blood cells remaining in the syringe 1100.

Generally, the inside surface of the barrel may have a certain surface roughness degree, but not zero. So, small amount of red blood cell which could be survived on the inside surface of the barrel can decrease the purity of the platelets, even after the second centrifuging. However, if most of the red blood cells would be collected in the separable chamber 1150, the amount of the red blood cells remained in the barrel 1110 can be minimized, and the purity of the platelets can be improved.

In the present embodiment, the ceiling 1154 of the separable chamber 1150 is simply flat, while the ceiling of another separable chamber may be inclined for an easy layer separation.

FIG. 17 is a perspective view illustrating a centrifuging syringe according to a second embodiment of the present invention, and FIG. 18 is a sectional view along I-I' line in FIG. 17. FIGS. 19 and 20 are perspective views illustrating usages of the syringe according to the second embodiment.

Referring to FIGS. 17 and 18, the syringe 2100 may comprise a barrel 2110, a plunger 2120 and a plunger handle 2130.

The syringe 2100 according to the second embodiment may be used for centrifuging or general purpose, which may be used for general drug injections, experiments, researches, etc. The syringe 2100 can be used for various purposes.

The barrel 2110 may be a cylindrical hollow body and have a nozzle 2112 formed at the one end of the barrel 2110 for receiving blood or other fluidic material. The other end of the barrel 2110 is opened to permit the plunger 2120 to enter and move. At the nozzle 2112, a needle or a cap may be mounted to the nozzle 2112.

The plunger 2120 enters through the other end of the barrel 2110 to move straightly, and may let the fluidic material enter or go out via the nozzle 2112.

The plunger handle 2130 is coupled with the plunger 2120 to be exposed out of the barrel 2110, and the plunger 2120 moves in the barrel 2110 in accordance with the movement of the plunger handle 2130. A guide slot 2114 may be formed in the wall of the barrel 2110, and the plunger handle 2130 may be exposed through the guide slot 2114 to let the plunger 2120 move together.

The plunger handle 2130 may be formed by injection molding to be integrated with the plunger 2120 and be positioned at the side of the plunger 2120. Otherwise, the plunger handle and the plunger are manufactured respectively, and then are assembled.

The guide slot 2114 is formed straightly and the plunger handle 2130 moves straightly along the guide slot 2114. As shown in FIG. 19, a user holding the barrel 2110 can operate the plunger handle 2130 using his or her finger to move the plunger 2120.

The syringe 2100 may further comprise a coupling part to fix the plunger handle 2130 temporarily to the barrel 2110. The coupling part may be provided with various structures which can limit the movement of the plunger handle 2130. For one example, the guide slot 2114 may have a plurality of coupling steps 2140 and the plunger handle 2130 is positioned at a predetermined position and move to one of the coupling steps 2140 to be temporarily fixed.

In this embodiment, first coupling steps 2142 and second coupling steps 2144 are formed along the both sides of the guide slot 2114 to face to each other. The plunger handle 2130 moves along the guide slot 2114, stops at the predetermined position, and then moves perpendicularly to enter into one of the first coupling steps 2142 or the second coupling steps 2144. The coupling steps may be formed alternately along the both sides or along only one side of the guide slot 2114.

The coupling steps 2140 may fix the plunger handle 2130 temporarily, or may be used as a kind of scale.

FIGS. 21 and 22 are side view of plan view illustrating another syringe of the present invention.

Referring to FIG. 21, the syringe comprises the barrel 2110 including the nozzle 2112 and the guide slot 2114, the plunger 2120 moving in the barrel 2110, and the plunger handle 2130 integrated with the plunger 2120 as one body. On the barrel 2110, additional indicator 2150 may be formed on the barrel 2110.

The indicator 2150 may be expressed by using at least one of scales, numbers, letters, mark and pattern. and the user can recognize the volume of which is remained or discharged. Hereinafter, the indicator 2150 is printed on the barrel 2110 by using numbers.

In FIG. 21, the first coupling steps and the second coupling steps are formed along the both sides of the guide slot 2114, to be coincidentally disposed.

According to another embodiment, as shown in FIG. 22, coupling steps 2140' for holding the plunger handle 2130 are composed of first coupling steps 2142' and second coupling steps 2144', which are disposed by a uniform interval along one side of the guide slot 2114 respectively, but are alternatively disposed.

The first coupling steps 2142' and the second coupling steps 2144' may be disposed alternatively along the guide slot 2114, whereby the plunger handle 2130 can be stopped in the first coupling step 2142' or the second coupling step 2144'. To dispose the coupling steps alternatively, the holding position of the plunger handle 2130 can be precisely controlled.

On the barrel 2110, the indicators 2150' and 2150" may be expressed by using numbers printed near the each of the first and the second coupling steps 2142' and 2144'.

In this embodiment, the guide slot is formed straightly to guide the straight movement of the plunger handle, while, in other embodiments, a guide slot may be formed spirally to guide the straight and rotating movement of a plunger handle.

Hereinafter, the centrifuging method using the one syringe is described according to the second embodiment of the present invention.

FIGS. 23 to 25 are sectional views illustrating processes of a first centrifuging and discharging to remove one part of a mixture according to the second embodiment of the present invention, FIGS. 26 to 28 are sectional views illustrating processes of a second centrifuging and discharging to remove another part of the remained mixture according to the second embodiment of the present invention, and FIG. 29 is a sectional view illustrating a practical usage of target element extracted after the second centrifuging according to the second embodiment of the present invention.

At first, blood may be collected in the barrel 2110. As mentioned the above, the blood can enter into the barrel 2110 via the nozzle 2112 when the plunger 2120 moves back. The blood as the mixture may be supplied directly from the human body through a needle (see Ref. No. 2132 in FIG. 29) mounted to the nozzle 2112. Otherwise, the blood may be supplied from another reservoir containing ready-collected blood.

As shown in FIG. 23, the syringe 2100 may be rotated by a conventional centrifuging device (not shown) to perform a first centrifuging with the blood in the barrel 2110. In this instance, the syringe 2100 is arranged on the centrifuging device, in which the nozzle 2112 directs to the outside opposite to a rotating center.

The syringe may be mounted to the rotor by using a general adapter or rotation bucket, or be mounted directly on the rotor.

When the syringe 2100 of which the nozzle 2112 directs outside rotates for centrifuging, the mixture can be divided into layers, as shown in FIG. 24, due to the differences of the densities of the elements. In this instance, one specific part A which is heaviest in the blood is positioned at the most outside layer which is farthest from the rotating center. For reference, the layer for the heaviest element in the blood may contain red blood cells.

Then the one specific part A of the blood, which is adjacent to the nozzle 2112 after the first centrifuging, may be discharged via the nozzle 2112. As shown in FIG. 25, the plunger 2120 moves toward the nozzle 2112 to make the one specific part A be discharged from the barrel 2110 to the outside.

In FIG. 26, the second centrifuging may be performed to divide the blood remained in the syringe 2100. The syringe 2100 is mounted in reversed direction, of which the nozzle 2112 directs to the rotating center.

When rotating the syringe 2100 in which the nozzle 2112 directs to the center, the remained mixture may be divided into layers of plasma and platelets as shown in FIG. 27. In this instance, the another specific part B which is relatively light in the remained blood is positioned at the most inside layer which is nearest to the nozzle 2112 in the barrel 2110. For reference, the layer for the light element in the blood may contain blood plasma.

The rotating speeds for the first and the second centrifuging may be different from each other. For one example, the rotating speed for the first centrifuging may be about 2500~3300 rpm, while the rotating speed for the second centrifuging may be about 4000~5500 rpm.

And then the anther specific part B of the blood, which is adjacent to the nozzle 2112 after the second centrifuging, may be discharged via the nozzle 2112 too. As shown in FIG. 28, the plunger 2120 moves toward the nozzle 2112 to make the another specific part B be discharged from the barrel 2110 to the outside.

After the one specific part A and the second specific part B are discharged from the blood, the target element C remaining in the barrel 2110 may contain blood platelet richly.

As mentioned the above, the blood platelets may be extracted from the blood in the syringe 2100, through the first and the second centrifuging, and the extracted blood platelets may be used to various medical experiments and researches, or may be injected directly to patient by the syringe 2100 and a needle 2132 mounted to the nozzle 2112, as shown in FIG. 29.

During the first and the second centrifuging, since the plunger handle 2130 is temporarily fixed in the coupling steps 2140, the plunger 2120 is also fixed to the barrel 2110.

The user holding the barrel 2110 can operate the plunger handle 2130 using his or her finger to move the plunger 2120 and can discharge part of the mixture via the nozzle 2112.

FIGS. 30 and 31 are perspective views illustrating the structures of a centrifuging device according to a third embodiment of the present invention, FIGS. 32 to 34 are sectional views illustrating processes of a first centrifuging and discharging to remove one part of a mixture according to the third embodiment of the present invention, FIGS. 35 to 37 are sectional views illustrating processes of a second centrifuging and discharging to remove another part of the remained mixture according to the third embodiment of the present invention, and FIG. 38 is a sectional view illustrating a practical usage of target element extracted after the second centrifuging according to the third embodiment of the present invention.

Referring to FIG. 30, the syringe 3100 may comprise a barrel 3110, a plunger 3120 and a coupling member 3200.

For reference, the centrifuging device of the present invention may be used to perform a centrifuging in various experiments and researches. Also, the mixture in this specification may mean a object for centrifugation and may be selected in all kinds of material or mixture. For example, the mixture may be blood, secretion or any sample collected from human or animals.

The barrel 3110 may be a cylindrical hollow body and have a nozzle 3112 formed at the one end of the barrel 3110 for receiving blood or other fluidic material. The other end of the barrel 3110 is opened to permit the plunger 3120 to enter and move.

The plunger 3120 enters through the other end of the barrel 3110 to move straightly, and may let the fluidic material enter or go out via the nozzle 3112. The barrel 3110 may have a finger flange 3114 formed at the other end opposite to the nozzle 3112. The finger flange 3114 may have a hole-shaped structure (not shown) in other embodiments.

The plunger 3120 may have coupling holes 3122 and the coupling member 3200 may be selectively coupled with the coupling holes 3122 to fix the plunger 3120 to the barrel 3110.

To fix the plunger 3120 to the barrel 3110, there may be varied ways to utilize the coupling holes 3122 and the coupling member 3200. For one example, the coupling holes 3122 may formed along the plunger 3120 by a regular or irregular interval. The coupling member 3200 may be coupled to at least one of the coupling holes 3122 to fix the plunger 3120.

The coupling member 3200 may be a pin, a rod, a plate, etc. Hereinafter, the coupling member 3200 is provided in a shape of "U" to be coupled with two of the coupling holes 3122.

Referring to FIG. 31, the barrel 3110 and the plunger 3120 can be settled on an adapter 3300 where the plunger 3120 is fixed temporarily by the coupling member 3200.

In this specification, the adapter 3300 may be mounted to a rotor of a centrifuging device and be provided with various structures or types not to limit the scope of the present invention. For example, the adapter 3300 may be applied to various types of rotors, such as swing-out rotors or fixed-angle rotors.

The adapter 3300 may comprise a barrel receiving portion for holding the barrel 3110. The barrel receiving portion 3310 may be formed concavely according to the barrel 3110 to hold the barrel 3110. For example, the barrel receiving portion 3310 may have a flange slit 3314 to receive the finger flange 3114 of the barrel 3110 and fix the barrel 3110 stably.

In this embodiment, the flange slit 3314 is formed in the middle of the barrel receiving portion 3310, but another barrel receiving portion is formed in accordance with the precise contour of the barrel.

The adapter 3300 may further comprise a plunger receiving portion 3320 for holding the plunger 3120. The plunger receiving portion 3320 may be formed to receive the plunger 3120.

In the adapter 3300, there may be fixing holes 3312 according to the coupling holes 3122, and the coupling member 3200 may pass through the coupling hole 3122 to be fixed to the fixing hole 3312. Plurality of the fixing holes 3312 are formed in the adapter 3300 at the regular or irregular interval like the coupling holes 3122.

Hereinafter, the centrifuging method using the one syringe is described according to the third embodiment of the present invention, referring to FIGS. 32 to 38.

At first, blood may be collected in the barrel 3110. As mentioned the above, the blood can enter into the barrel 3110 via the nozzle 3112 when the plunger 3120 moves back. The blood as the mixture may be supplied directly from the human body through a needle (see Ref. No. 3132 in FIG. 38) mounted to the nozzle 3112. Otherwise, the blood may be supplied from another reservoir containing ready-collected blood.

As shown in FIG. 32, the syringe 3100 may be rotated by a conventional centrifuging device (not shown) to perform a first centrifuging with the blood in the barrel 3110. In this instance, the syringe 3100 is arranged on the centrifuging device, in which the nozzle 3112 directs to the outside opposite to a rotating center.

When the syringe 3100 of which the nozzle 3112 directs outside rotates for centrifuging, the blood can be divided into layers, as shown in FIG. 33, due to the differences of the densities of the elements. In this instance, one specific part A which is heaviest in the blood is positioned at the most outside layer which is farthest from the rotating center. For reference, the layer for the heaviest element in the blood may contain red blood cells.

Then the one specific part A of the blood, which is adjacent to the nozzle 3112 after the first centrifuging, may be discharged via the nozzle 3112. As shown in FIG. 34, the plunger 3120 moves toward the nozzle 3112 to make the one specific part A be discharged from the barrel 3110 to the outside.

In FIG. 35, the second centrifuging may be performed to divide the blood remained in the syringe 3100. The syringe 3100 is mounted in reversed direction, of which the nozzle 3112 directs to the rotating center.

When rotating the syringe 3100 in which the nozzle 3112 directs to the center, the remained mixture may be divided into layers of plasma and platelets as shown in FIG. 36. In this instance, the another specific part B which is relatively light in the remained blood is positioned at the most inside layer which is nearest to the nozzle 3112 in the barrel 3110. For reference, the layer for the light element in the blood may contain blood plasma.

The rotating speeds for the first and the second centrifuging may be different from each other. For one example, the rotating speed for the first centrifuging may be about 2500~3300 rpm, while the rotating speed for the second centrifuging may be about 4000~5500 rpm.

And then the anther specific part B of the blood, which is adjacent to the nozzle 3112 after the second centrifuging, may be discharged via the nozzle 3112 too. As shown in FIG. 37, the plunger 3120 moves toward the nozzle 3112 to make the another specific part B be discharged from the barrel 3110 to the outside.

After the one specific part A and the second specific part B are discharged from the blood, the target element C remaining in the barrel 3110 may contain blood platelet richly.

As mentioned the above, the blood platelets may be extracted from the blood in the syringe 3100, through the first and the second centrifuging, and the extracted blood platelets may be used to various medical experiments and researches, or may be injected directly to patient by the syringe 3100 and a needle 3132 mounted to the nozzle 3112, as shown in FIG. 38.

FIGS. 39 to 43 are perspective views illustrating various structures of the centrifuging syringes according to other embodiments of the present invention.

In the above embodiment, the direction of the syringe is fixed in the adapter 3300. However, in other embodiments, the direction of syringes may be freely selected in an adapter.

Referring to FIG. 39, a centrifuging device may comprises a barrel 3110, a plunger 3120, a coupling member 3200 and an adapter 3300. The adapter comprises a barrel receiving portion 3310, a plunger receiving portion and fixing holes 3312. The barrel receiving portion may be composed of a first barrel receiving portion 3310' and a second barrel receiving portion 3310" which are directed mutually opposite to each other. The fixing holes 3312 and the plunger receiving portion are formed in the first barrel receiving portion 3310' and the second barrel receiving portion 3310".

For the first centrifuging, the barrel 3110 may be positioned in the first barrel receiving portion 3310', the plunger 3120 may be positioned in the second barrel receiving portion 3310", and then the coupling member 3200 passes through the coupling hole 3122 to be fixed to the fixing hole 3312' in the second barrel receiving portion 3310". However, for the second centrifuging, the barrel 3110 may be positioned in the second barrel receiving portion 3310", the plunger 3120 may be positioned in the first barrel receiving portion 3310', and then the coupling member 3200 passes through the coupling hole 3122 to be fixed to the fixing hole 3312' in the first barrel receiving portion 3310'.

In another embodiment, a first barrel receiving portio and a second receiving portion may be separated by a predetermined distance, and a plunger receiving portion and the fixing holes may be positioned between the both barrel receiving portions.

In the above embodiment, the coupling member is fixed to the adapter. However, in other embodiments, the coupling member may be fixed directly to the barrel, in which the syringe can be mounted directly to the rotor or the rotating bucket without an adapter.

Referring to FIG. 40, the centrifuging device may comprise a barrel 3110, a plunger 3120 and a coupling member 3200. A fixing hole 3116a may be formed in the barrel 3110, and the coupling member 3200 may be engaged with the fixing hole 3116a and a coupling hole 3122 of the plunger 3120.

For example, supporters 3116 may be formed at the other end of the barrel 3110 and the fixing hole 3116a may be formed in the supporter 3116. Occasionally, the fixing hole may be formed in the barrel without the supporter.

Referring to FIG. 41, a coupling member 3200' may be positioned at the other end of the barrel 3110 to rotate and be fixed to the coupling hole 3122 selectively. The coupling member 3200 is shaped of "L" to rotate around the center positioned at the finger flange 3114.

Plurality of the coupling holes are formed along the plunger 3120 and the coupling member 3200 can fix the plunger 3120 to the barrel 3110 not to move.

Referring to FIG. 42, a centrifuging device may comprise a barrel, a plunger 3120, a coupling member 3200 and a movable coupler 3140.

The movable coupler 3140 may provided on the plunger 3120 to move along the plunger 3120 and a coupling hole 3122 may be formed in the movable coupler 3140. The movable coupler 3140 can move along the plunger 3120 according to the state of the plunger 3120, such that the position of the coupling hole 3122 can be changed by the movement of the movable coupler 3140.

An operator 3160 may be provided on the plunger 3120 to control the position of the movable coupler 3140, which the user may rotate the operator 3160 to move the movable coupler 3140.

The operator 3160 may be provided to rotate and move on the plunger 3120. For example, a guide screw 3150 may be formed on the plunger 3120 and the operator 3160 may be engaged on the guide screw 3150 to rotate and move on the guide screw 3150.

The guide screw 3150 may have a conventional screw structure, and the operator 3160 may rotate on the screw structure and move along the plunger 3120.

The position of the movable coupler 3140 may be selected by rotating the operator 3160, and the user can change the position of the movable coupler to coincide the coupling hole 3122 and the fixing hole 3116a.

For fixing the plunger 3120 to the barrel 3110, supporters 3116 may be formed at the other end of the barrel 3110 and the fixing hole 3116a may be formed in the supporter 3116. The coupling member 3200 passes through the fixing hole 3116a to be fixed to the coupling hole of the movable coupler 3140.

When the coupling member 3200 is engage with the fixing hole 3116a and the coupling hole 3122, the plunger 3120 may be moved by rotating the operator 3160. The position of the plunger 3120 can be finely controlled by using the operator 3160.

FIG. 44 is a block diagram illustrating a centrifuging method according to a fourth embodiment of the present invention, FIG. 45 is a block diagram illustrating a centrifuging process in detail according to the fourth embodiment of the present invention, and FIG. 46 is a perspective view illustrating a structure of a centrifuging adapter according to the fourth embodiment of the present invention.

And, FIGS. 47 to 49 are sectional views illustrating processes of a first centrifuging and discharging to remove one part of a mixture according to the fourth embodiment of the present invention, FIGS. 50 to 52 are sectional views illustrating processes of a second centrifuging and discharging to remove another part of the remained mixture according to the fourth embodiment of the present invention, and FIG. 53 is a sectional view illustrating a practical usage of target element extracted after the second centrifuging according to the fourth embodiment of the present invention.

As shown in the drawings, a centrifuging device according to the fourth embodiment comprises a syringe 411 and an adapter 4200.

The syringe 4100 may be a general syringe including the barrel 4110 and the plunger 4120, and may not limit the scope of the present invention by its kinds or properties.

The barrel 4110 may be a cylindrical hollow body and have a nozzle 4112 formed at the one end of the barrel 4110 for receiving blood or other fluidic material. The other end of the barrel 4110 is opened to permit the plunger 4120 to enter and move. The barrel 4110 may have a finger flange 4114 formed at the other end opposite to the nozzle 4112. The finger flange 4114 may have a hole-shaped structure (not shown) in other embodiments.

The nozzle 4112 may be temporarily sealed by a cap (not shown) or other sealing members during the first and the second centrifuging.

The plunger 4120 enters through the other end of the barrel 4110 to move straightly, and may let the fluidic material enter or go out via the nozzle 4112.

The plunger 4120 may include an end flange 4122 which have an enlarged diameter or size. In this embodiment, the end flange 4122 is shaped of a disc. In other embodiments, end flanges may have a different shape except a disc and may be positioned to be separated from the end of the plunger 4120.

For reference, the mixture in this specification may mean a object for centrifugation and may be selected in all kinds of material or mixture. For example, the mixture may be blood, secretion or any sample collected from human or animals.

In this specification, the adapter 4300 may be mounted to a rotor of a centrifuging device and be provided with various structures or types not to limit the scope of the present invention. For example, the adapter 4300 may be applied to various types of rotors, such as swing-out rotors or fixed-angle rotors.

The adapter 4200 and the rotor may be mutually connected by using a conventional connecting structure or indirectly by using a rotating bucket.

The adapter 4200 may be mounted to the rotor directly or indirectly, in a normal position in which the nozzle directs outside or in a reverse position in which the nozzle directs inside. The adapter 4200 may be composed of several parts, e.g. an adapter body, which are assembled by conventional holders, such as pins, clamps, screws, etc., to fix the barrel and the plunger.

The adapter 4200 may comprise the adapter body 4201, a barrel receiving portion 4210 and a plunger receiving portion 4220, which makes the syringe 4100 be settled during the centrifuging.

The barrel receiving portion 4210 is formed in the adapter body 4201 to hold the barrel 4110. The barrel receiving portion 4210 may be formed concavely according to the barrel 4110 to hold the barrel 4110. For example, the barrel receiving portion 4210 may have a flange slit 4214 to receive the finger flange 4114 of the barrel 4110 and fix the barrel 4110 stably.

In this embodiment, the flange slit 4214 is formed in the middle of the barrel receiving portion 4210, but another barrel receiving portion is formed in accordance with the precise contour of the barrel.

The adapter body 4201 may further comprise a plunger receiving portion 4220 for holding the plunger 4120. The plunger receiving portion 4220 may be adjacent to the barrel receiving portion 4210, and the plunger receiving portion 4220 may include plurality of plunger slits 4222 to fix the end flange 4122 of the plunger 4120. The end flange 4122 is held in one of the plunger slits 4222 to limit the movement of the plunger 4120.

Plurality of the plunger slits 4222 are formed along the adapter, and the user can fix the end flange 4122 to one of the plunger slits 4222. The distance between the end flange 4122 and the barrel 4110 may be changed according to the volume of the mixture in the barrel 4110.

The plunger slits may have various parameters. For example, the plunger slits 4222 may be arranged by a regular interval or by a irregular interval.

Hereinafter, the centrifuging method is described by using the syringe and the adapter.

Referring to FIGS. 44 to 45, the centrifuging method according to the present invention comprises providing the syringe 4100 which includes the barrel 4110 having the nozzle 4112 and the plunger 4120 moving straightly in the barrel 4110 to have the end flange 4122 (S4010), providing the adapter 4200 including the barrel receiving portion 4210 for holding the barrel 4110 and the plunger receiving portion 4220 having a plurality of plunger slits 4222 for holding the end flange 4122 (S4020), placing the barrel 4110 in the barrel receiving portion 4210 and the end flange 4122 in one of the plunger slits 4222 (S4030), and performing a centrifugation by rotating the adapter 4200 (S4040).

The step of performing the centrifugation comprises first centrifuging the mixture in the syringe 4100 of which the nozzle 4112 directs opposite to the rotating center in the adapter 4200 (S4032), discharging one part of the mixture which is adjacent to the nozzle 4112 after the first centrifuging (S4034), second centrifuging the mixture in the syringe 4100 after reversing the syringe 4100 in the adapter 4200 (S4036), and discharging another part of the mixture which is adjacent to the nozzle 4112 after the second centrifuging (S4038).

At first, blood may be collected in the barrel 4110. As mentioned the above, the blood can enter into the barrel 4110 via the nozzle 4112 when the plunger 4120 moves back. The blood as the mixture may be supplied directly from the human body through a needle (see Ref. No. 4132 in FIG. 53) mounted to the nozzle 4112. Otherwise, the blood may be supplied from another reservoir containing ready-collected blood.

As shown in FIG. 46, the syringe 4100 is mounted on the adapter 4200 where the plunger 4120 is fixed to the adapter 4200. The barrel 4110 is settled in the barrel receiving portion 4210 and the end flange 4122 is fixed in one of the plunger slits 4222.

When the barrel 4110 is settled in the barrel receiving portion 4210, the finger flange 4114 at the other end of the barrel 4110 may be fixed in the flange slit 4212 formed in the barrel receiving portion 4210.

As shown in FIG. 47, the adapter 4200 holding the syringe 4100 may be rotated by a conventional centrifuging device (not shown) to perform a first centrifuging with the blood in the barrel 4110. In this instance, the adapter 4200 is arranged on the centrifuging device, in which the nozzle 4112 of the syringe 4100 directs to the outside opposite to a rotating center. The rotating center may be understood as equal to the rotating axis of the rotor on which the adapter 4200 is mounted.

When the syringe 4100 of which the nozzle 4112 directs outside rotates for centrifuging, the blood can be divided into layers, as shown in FIG. 48, due to the differences of the densities of the elements. In this instance, one specific part A which is heaviest in the blood is positioned at the most outside layer which is farthest from the rotating center. For reference, the layer for the heaviest element in the blood may contain red blood cells.

Then the one specific part A of the blood, which is adjacent to the nozzle 4112 after the first centrifuging, may be discharged via the nozzle 4112. As shown in FIG. 49, the plunger 4120 moves toward the nozzle 4112 to make the one specific part A be discharged from the barrel 4110 to the outside.

In FIG. 35, the adapter 4200 is reversed on the contrary to the first centrifuging and the second centrifuging may be performed to divide the blood remained in the syringe 4100. The adapter 4200 is mounted in reversed direction, in which the nozzle 4112 of the syringe 4100 directs to the rotating center.

When rotating the adapter 4200 in which the nozzle 4112 of the syringe 4100 directs to the center, the remained mixture may be divided into layers of plasma and platelets as shown in FIG. 51. In this instance, the another specific part B which is relatively light in the remained blood is positioned at the most inside layer which is nearest to the nozzle 4112 in the barrel 4110. For reference, the layer for the light element in the blood may contain blood plasma.

The rotating speeds for the first and the second centrifuging may be different from each other. For one example, the rotating speed for the first centrifuging may be about 2500~3300 rpm, while the rotating speed for the second centrifuging may be about 4000~5500 rpm.

And then the anther specific part B of the blood, which is adjacent to the nozzle 4112 after the second centrifuging, may be discharged via the nozzle 4112 too. As shown in FIG. 52, the plunger 4120 moves toward the nozzle 4112 to make the another specific part B be discharged from the barrel 4110 to the outside.

After the one specific part A and the second specific part B are discharged from the blood, the target element C remaining in the barrel 4110 may contain blood platelet richly.

As mentioned the above, the blood platelets may be extracted from the blood in the syringe 4100, through the first and the second centrifuging, and the extracted blood platelets may be used to various medical experiments and researches, or may be injected directly to patient by the syringe 4100 and a needle 4132 mounted to the nozzle 4112, as shown in FIG. 53.

FIGS. 54 and 55 are perspective views illustrating the structures of centrifuging adapters according to other embodiments of the present invention.

In the above embodiment, the direction of the syringe is fixed in the adapter. However, in other embodiments, the direction of syringes may be freely selected in an adapter.

Referring to FIG. 54, a centrifuging device according to another embodiment of the present invention comprises the syringe 4100 including the barrel 4110 and the plunger 4120, and the adapter 4200 in which the barrel receiving portion 4210 and the plunger receiving portion 4220 are formed. Plurality of the plunger slits 4222 are formed along the plunger receiving portion 4220. The barrel receiving portion is composed of a first barrel receiving portion 4210' and a second barrel receiving portion 4210", and the plunger receiving portion 4220' is provided between the first barrel receiving portion 4210' and the second barrel receiving portion 4210" which are directed opposite to each other.

For the first centrifuging, the barrel 4110 may be positioned in the first barrel receiving portion 4210', while, for the second centrifuging, the barrel 4110 may be positioned in the second barrel receiving portion 4210". The plunger 4120 and the end flange 4122 may be positioned in the plunger receiving portion 4220' and the plunger slit 4222'.

Referring to FIG. 55, a centrifuging device according to another embodiment of the present invention, comprises the syringe 4100 including the barrel 4110 and the plunger 4120, and the adapter 4200. Plurality of the plunger slits 4222 are formed along the plunger receiving portion, and the barrel receiving portion includes the first barrel receiving portion 4210 and the second barrel receiving portion. The plunger receiving portion is provided in the first barrel receiving portion.

For the first centrifuging, the barrel 4110 may be positioned in the first barrel receiving portion 11210, and the plunger 4120 may be positioned in the second barrel receiving portion 11210', wherein the end flange 4122 may be fixed in the plunger slit 11222 in the second barrel receiving portion 11210'. While, for the second centrifuging, the barrel 4110 may be positioned in the second barrel receiving portion 11210', and the plunger 4120 may be positioned in the first barrel receiving portion 11210, wherein the end flange 4122 may be fixed in the plunger slit 11222 in the first barrel receiving portion 11210.

FIGS. 56 to 58 are views illustrating an adapter according to another embodiment of the present invention.

Referring to FIG. 56, an adapter according to this embodiment may comprise a stopper 4400 which is formed to be fixed in the plunger slit 4222. The stopper 4400 may be inserted into the plunger slit 4222 to support the back side of the end flange 4122.

The stopper 4400 may be useful if the end flange 4122 is not big enough to be fixed in the plunger slit 4222. In this instance, the stopper 4400 is inserted into the plunger slit 4222 to safely support the end flange 4122.

Referring to FIGS. 57 and 58, the adapter body 4201 may further include a chamber receiving portion 4240 near the barrel receiving portion 4210, and the chamber receiving portion 4240 may hold a separable chamber 4300 which can be selectively connected the nozzle 4112. For example, in the first centrifuging, the one part of the blood may be collected in the separable chamber 4300 which can be separated with the adapter 4200 and the syringe 4100 with the one part of the blood.

The separable chamber 4300 may have a hollow cylindrical body to be spatially connected to the barrel 4110. The separable chamber 4300 may have a connecting portion which can be coupled with the nozzle.

The chamber receiving portion 4240 may be shaped concavely to receive the separable chamber 4300. For one example, the chamber receiving portion 4240 may be formed to have an inner surface which is the same to the contour of the separable chamber 4300.

The first centrifuging may be performed in a state that the syringe 4100 and the separable chamber 4300 are coupled in the adapter 4200. The one part of the bood which should be removed may be collected in the separable chamber 4300. When the syringe 4100 and the separable chamber 4300 rotate for the centrifuging, the red blood cells may be collected in the separable chamber 4300 to be separated from the other elements.

In this instance, it is not preferable that all the red blood cells are collected in the separable chamber 4300 during the first centrifuging, because portion of the blood platelets can be collected in the separable chamber. Accordingly, it is preferable that little portion of the red blood cells remain in the barrel adjacent to the nozzle.

By using the separable chamber 4300 in the first centrifuging, the red blood cells may be collected mainly in the separable chamber 4300 and prevent the purity of the platelets from being decreased due to the red blood cells remaining in the syringe 1100.

Generally, the inside surface of the barrel may have a certain surface roughness degree, but not zero. So, small amount of red blood cell which could be survived on the inside surface of the barrel can decrease the purity of the platelets, even after the second centrifuging. However, if most of the red blood cells would be collected in the separable chamber 4300, the amount of the red blood cells remained in the barrel 4110 can be minimized, and the purity of the platelets can be improved.

In the present embodiment, the ceiling of the separable chamber is simply flat, while the ceiling of another separable chamber may be inclined for an easy layer separation.

FIG. 59 is a perspective view illustrating a syringe according to the fifth embodiment of the present invention.

Referring to FIG. 59, The syringe of the fifth embodiment comprises a barrel 5110, a plunger 5120 and a plunger handle 5130.

The syringe according to the fifth embodiment may be used for centrifuging or general purpose, which may be used for general drug injections, experiments, researches, etc. The syringe can be used for various purposes.

The barrel 5110 may have a hollow cylindrical body with a predetermined diameter or volume. The barrel 5110 includes one end where the nozzle 5112 is located and the other end which is opened to permit the plunger 5120 to enter and move. The nozzle 5112 can be temporarily sealed by a cap or other sealing members.

The plunger 5120 enters through the other end of the barrel 5110 to move straightly, and may let the fluidic material enter or go out via the nozzle 5112. The barrel 5110 may have a finger flange 5114 formed at the other end opposite to the nozzle 5112. The finger flange 5114 may have a hole-shaped structure (not shown) in other embodiments.

The plunger 5120 enters through the other end of the barrel 5110 to move straightly, the plunger 5120 may let the fluidic material enter or go out via the nozzle 5112.

The plunger handle 5130 is provided at the other end of the barrel 5110 to operate with the plunger 5120. The plunger 5120 can be moved by the plunger handle 5130. The plunger handles may have various structures.

The plunger 5120 and the plunger handle 5130 are understood that both are functionally connected directly or indirectly and the plunger 5120 may interwork with the plunger handle 5130. So, the user makes the plunger 5120 moving by the operation of the plunger handle 5130.

Hereinafter, the plunger handle 5130 is provided on a housing 5140. For example, the plunger handle 5130 includes the housing 5140, a handle part 5150 and a connecting part 5160 connecting the plunger 5120 and the handle part 5150.

The housing 5140 may be formed integrated with or separated from the barrel 5110. In this embodiment, the housing 5140 is formed integrated with the barrel 5110 and the connecting part 5160 forms a part of the plunger 5120

For an easy hand grip, the housing 5140 of the plunger handle 5130 may be relatively thin or narrow rather than the barrel 5110, to have a D-cut section.

The handle part 5150 moves straightly in the housing 5140. For example, the housing 5140 includes a guide slot 5140a and part of the handle part 5150 may be exposed through the handle. The guide slot 5140a is formed straightly and the plunger handle moves straightly along the guide slot 5140a. A user grasping the barrel 5110 can operate the plunger handle 5130 using his or her finger to move the plunger 5120.

Along the guide slot 5140a of the housing 5140, plurality of coupling grooves 5170 may be formed by a regular interval. The handle part 5150 can be changed between a normal state and release state. In the normal state, the handle part 5150 can be locked or stopped by the coupling grooves 5170. However, in the release state, the handle part can be released from the coupling grooves 5170 to move freely.

The plunger handle 5130 may further include an elastic portion 5152 elastically supporting the connecting part 5160 and the handle part 5150. The handle part 5150 can be elastically supported to be restored to the normal state.

The coupling grooves 5170 may be formed by a regular or irregular interval, or the number or the interval of the coupling grooves may be variously selected under the required conditions.

In this embodiment, the coupling grooves are formed on the both sides along the guide slot, however the coupling grooves may be formed on only one side according to another embodiment.

Hereinafter, the centrifuging method using the one syringe is described according to the fifth embodiment of the present invention.

FIGS. 60 to 62 are sectional views illustrating processes of a first centrifuging and discharging to remove one part of a mixture according to the fifth embodiment of the present invention, FIGS. 63 to 65 are sectional views illustrating processes of a second centrifuging and discharging to remove another part of the remained mixture according to the fifth embodiment of the present invention, and FIG. 66 is a sectional view illustrating a practical usage of target element extracted after the second centrifuging according to the fifth embodiment of the present invention.

At first, blood may be collected in the barrel 5110. As mentioned the above, the blood can enter into the barrel 5110 via the nozzle 5112 when the plunger 5120 moves back. The blood as the mixture may be supplied directly from the human body through a needle (see Ref. No. 5132 in FIG. 66) mounted to the nozzle 2112. Otherwise, the blood may be supplied from another reservoir containing ready-collected blood.

As shown in FIG. 60, the syringe may be rotated by a conventional centrifuging device (not shown) to perform a first centrifuging with the blood in the barrel 5110. In this instance, the syringe is arranged on the centrifuging device, in which the nozzle 5112 directs to the outside opposite to a rotating center.

The syringe may be mounted to the rotor by using a general adapter or rotation bucket, or be mounted directly on the rotor.

When the syringe of which the nozzle 5112 directs outside rotates for centrifuging, the mixture can be divided into layers, as shown in FIG. 61, due to the differences of the densities of the elements. In this instance, one specific part A which is heaviest in the blood is positioned at the most outside layer which is farthest from the rotating center. For reference, the layer for the heaviest element in the blood may contain red blood cells.

Then the one specific part A of the blood, which is adjacent to the nozzle 5112 after the first centrifuging, may be discharged via the nozzle 5112. As shown in FIG. 62, the plunger 5120 moves toward the nozzle 5112 to make the one specific part A be discharged from the barrel 5110 to the outside.

In FIG. 63, the second centrifuging may be performed to divide the blood remained in the syringe. The syringe is mounted in reversed direction, of which the nozzle 5112 directs to the rotating center.

When rotating the syringe in which the nozzle 5112 directs to the center, the remained mixture may be divided into layers of plasma and platelets as shown in FIG. 64. In this instance, the another specific part B which is relatively light in the remained blood is positioned at the most inside layer which is nearest to the nozzle 5112 in the barrel 5110. For reference, the layer for the light element in the blood may contain blood plasma.

The rotating speeds for the first and the second centrifuging may be different from each other. For one example, the rotating speed for the first centrifuging may be about 2500~3300 rpm, while the rotating speed for the second centrifuging may be about 4000~5500 rpm.

And then the anther specific part B of the blood, which is adjacent to the nozzle 5112 after the second centrifuging, may be discharged via the nozzle 5112 too. As shown in FIG. 65, the plunger 5120 moves toward the nozzle 5112 to make the another specific part B be discharged from the barrel 5110 to the outside.

After the one specific part A and the second specific part B are discharged from the blood, the target element C remaining in the barrel 5110 may contain blood platelet richly.

As mentioned the above, the blood platelets may be extracted from the blood in the syringe, through the first and the second centrifuging, and the extracted blood platelets may be used to various medical experiments and researches, or may be injected directly to patient by the syringe and a needle 5132 mounted to the nozzle 5112, as shown in FIG. 66.

During the first and the second centrifuging, the handle part 5150 is locked in one of the coupling grooves 5170, so that the plunger 5120 is fixed to the barrel 5110 not to move.

The user holding the housing 5140 with a hand may push the handle part 5150 by using a finger to move the plunger 5120, so that part of the mixture positioned near the nozzle can be discharged via the nozzle 5112.

FIGS. 67 to 71 are perspective views illustrating syringes according to other embodiments of the present invention.

In the above embodiment, the handle part is locked in the coupling groove to lock the plunger, however the handle part may be locked by a screw according to another embodiment.

Referring to FIG. 67, the handle part 5151 is connected to the connecting part 5161 to move straightly in the housing 5141. The handle part 5151 may be locked by a screw.

The locking structure of the handle part 5151 may be variously selected. For example, the handle part 5151 is engaged with the connecting part 5160 by screw coupling to contact to and press the inside of the housing 5141.

The handle part may be locked by different types of locking members.

Referring to FIG. 68, the syringe may comprise the barrel 5110, the plunger 5120 and the plunger handle 5132, and the plunger handle 5132 may comprise a housing 5142 provided to the barrel opposite to the nozzle 5112, a handle part 5152 in the housing 5142, and connecting part 5162 connecting the plunger 5120 and the handle part 5152. The plunger 5120 may move straightly in the barrel 5110 by the rotating of the handle part 5152.

A guide screw 5152a is provided in the housing 5142 and arranged concentrically with the plunger 5120 and the handle part 5152. Since the handle part 5152 and the guide screw 5152a are engaged by screw coupling, the rotating of the handle part 5152 can make the handle part 5152 move along the guide screw 5152a. The handle part 5152 is physically connected with the plunger 5120 via the connecting part 5162. So, when the handle part 5152 rotates, the plunger 5120 moves straightly in the barrel 5110.

Since only the rotating of the handle part 5152 can move the handle part 5152 move on the guide screw 5152a, the handle part 5152 can be stably fixed at a predetermined position without an additional locking member.

In the plunger handles using the guide screw, the guide screw may be arranged concentrically with the plunger or not.

Referring to FIG. 69, a plunger handle 5133 may include a housing 5143, a handle part 5153, a connecting part 5163, a ratchet pawl 5170 and a ratchet portion 5170a. The ratchet pawl 5170 is installed rotatably on the handle part 5153 or the connecting part 5163, and the ratchet portion 5170a may include many ratchet steps in the housing 5143. The ratchet pawl 5170 may pass over the ratchet portion 5170a when moving in one direction, but may be locked by the ratchet portion 5170a when moving in the other direction.

Referring to FIG. 70, a syringe according another embodiment of the present invention may comprise the barrel 5110, the plunger 5120 and a plunger handle 5134, and the plunger handle 5134 may comprise a housing 5144 provided to the barrel 5110 opposite to the nozzle 5112, a handle part 5154 in the housing 5144, a transmission 5180, and connecting part 5164 connected with the plunger 5120 to move straightly by the transmission 5180. The plunger 5120 may move straightly in the barrel 5110 by the rotating of the handle part 5154.

In this embodiment, the handle part 5180 is provided perpendicular to plunger 5120. The transmission 5180 converts the rotating of the handle part 5180 into the straight movement of the connecting part 5164. For example, the transmission 5180 may be provided using the combination of the gears, such as a first bevel gear 5181 and a second bevel gear 5182. The combination of the gears further includes a pinion gear 5183 rotating with the second bevel gear 5182 and a rack gear 5184 engaged with the pinion gear 5183. The rotating of the handle part 5154 may be used to make the plunger 5120 move straightly, going through the first and second bevel gears 5181 and 5182, the pinion gear 5183 and the rack gear 5184 in order.

The transmission is provided using the combination of gears, however it can be provided using the combination of cams or other mechanical parts.

Referring to FIG. 71, a syringe may comprise the barrel 5110, the plunger 5120 and a plunger handle 5130'. The barrel 5110 and the plunger handle 5130' may be manufactured individually and assembled when they should be used. The plunger handle 5130' and the barrel 5110 may be coupled using the conventional coupling structures, for example by using a protrusion and a groove.

FIG. 72 is a sectional view illustrating a syringe and a centrifuging method according to a sixth embodiment of the present invention, and FIG. 73 is a sectional view illustrating a practical usage of the syringe and the centrifuging method of the sixth embodiment of the present invention.

Referring to FIGS. 72 and 73, a centrifuging syringe 6100 may comprise a barrel 6110 and a plunger 6120. The barrel 6110 and the plunger 6120 may be a conventional structure of a general syringe.

A path 6160 is provided in the plunger 6120. The path 6160 may be connected via a connection hole 6165 to an outer suction device 6010 or another syringe 6020. The path 6160 can discharge or transfer one part of the mixture which is adjacent to a plunger head 6122, not via the nozzle 6112 but via the plunger 6120.

In this embodiment, removed elements which don't contain target element may be discharged respectively via the nozzle 6112 and the path 6160 of the plunger 6120. The removed element near the plunger head 6122 may be discharged to the outside or be saved in the plunger 6120 temporarily.

In (a) of FIG. 72, the syringe 6100 contains the blood sample 6030 which can be collected directly from a human body or from another blood reservoir.

In (b) of FIG. 72, the blood sample 6030 in the syringe 6100 is centrifuged by a centrifuging device. After centrifuging, the blood sample may be divided into the layers of red blood cells 6032, PRP 6034 and plasma 6036, in which the layer of PRP is located in the middle of the layers.

During the centrifuging, it is preferable that the barrel 6110 and the plunger 6120 are fixed to each other not to move the process.

To prevent the red blood cells from be remained on an inner wall of the barrel 6110, a separable chamber may be mounted to the nozzle to collect most of the red blood cells after the centrifuging. Accordingly, the red blood cell 6032 may be collected mainly in the separable chamber, not in the barrel 6110.

In (c) of FIG. 72, the red blood cells 6032 may be discharged via the nozzle 6112 of the barrel 6110. The user can discharge the red blood cells 6032 by push the boundary of the red blood cells 6032 and the PRP 6034 to the outlet of the nozzle 6112. In this instance, the plasma 6036 may be remained over the layer of the PRP 6034.

In (d) of FIG. 72, after opening the path 6160, the plasma 6036 near the plunger head 6122 may enter into the path 6160 to be separated from the PRP 6034. The plasma 6036 in the path 6160 may be discharged through the suction device 6010 or the another syringe 6020. To open and close the path 6160, the plunger 6120 may include any valves.

The path 6160 of this embodiment is formed in longitudinal direction in the plunger 6120. One end of the path 6160 is connected to the plunger head 6122 and the other end if connected to a end flange to selectively connect the outside and an inner space defined by the barrel 6110 and the plunger head 6122.

After discharging the plasma 6036 near the plunger head 6122, the PRP 6034 as the target element is remained in the barrel 6110. As shown in FIG. 73, the extracted PRP 6034 may be applied to a medical care, surgery or experiment.

FIG. 74 is a perspective view illustrating a centrifuging syringe according to one embodiment of the present invention, and FIG. 75 is a sectional view illustrating the centrifuging syringe of FIG. 74.

Referring to FIGS. 74 and 75, a centrifuging syringe 6200 may comprise a barrel 6210, a plunger 6220, and a path 6260, and the plunger 6220 slides in the barrel 6210 to let the blood or sample be inserted or discharged.

The plunger 6220 includes a first plunger body 6230 and a second plunger body 6240 to form a double body structure. The first plunger body 6230 may contact the inside of the barrel 6210 to slide in it, and the second plunger body 6240 is inserted in the first plunger body 6230.

The first plunger body 6230 is provided in a hollow cylindrical shape, and a first pipe 6232 is provided in the center of the first plunger body 6230 to form the path 6260. The first pipe 6232 has one end connected to the inner space of the barrel 6210 and the other end extended opposite to the nozzle. In accordance with the first pipe 6232, a second pipe 6242 is provided in the second plunger body 6240 to receive the first pipe 6232. The first pipe 6232 and the second pipe 6242 may seal the path 6260.

The first pipe 6232 and the second pipe 6242 form connection holes 6234 and 6244 respectively. The connection holes 6234 and 6244 may selectively coincide with each other to connect or cut between the inner space of the barrel 6210 and the path 6260. The connection holes 6234 and 6244 are formed respectively at the end of the first pipe 6232 and the second pipe 6242. While the second plunger body 6240 rotates in the first plunger body 6230, the connection holes 6234 and 6244 may form a space connection between the barrel 6210 and the path 6260.

The second plunger body 6240 includes the second pipe 6242 in its center and has a cross-shaped section to rotate in the first plunger body 6230. While the second plunger body 6240 rotates, the connection holes 6234 and 6244 may be coincident with each other to let the outer suction device or another syringe discharge one part of the mixture which is positioned near the plunger 6220.

FIG. 76 is a sectional view illustrating a centrifuging syringe according to one embodiment of the present invention, and FIG. 77 is a sectional view illustrating the operating mechanism of the centrifuging syringe of FIG. 76.

Referring to FIGS. 76 and 77, a centrifuging syringe 6300 may comprise a barrel 6310, a plunger 6320, and a path 6360, and the plunger 6320 slides in the barrel 6310 to let the blood or sample be inserted or discharged.

The plunger 6320 includes a first plunger body 6330 and a second plunger body 6340 to form a double body structure. The first plunger body 6330 may contact the inside of the barrel 6310 to slide in it, and the second plunger body 6340 is inserted in the first plunger body 6330.

The first plunger body 6330 is provided in a hollow cylindrical shape, and the path 6360 is provided in the center of the first plunger body 6330. The second plunger body 6340 is positioned in the first plunger body 6330 to move by screw engagement. The second plunger body 6340 includes a valve head 6344 for a connection hole 6334 formed at the front of the first plunger body 6330. When the second plunger body 6340 rotates in the first plunger body 6330, the valve head 6344 moves forward to open the path 6360. When the second plunger body 6340 rotates in the opposite direction, the valve head 6344 moves backward to close the path 6360.

The path 6360 in the first plunger body 6330 is not connected to the outside, but forms a reserving space. After opening the path 6360, one part of the mixture which doesn't contain the target element may flow in the path 6360 by pushing the plunger 6320. By forming vacuum in the path 6360, the user may make the inflow be smooth and easy.

FIG. 78 is a sectional view illustrating a centrifuging syringe according to one embodiment of the present invention, and FIG. 79 is a sectional view illustrating the operating mechanism of the centrifuging syringe of FIG. 78.

Referring to FIGS. 78 and 79, a centrifuging syringe 6400 may comprise a barrel 6410, a plunger 6420, and a path 6460, and the plunger 6420 slides in the barrel 6410 to let the blood or sample be inserted or discharged.

The plunger 6420 includes a first plunger body 6430 and a second plunger body 6440 to form a double body structure. The first plunger body 6430 may contact the inside of the barrel 6410 to slide in it, and the second plunger body 6440 is inserted in the first plunger body 6430.

The first plunger body 6430 is provided in a hollow cylindrical shape, and the path 6460 is provided in the center of the first plunger body 6430. The second plunger body 6440 is positioned in the first plunger body 6430 to move by screw engagement. The second plunger body 6440 includes a valve head 6444 for a connection hole 6434 formed at the front of the first plunger body 6430. When the second plunger body 6440 rotates in the first plunger body 6430, the valve head 6444 moves backward to open the path 6460. When the second plunger body 6440 rotates in the opposite direction, the valve head 6444 moves forward to close the path 6460.

The path 6460 in the first plunger body 6430 may be connected to the outside via hose or the like, and form a reserving space in the plunger 6420. After opening the path 6460, one part of the mixture which doesn't contain the target element may flow in the path 6460 by pushing the plunger 6420. By using the outer suction device or another syringe, the user may make the inflow be smooth and easy.

FIG. 80 is a perspective view illustrating a centrifuging syringe according to one embodiment of the present invention, FIG. 81 is a perspective view illustrating an operating mechanism of the centrifuging syringe of FIG. 80, and FIG. 82 is a partially enlarged sectional view illustrating the structure of the syringe of FIG. 80.

Referring to FIGS. 80 to 82, a centrifuging syringe 6500 may comprise a barrel 6510, a plunger 6520, and a path 6560, and the plunger 6520 slides in the barrel 6510 to let the blood or sample be inserted or discharged.

The plunger 6520 includes a first plunger body 6530 and a second plunger body 6540 to form a double body structure. The first plunger body 6530 and the second plunger body 6540 are provided in a hollow cylindrical shape. The first plunger body 6530 may contact the inside of the barrel 6510 to slide in the barrel 6510, and the second plunger body 6540 may contact the inside of the first plunger body 6530 to slide in the first plunger body 6530.

At the front end of the first plunger body 6530 and the second plunger body 6540, connection holes 6534 and 6544 are formed respectively. The connection holes 6534 and 6544 may be in accordance with each other and may be coincident at a predetermined angle. While the second plunger body 6540 rotates in the first plunger body 6530, the path 6560 can be opened when the connection holes 6534 and 6544 are coincident. In case that the connection holes 6534 and 6544 are not coincident, the path 6560 gets cut off.

The path 6560 of the second plunger body 6540 may be connected to the outside via other connection holes 6536 and 6546. After opening the path 6560, one part of the mixture which doesn't contain the target element may flow in the path 6560 by pushing the plunger 6520. In this instance, by using the outer suction device or another syringe, the user may make the inflow be smooth and easy through the above other connection holes 6536 and 6546.

FIG. 83 is a perspective view illustrating a centrifuging syringe according to one embodiment of the present invention, and FIG. 84 is a sectional view illustrating the centrifuging syringe of FIG. 83.

Referring to FIGS. 83 and 84, a centrifuging syringe 6600 may comprise a barrel 6610, a plunger 6620, and a path, and the plunger 6620 slides in the barrel 6610 to let the blood or sample be inserted or discharged.

The plunger 6620 includes a first plunger body 6630 and a second plunger body 6640 to form a double body structure. The first plunger body 6630 receives the second plunger body 6640 inside. The first plunger body 6630 may contact the inside of the barrel 6610 to slide in the barrel 6610, and the second plunger body 6240 is inserted in the first plunger body 6230 to rotate around a central axis of the first plunger body 6630. The path is provided in the second plunger body 6640.

At the front end portion (ex. at the plunger head) of the first plunger body 6630 and the second plunger body 6640, connection holes 6634 and 6644 are formed respectively. The connection holes 6634 and 6644 may be in accordance with each other and may be coincident at a predetermined angle. While the second plunger body 6640 rotates in the first plunger body 6530, the path can be opened when the connection holes 6634 and 6644 are coincident. In case that the connection holes 6634 and 6644 are not coincident, the path gets cut off.

The path 6660 of the second plunger body 6640 may be connected to the outside via another connection hole 6646. After opening the path, one part of the mixture which doesn't contain the target element may flow in the path by pushing the plunger 6620. In this instance, by using the outer suction device or another syringe, the user may make the inflow be smooth and easy through the another connection hole 6646.

Although a few embodiments of the present invention have been shown and described, the present invention is not limited to the described embodiments. Instead, it would be appreciated by those skilled in the art that changes may be made to these embodiments without departing from the principles of the invention, the scope of which is defined by the claims and their equivalents.

The invention claimed is:

1. A method of centrifuging a mixture including red blood cells using a syringe which has only a single chamber and a nozzle at one end thereof, the method comprising the steps of:
   (a) taking the mixture including red blood cells in the syringe directly from a patient;
   (b) first centrifuging the mixture in the single chamber of the syringe at a first rotational speed to separate the mixture into at least a first part, a second part, and a third part, the nozzle of the syringe being directed opposite to a rotating center of a centrifuging device, wherein no parts of the syringe move relative to each other during the first centrifuging;
   (c) discharging the first part of the mixture which is adjacent to the nozzle after the first centrifuging while leaving the second part and the third part in the single chamber;
   (d) second centrifuging the mixture second part and the third part remaining in the single chamber of the syringe at a second rotational speed after step (c) after reversing the syringe, the second centrifuging to reverse the positioning of the second part and the third part within the single chamber, the nozzle of the syringe being directed to the rotating center, wherein no parts of the syringe move relative to each other during the second centrifuging; and
   (e) discharging the third part of the mixture which is adjacent to the nozzle after the second centrifuging such that only the second part remains in the single chamber of the syringe;
   wherein the second rotational speed is higher than the first rotational speed.

2. The method of claim 1, wherein the syringe includes a barrel having the nozzle at one end and a plunger entering through the other end of the barrel to move straightly in the barrel, and
   wherein the nozzle is sealed during the first centrifuging and the second centrifuging.

3. The method of claim 1, wherein the one part discharged by the first centrifuging contains red blood cells and the another part discharged by the second centrifuging contains blood plasma, and wherein a target element, which is remained in the syringe after discharging the one part and the another part, contains blood platelets.

4. The method of claim 2, wherein a plunger head of the plunger is provided with an adhesion barrier to prevent a target element from being adhered on the plunger head in the syringe after the second centrifuging.

5. The method of claim 1, wherein the syringe further includes a separable chamber separably mounted to the nozzle, thereby portion of the one part discharged by the first centrifuging is contained in the separable chamber and the separable chamber is separated after the first centrifuging.

* * * * *